US007579324B2

(12) United States Patent
Burnet et al.

(10) Patent No.: US 7,579,324 B2
(45) Date of Patent: Aug. 25, 2009

(54) CONJUGATES OF BIOLOGICALLY ACTIVE COMPOUNDS, METHODS FOR THEIR PREPARATION AND USE, FORMULATION AND PHARMACEUTICAL APPLICATIONS THEREOF

(75) Inventors: Michael Burnet, Kusterdingen (DE); Jan-Hinrich Guse, Tubingen-Buhl (DE); Hans-Jurgen Gutke, Stuttgart (DE); Albert Beck, Nehren (DE); Georgia Tsotsou, Tubingen (DE); Irina Droste-Borel, Tubingen (DE); Jeannette Reichert, Neustretten (DE); Kattie Luyten, Tubingen (DE); Maximilian Busch, Tubingen (DE); Michael Wolff, Kusterdingen (DE); Moussa Khobzaoui, Tubingen (DE); Simona Margutti, Tubingen (DE); Thomas Meindl, Tubingen (DE); Gene Kim, Tubingen (DE); Laurence Barker, Tubingen (DE)

(73) Assignee: c-a-i-r biosciences GmbH, Tuebingen (DE)

( * ) Notice: Subject to any disclaimer, the term of this patent is extended or adjusted under 35 U.S.C. 154(b) by 0 days.

(21) Appl. No.: 10/367,105

(22) Filed: Feb. 14, 2003

(65) Prior Publication Data

US 2004/0087517 A1 May 6, 2004

Related U.S. Application Data

(60) Provisional application No. 60/357,434, filed on Feb. 15, 2002.

(51) Int. Cl.
*A01N 43/04* (2006.01)
*A61K 31/70* (2006.01)
*C07H 17/08* (2006.01)

(52) U.S. Cl. .......................... 514/29; 514/183; 536/7.1; 536/7.2; 536/7.4

(58) Field of Classification Search ............... 536/4.1, 536/7.1, 7.2
See application file for complete search history.

(56) References Cited

U.S. PATENT DOCUMENTS

| 3,417,077 | A |   | 12/1968 | Murphy et al. ............ 260/210 |
|-----------|---|---|---------|-----------------------------------|
| 3,884,903 | A |   | 5/1975  | Jones et al. .............. 260/210 |
| 4,328,334 | A |   | 5/1982  | Kobrehel et al. ........... 536/7.4 |
| 4,382,086 | A |   | 5/1983  | Sciavolino et al. .......... 424/180 |
| 4,474,768 | A |   | 10/1984 | Bright ..................... 424/180 |
| 4,517,359 | A |   | 5/1985  | Kobrehel et al. ........... 536/7.4 |
| 4,834,973 | A |   | 5/1989  | Strahilevitz |
| 5,466,681 | A | * | 11/1995 | Krivan et al. .............. 514/54 |
| 5,486,536 | A | * | 1/1996  | Ward et al. ............... 514/460 |
| 5,516,864 | A |   | 5/1996  | Kuhn et al. ............... 526/263 |
| 5,676,971 | A |   | 10/1997 | Yoshioka et al. |
| 5,750,493 | A |   | 5/1998  | Sommadossi et al. ......... 514/1 |
| 5,827,533 | A |   | 10/1998 | Needham |
| 5,846,458 | A |   | 12/1998 | Yoshioka et al. |
| 5,928,868 | A | * | 7/1999  | Liu et al. ................. 435/6 |
| 5,969,161 | A | * | 10/1999 | Bonnet et al. .............. 549/271 |
| 6,043,227 | A |   | 3/2000  | Cheng et al. .............. 514/29 |
| 6,300,316 | B1|   | 10/2001 | Brightly et al. ............ 514/29 |
| 6,562,796 | B2|   | 5/2003  | Baldwin et al. ............ 514/31 |
| 7,091,187 | B2| * | 8/2006  | Mercep et al. ............. 514/29 |
| 2003/0068362 | A1 |   | 4/2003 | Soon-Shiong et al. |

FOREIGN PATENT DOCUMENTS

| EP | 0009944 B1 | 4/1980 |
| EP | 0044090 | 1/1982 |
| EP | 0159856 | 10/1985 |
| EP | 0189281 | 7/1986 |
| EP | 0467331 B1 | 1/1992 |
| EP | 0895999 A1 | 2/1999 |
| EP | 0984019 A1 | 3/2000 |
| EP | 0992509 A2 | 4/2000 |
| EP | 1088828 A2 | 4/2001 |
| EP | 1122261 A2 | 8/2001 |
| EP | 1167376 A1 | 1/2002 |
| EP | 1 036 083 B1 | 5/2004 |
| JP | 05163293 A | 6/1993 |
| WO | WO99/51616 | 10/1999 |
| WO | WO-99/63937 | 12/1999 |
| WO | WO-99/64032 | 12/1999 |
| WO | WO-99/64040 | 12/1999 |

(Continued)

OTHER PUBLICATIONS

Goodman and Gilman's, "The Pharmacalogical Basis of Therapeutics", 10th Edition, McGraw-Hill Medical Publishing Division, 2001, 54-57.

(Continued)

*Primary Examiner*—Traviss C McIntosh, III
(74) *Attorney, Agent, or Firm*—Edwards Angell Palmer & Dodge LLP; Jeffrey D. Hsi

(57) ABSTRACT

This invention features a compound of the following formula:

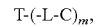

T is a transportophore, L is a bond or a linker having a molecular weight up to 240 dalton, C is a non-antibiotic therapeutic agent, and m is 1, 2, 3, 4, 5, 6, 7, or 8, in which the transportophore has an immune selectivity ratio of at least 2, the transportophore is covalently bonded to the non-antibiotic therapeutic agent via the bond or the linker, and the compound has an immune selectivity ratio of at least 2.

3 Claims, 10 Drawing Sheets

FOREIGN PATENT DOCUMENTS

| WO | WO-02/055531 A1 | 7/2002 |
| WO | WO-03/045319 | 6/2003 |
| WO | WO-03/070173 | 8/2003 |
| WO | WO-03/070254 A | 8/2003 |

OTHER PUBLICATIONS

Shibata et al., "Relationship between erythrocyte-to-plasma distribution ratio of cyclosporin and lymphocyte proliferation in renal transplant patient", Eur. J. Clin. Pharmacology (1997) vol. 51, p. 455-459.

Romo, D. et al., "Total Synthesis and Immunosuppressive Activity of (−)-Pateamine A and Related Compounds: Implementation of beta-Lactam Based MacroCclization," Journal of the American Chemistry Society, American Chemical Society, Washington, DC, vol. 120, No. 47, 1998, pp. 12237-12254.

Griffith E.C. et al., "Yeast three-hybrid system for detecting ligand-receptor interactionsl" Methods in Enzymology, Academic Press Inc., San Diego, CA. vol. 328, 2000, pp. 89-103.

Costa, A. M. et al., "Hybrids of macrolides and nucleobases or nucleosides," Tetrahedron Letters, Elsevier, Amsterdam, NL, vol. 41, No. 18, Apr. 2000, pp. 3371-3375.

Werner, R.G. et al., "Inhibition of protein synthesis by three erythromycin-derivatives," Biochemical and Biophysical Research Communications Aug. 14, 1978, vol. 83, No. 3, pp. 1147-1156.

Ghosh, M. et al., "Design, synthesis, and biological evaluation of isocycnurate-based antifungal and macrolide antibiotic conjugates: iron transport-medicated drug delivery," Bioorganic & Medicinal Chemistry Nov. 1995, vol. 3, No. 11, pp. 1519-1525.

Ianaro et al., "Anti-Inflammatory Activity of Macrolide Antibiotics", Jan. 2000, J. Pharmacology and Experimental Therapeutics, vol. 292, No. 1, pp. 156-163.

* cited by examiner

4

5

CONJUGATES OF BIOLOGICALLY ACTIVE COMPOUNDS, METHODS FOR THEIR PREPARATION AND USE, FORMULATION AND PHARMACEUTICAL APPLICATIONS THEREOF

CROSS-REFERENCE TO RELATED APPLICATIONS

This application claims benefit of U.S. provisional application No. 60/357,434, filed Feb. 15, 2002, the contents of which are incorporated herein by reference.

BACKGROUND

Successful therapy with a pharmaceutical agent requires that the agent satisfy numerous requirements imposed by the physiology of the host and of the disease or condition. The requirements include: (i) adequate ability to interact with the target receptor(s); (ii) appropriate physical properties for presence at the location of the receptors in concentrations that permit the interactions noted above; (iii) appropriate physical properties to allow the agent to enter the body and distribute to the location of the receptors by any means; (iv) sufficient stability in fluids of the body; (v) the absence of toxic effects in compartments where the therapeutic agent is most concentrated, or in any other compartment where the therapeutic agent is located; and (vi) the absence of sequestration into non-physiological compartments and so on.

In general, these compounding requirements limit the nature of pharmaceutical compounds that have utility in vivo and thus reduce the probability of discovering adequately active molecules from de novo starting points. In response to these constraints, significant effort has been applied to the question of predicting ideal physical properties for pharmaceutical molecules. Authors such as Lipinski (Lipinski et al., 2001) have described rules of therapeutic agent design which, amongst other parameters, predicts that ideal therapeutic agents will have few functions such as hydroxy groups, a molecular weight below 500 Da, mild basicity, and moderate lipophilicity (log P<5) (Lipinski et al., 2001). Unfortunately, these parameters are too general to inform the direct synthesis of highly bioavailable compounds. Furthermore, these requirements are not helpful for larger molecule chemistry (MW>500) such as the compounds disclosed here.

Recently, improvements in the technology of synthetic chemistry and molecular biology have allowed the testing of large numbers of molecules and the discovery of many ligands with adequate affinity to their targets to have some potential in vivo. Many such molecules prove inadequate on in vivo testing largely due to the manifold, stringent, and often conflicting (i.e. stability without toxicity) requirements outlined above.

In addition to the difficulties facing many new molecules, many existing molecules in clinical use also exhibit inadequate properties of uptake, distribution, stability and toxicity (Lipinski et al. 2001). These observations demonstrate, that in general, deficiencies in uptake, distribution, and stability result in inadequate therapy from existing molecules and inadequate and uneconomical probabilities of success in the discovery of new molecules.

Such problems often fall within the scope of therapeutic agent delivery—a discipline which combines many aspects of formulation with techniques for introducing the agent into the host body. Delivery methods are frequently designed to permit passage through a single barrier (i.e. the skin) (WO 01/13957) or the intestine (WO 01/20331) after which the agent must again conform with the general requirements above in order to act at the in vivo target. Certain delivery strategies involve a physical preparation such as liposomes (Debs et al. 1990; Jaafari, Foldvari, 2002) or anti-body conjugates (Everts et al., 2002) which further direct the molecules within the host body. Others rely on the addition of cationic lipids to formulations, the use of transport proteins as a route of uptake (WO 01/20331). The use of transport processes deliberately in therapeutic agent design is perhaps best illustrated by the nucleoside therapeutic agents, which to varying degrees, are taken up as metabolites and whose transport to mitochondria is a major cause of toxicity (WO 98/29437) For example, see European Patent No. 0009944B1, European Patent No. 0044090A3, and Japanese Patent No. 05163293. Such methods may enhance performance in therapy or reduce toxicity but they increase cost and require direct introduction into the blood stream which is impractical in chronic use.

More preferable would be small molecules that possess the appropriate structures and properties to mediate efficient uptake and stability. Such small molecules would ideally be able to carry a range of therapeutic agents of varying properties such that they could be commercialized in more than one indication. However, there is a requirement that they be inactive and stable enough to ensure that the cargo molecule is carried in the periphery (Harada et al. 2000).

The present invention represents a significant advance in that it provides for a means of improving the bioavailability and efficacy of a variety of molecules in vivo using a series of rational and facile assays to select desirable compounds based on known pharmacophores or pharmaceutical lead structures that have not been optimized for in vivo action.

SUMMARY

The invention relates to a compound useful for enhancing efficacy of a therapeutic agent, a method for identifying such a compound, and a method of treating diseases including inflammation, graft rejection, infection, cancer, allergies, metabolic cardiovascular, pulmonary, dermatological, rheumatological and hepatic diseases. The invention further comprises compositions and formulations selected using the method and applications for same.

The invention provides for a method for identifying compounds that act as carriers or "transportophores" (i.e., a transport mediating molecule) that when combined, either directly or via a linker, to a wide variety of therapeutic agents, improves one or more of the following characteristics of the agent: ease of formulation, gastric stability, bioavailability, stability, disposition, elimination, half life, efficacy, safety, duration of action and selectivity.

In one aspect, this invention features a compound of the following formula (or referred to as T—L—C hereinafter):

wherein T is a transportophore, L is a bond or a linker having a molecular weight up to 240 dalton, C is a non-antibiotic therapeutic agent, and m is 1, 2, 3, 4, 5, 6, 7, or 8, in which the transportophore has an immune selectivity ratio of at least 2, the transportophore is covalently bonded to the non-antibiotic therapeutic agent via the bond or the linker, and the compound has an immune selectivity ratio of at least 2. Note that when there are more than one L or C moieties (i.e., m is greater than 1), the L moieties or the C moieties, independently, can be the same or different. The same rule applies to other similar situations.

The transportophore can be a metabolite, a natural product, a metabolite mimic, a metabolite derivative (e.g., a sugar, amino, or peptide derivative), a fatty acid, a bile acid, a vitamin, a nucleobase, an alcohol, or an organic acid or base, a portion of which resembles and is recognized as a substrate for transport protein(s). It can be an amphiphilic molecule having a pKa value of 6.5 to 9.5, or a cyclic or heterocyclic molecule (e.g., lactone, lactam, ether, cyclic acetal or hemiacetal). The cyclic or heterocyclic molecule can have an attached sugar. The cyclic or heterocyclic molecule can be a macrolactone or macroether, including a macrolactone or macroether having an attached sugar. The cyclic or heterocyclic molecule can also be a macrolide or ketolide having an amino sugar, including a macrolide having mono-, di-, or tri-basic groups (e.g., an amine). In some embodiments, the macrolide has no intrinsic antibacterial activity (inactive at 50 uM or higher concentrations when tested against Bacillus invitro see protocol) and a pKa value of less than 9.0 (e.g., 8.5, 8.0, 7.5, 7.0, or any number in between).

In some embodiments, the compound has the following formula (in which a bond, drawn without any attached groups, means a methyl group. The same rule applies to other similar situtations):

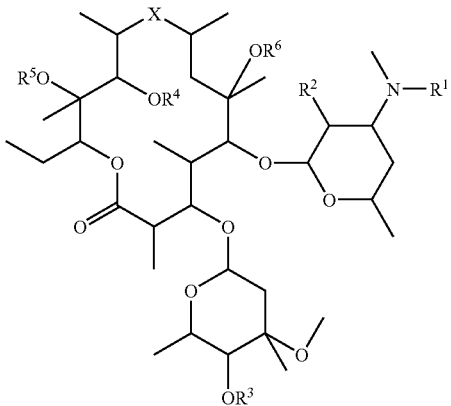

Wherein,
X=N($R^7$)—$CH_2$
$CH_2$—N($R^7$)
C(=O)
C(=N$OR^8$)
CH(O$R^9$)
CH(N$R^{10}R^{11}$)
C(=N$R^{12}$)
OC(=O)
C(=O)O
Y=independently,
  Linker (as defined below)
Z=C(=O)—
  CH($R^{16}$)
$R^1$=H
  $CH_3$
  ($C_2$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
  ($C_1$-$C_4$)alkyliden-N$R^{18}R^{19}$
  Y—$R^{13}$
  C(=O)—Y—$R^{15}$
  C(=O)—$R^{15}$
$R^2$=H
  (1',2'-cis)-OH
  (1',2'-trans)-OH
  (1',2'-cis)-O$R^{15}$
  (1',2'-trans)-O$R^{15}$
  (1',2'-cis)-SH
  (1',2'-cis)-S—Y—$R^{13}$
  or the $R^1$ and $R^2$ bearing atoms are connected via a —OC(=O)CH$R^{16}$— element
$R^3$=H
  C(=O)—Y—$R^{15}$
  C(=O)—$R^{15}$
$R^4$=H
  C(=O)—Y—$R^{15}$
  C(=O)—$R^{15}$
$R^5$=H
  or $R^4$, $R^5$ are connected by Z
$R^6$=H
  $CH_3$
$R^7$=H
  $CH_3$
  Y—$R^{13}$
  C(=O)—Y—$R^{15}$
  C(=O)—$R^{15}$
$R^8$=H
  Y—$R^{13}$
  $R^{13}$
  C(=O)—$R^{17}$
  ($C_1$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
  ($C_1$-$C_4$)alkyliden-N$R^{18}R^{19}$ wherein alkyl, alkenyl, alkynyl, aryl, and heteroaryl groups are optionally substituted by one to five substituents selected independently from halogen, ($C_1$-$C_4$)alkyl, ($C_1$-$C_4$)alkenyl, ($C_1$-$C_4$)alkynyl, ($C_3$-$C_7$)cycloalkyl, ($C_1$-$C_6$)heterocycloalkyl, ($C_6$-$C_{10}$)aryl, ($C_1$-$C_9$)heteroaryl, ($C_1$-$C_4$)alkoxy, hydroxy, nitro, cyano, azido, mercapto, —N$R^{18}R^{19}$, $R^{18}$C(=O)—, $R^{18}$C(=O)O—, $R^{18}$OC(=O)O—, $R^{18}$NHC(=O)—, $R^{18}$C(=O)NH—, $R^{18}R^{19}$NC(=O)— and $R^{18}$OC(=O)—

$R^9$=H
  ($C_1$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl wherein alkyl, alkenyl, alkynyl, aryl, and heteroaryl groups are optionally substituted by one to five substituents selected independently from halogen, ($C_1$-$C_4$)alkyl, ($C_1$-$C_4$)alkenyl, ($C_1$-$C_4$)alkynyl, ($C_3$-$C_7$)cycloalkyl, ($C_1$-$C_6$)heterocycloalkyl, ($C_6$-$C_{10}$)aryl, ($C_1$-$C_9$)heteroaryl, ($C_1$-$C_4$)alkoxy, hydroxy, nitro, cyano, azido, mercapto, —N$R^{18}R^{19}$, $R^{18}$C(=O)—, $R^{18}$C(=O)O—, $R^{18}$OC(=O)O—, $R^{18}$NHC(=O)—, $R^{18}$C(=O)NH—, $R^{18}$ $R^{19}$NC(=O)— and $R^{18}$OC(=O)—

$R^{10}$, $R^{11}$=independently H
  ($C_1$-$C_{10}$)alkyl ($C_1$-$C_{10}$)alkenyl
($C_1$-$C_{10}$)akynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl
($C_1$-$C_4$)alkyliden-$NR^{18}R^{19}$
or $R^{10}$=H and $R^{11}$=—Y—$R^{13}$
C(=O)—Y—$R^{15}$, —C(=O)—$R^{15}$
$R^{12}$=H
  ($C_1$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
  ($C_1$-$C_4$)alkyliden-$NR^{18}R^{19}$
  Y—$R^{13}$
$R^{13}$=$R^{15}$=independently, therapeutic agent
$R^{16}$=H
  $CH_3$
  ($C_2$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
  ($C_1$-$C_4$)alkyliden-$NR^{18}R^{19}$
Y—$R^{13}$,
$R^{17}$=O—$R^{20}$-aryl
  optionally substituted by —X'—Y-therapeutic agent, X'-therapeutic agent wherein X' is
    S
    O
    NH
$R^{18}$, $R^{19}$=independently H
  ($C_1$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
$R^{20}$=independently
  Halogen
  ($C_1$-$C_3$)alkyl
  $NO_2$
  CN
  $OCH_3$
  $N(CH_3)_2$
  $N_3$
  SH
  S($C_1$-$C_4$)alkyl In some other embodiments, the compound has the following formula:

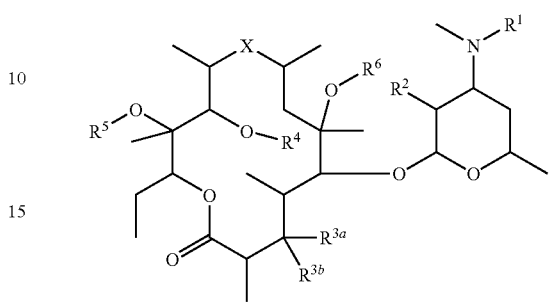

Wherein,
X=N($R^7$)—$CH_2$
  $CH_2$—N($R^7$)
  C(=O)
  C(=$NOR^8$)
  CH($OR^9$)
  CH($NR^{10}R^{11}$)
  C(=$NR^{12}$)
  OC(=O)
  C(=O)O
Y=independently, Linker (as defined below)
Z=C(=O)—
  CH($R^{16}$)—
$R^1$=H
  $CH_3$
  ($C_2$-$C_{10}$)alkyl
  ($C_1$-$C_{10}$)alkenyl
  ($C_1$-$C_{10}$)alkynyl
  ($C_1$-$C_8$)[($C_1$-$C_4$)alkoxy]alkyl
  ($C_1$-$C_8$)[($C_1$-$C_4$)alkoxy]alkenyl
  ($C_6$-$C_{10}$)aryl-($C_1$-$C_5$)alkyl
  ($C_2$-$C_9$)heteroaryl-($C_1$-$C_5$)alkyl
  ($C_1$-$C_4$)alkyliden-$NR^{18}R^{19}$
  Y—$R^{13}$
  C(=O)—Y—$R^{15}$
  C(=O)—$R^{15}$
  S(=O)$_k$($C_1$-$C_{10}$)alkyl
  S(=O)$_k$($C_1$-$C_{10}$)alkenyl
  S(=O)$_k$($C_1$-$C_{10}$)alkynyl
  S(=O)$_k$(C6-$C_{10}$)aryl
  S(=O)$_k$($C_2$-$C_9$)heteroaryl
  S(=O)$_k$—Y—$R^{15}$
  S(=O)$_k$—$R^{15}$ wherein k is 0, 1 or 2, and alkyl, alkenyl, alkynyl, cycloalkyl, heterocycloalkyl, aryl and heteroaryl can optionally be substituted by one to three halogen, cyano, hydroxy, ($C_1$-$C_4$) alkyloxy, nitro, ($C_1$-$C_6$)alkyl, ($C_1$-$C_6$)alkenyl, ($C_1$-$C_6$)alkynyl, ($C_3$-$C_7$)cycloalkyl, ($C_1$-$C_6$)heterocycloalkyl, ($C_6$-$C_{10}$) aryl, ($C_1$-$C_9$)heteroaryl, $NR^{18}R^{19}$, $R^{18}$C(=O) O—, $R^{18}$OC(=O)—, $R^{18}$C(=O)NH—, $R^{18}$NHC(=O)—, $R^{18}R^{19}$NC(=O)— and $R^{18}$OC(=O)—O—
$R^2$=H
  (1',2'-cis)-OH
  (1',2'-trans)-OH
  (1',2'-cis)-$OR^{15}$
  (1',2'-trans)-$OR^{15}$
  (1',2'-cis)-SH (1',2'-cis)-S—Y—R$^{13}$
or the R$^1$ and R$^2$ bearing atoms are connected via a —OC(=O)CHR$^{16}$-element
R$^{3a}$, R$^{3b}$=independently H
   R$^1$
   OH
   OR$^{11}$
   NR$^{10}$R$^{11}$
or R$^{3a}$=R$^{3b}$=(=O),
   (=NR$^1$)
   O(CH$_2$)$_k$O— wherein k is 2 or 3
R$^4$=H
   C(=O)—Y—R$^{15}$
   C(=O)—R$^{15}$
R$^5$=H
or R$^4$, R$^5$ are connected by —Z—
R$^6$=H
   CH$_3$
R$^7$=H
   CH$_3$
   Y—R$^{13}$
   C(=O)—Y—R$^{15}$
   C(=O)—R$^{15}$
R$^8$=H
   Y—R$^{13}$
   C(=O)—R$^{17}$
R$^9$=H
   (C$_1$-C$_{10}$)alkyl
   (C$_1$-C$_{10}$)alkenyl
   (C$_1$-C$_{10}$)alkynyl
   (C$_1$-C$_8$)[(C$_1$-C$_4$)alkoxy]alkyl
   (C$_1$-C$_8$)[(C$_1$-C$_4$)alkoxy]alkenyl
   (C$_6$-C$_{10}$)aryl-(C$_1$-C$_5$)alkyl
   (C$_2$-C$_9$)heteroaryl-(C$_1$-C$_5$)alkyl
R$^{10}$, R$^{11}$=independently H
   (C$_1$-C$_{10}$)alkyl
   (C$_1$-C$_{10}$)alkenyl
   (C$_1$-C$_{10}$)akynyl
   (C$_3$-C$_{10}$)cycloalkyl
   (C$_1$-C$_9$)heterocycloalkyl
   (C$_6$-C$_{10}$)aryl
   (C$_2$-C$_9$)heteroaryl wherein alkyl, alkenyl, alkynyl, cycloalkyl, heterocycloalkyl, aryl, heteroaryl are optionally substituted by one to three halogen, cyano, hydroxy, (C$_1$-C$_4$)alkyloxy, nitro, (C$_1$-C$_6$)alkyl, (C$_1$-C$_6$)alkenyl, (C$_1$-C$_6$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, NR$^{18}$R$^{19}$, R$^{18}$C(=O)—, R$^{18}$C(=O)O—, R$^{18}$OC(=O)—, R$^{18}$C(=O)NH—, R$^{18}$NHC(=O)—, R$^{18}$R$^{19}$NC(=O)— and R$^{18}$OC(=O)—O—
   or R$_{10}$=H and
   R$^{11}$=Y—R$^{13}$
   C(=O)—Y—R$^{15}$
   C(=O)—R$^{15}$
   S(=O)$_k$(C$_1$-C$_{10}$)alkyl
   S(=O)$_k$(C$_1$-C$_{10}$)alkenyl
   S(=O)$_k$(C$_1$-C$_{10}$)alkynyl
   S(=O)$_k$(C6-C$_{10}$)aryl
   S(=O)$_k$(C$_2$-C$_9$)heteroaryl
   S(=O)$_k$—Y—R$^{15}$
   S(=O)$_k$—R$^{15}$ wherein k is 0, 1 or 2 and alkyl, alkenyl, alkynyl, cycloalkyl, heterocycloalkyl, aryl and heteroaryl can be substituted as defined above.

R$^{12}$=H
   (C$_1$-C$_{10}$)alkyl
   (C$_1$-C$_{10}$)alkenyl
   (C$_1$-C$_{10}$)alkynyl
   (C$_1$-C$_8$)[(C$_1$-C$_4$)alkoxy]alkyl
   (C$_1$-C$_8$)[(C$_1$-C$_4$)alkoxy]alkenyl
   (C$_6$-C$_{10}$)aryl-(C$_1$-C$_5$)alkyl
   (C$_2$-C$_9$)heteroaryl-(C$_1$-C$_5$)alkyl
   (C$_1$-C$_4$)alkyliden-NR$^{18}$R$^{19}$
   Y—R$^{13}$
R$^{13}$=R$^{15}$=independently therapeutic agent
R$^{16}$=H
   CH$_3$
   (C$_2$-C$_{10}$)alkyl
   (C$_1$-C$_{10}$)alkenyl
   (C$_1$-C$_{10}$)alkynyl
   (C$_1$-C$_8$)[(C$_1$-C$_4$)alkoxy]alkyl
   (C$_1$-C$_8$)[(C$_1$-C$_4$)alkoxy]alkenyl
   (C$_6$-C$_{10}$)aryl-(C$_1$-C$_5$)alkyl
   (C$_2$-C$_9$)heteroaryl-(C$_1$-C$_5$)alkyl
   (C$_1$-C$_4$)alkyliden-NR$^{18}$R$^{19}$
   Y—R$^{13}$
R$^{17}$=O—R$^{20}$-aryl
   optionally substituted by —X'—Y-therapeutic agent, X'-therapeutic agent wherein X' is
   S, O, NH
R$^{18}$, R$^{19}$=independently H
   (C$_1$-C$_{10}$)alkyl
   (C$_1$-C$_{10}$)alkenyl
   (C$_1$-C$_{10}$)alkynyl
   (C$_1$-C$_8$)[(C$_1$-C$_4$)alkoxy]alkyl
   (C$_1$-C$_8$)[(C$_1$-C$_4$)alkoxy]alkenyl
   (C$_6$-C$_{10}$)aryl-(C$_1$-C$_5$)alkyl
   (C$_2$-C$_9$)heteroaryl-(C$_1$-C$_5$)alkyl
R$^{20}$=independently,
   Halogen
   (C$_1$-C$_3$)alkyl
   NO$_2$
   CN
   OCH$_3$
   N(CH$_3$)$_2$
   N$_3$
   SH
   S(C$_1$-C$_4$)alkyl In still some other embodiments, the compound has the following formula:

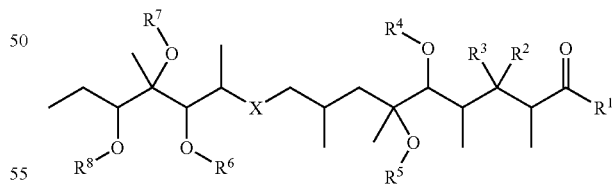

Wherein,
X=N(R$^9$)—CH$_2$
   CH$_2$—N(R$^9$)
   C(=O)
   C(=NOR$^{10}$)
   C(OR$^{11}$)H
   CH(NR$^{12}$R$^{13}$)
   C(=NR$^{14}$)
   OC(=O)
   C(=O)O Y=independently, Linker (as defined below)
$R^1=OR^{17}$
   $NR^{17}R^{18}$,
or $R^1$ is connected to the oxygen bearing $R^4$ or $R^5$ forming a lactone or is connected to a suitable substituent in $R^2$ forming a lactone or lactam.
$R^2$=O-2-cladinosyl

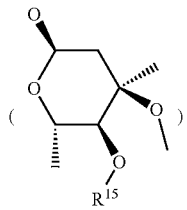

H
X', wherein X'=halogen
azido
nitro
cyano
$OR^{17}$
$OR^{22}$
$NR^{17}R^{18}$
$SR^{17}$ $(C_1-C_6)$alkyl
$(C_1-C_6)$alkenyl
$(C_1-C_6)$alkynyl
$(C_3-C_{10})$cycloalkyl
$(C_1-C_9)$heterocycloalkyl
$(C_6-C_{10})$aryl
$(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N—$, $R^{20}C(=O)—$, $R^{20}C(=O)O—$, $R^{20}OC(=O)—$, $R^{20}NHC(=O)—$, $R^{20}C(=O)NH—$, $R^{20}R^{21}NC(=O)—$, and $R^{20}OC(=O)O—$, —Y-therapeutic agent or -therapeutic agent $R^3$=H
   $(C_1-C_6)$alkyl
   $(C_1-C_6)$alkenyl
   $(C_1-C_6)$alkynyl
   $(C_3-C_{10})$cycloalkyl
   $(C_1-C_9)$heterocycloalkyl
   $(C_6-C_{10})$aryl
   $(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, $R^{20}R^{21}N—$ $R^4$=O-2-desosaminyl

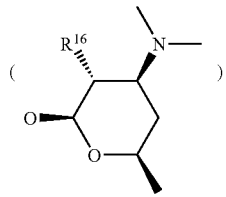

H
$C(=O)R^{17}$
Y-therapeutic agent
therapeutic agent
$S(=O)_2R^{17}$ providing $R^{17}$ is not hydrogen
$C(=O)NR^{17}R^{18}$ $(C_1-C_6)$alkyl
$(C_1-C_6)$alkenyl
$(C_1-C_6)$alkynyl
$(C_3-C_{10})$cycloalkyl
$(C_1-C_9)$heterocycloalkyl
$(C_6-C_{10})$aryl
$(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N—$, $R^{20}C(=O)—$, $R^{20}C(=O)O—$, $R^{20}OC(=O)—$, $R^{20}NHC(=O)—$, $R^{20}C(=O)NH—$, $R^{20}R^{21}NC(=O)—$, and $R^{20}OC(=O)O—$, —Y-therapeutic agent or -therapeutic agent
   or $R^4$ is connected to a suitable $R^2$ containing a N or a O by $—C(=O)$, $S(=O)_n$ wherein n=1 or 2, $—CR^{20}R^{17}—$, $CR^{20}(—Y$-therapeutic agent)-, $—CR^{20}(-$therapeutic agent)-forming in dependence of $R^2$ a 6 or 7-membered ring $R^5=R^{20}$
   $C(=O)R^{20}$
or $R^4$, $R^5$ are connected by $C(=O)$, $S(=O)_n$ wherein n=1 or 2, $—CR^{20}R^{17}—$, $CR^{20}(—Y$-therapeutic agent)-, $—CR^{20}(-$therapeutic agent)-

$R^6$, $R^8$=independently H
   $(C_1-C_6)$alkyl
   $(C_1-C_6)$alkenyl
   $(C_1-C_6)$alkynyl
   $(C_3-C_{10})$cycloalkyl
   $(C_1-C_9)$heterocycloalkyl
   $(C_6-C_{10})$aryl
   $(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N—$, $R^{20}C(=O)—$, $R^{20}C(=O)O—$, $R^{20}OC(=O)—$, $R^{20}NHC(=O)—$, $R^{20}C(=O)NH—$, $R^{20}R^{21}NC(=O)—$, and $R^{20}OC(=O)O—$, —Y-therapeutic agent or -therapeutic agent,
   or $R^6$, $R^8$=independently $—C(=O)R^{17}$, —Y-therapeutic agent, -therapeutic agent, $—S(=O)_2R^{17}$ providing $R^{17}$ is not hydrogen, $—C(=O)NR^{17}R^{18}$ $R^7$=H
- $(C_1-C_6)$alkyl
- $(C_1-C_6)$alkenyl
- $(C_1-C_6)$alkynyl
- $(C_3-C_{10})$cycloalkyl
- $(C_1-C_9)$heterocycloalkyl
- $(C_6-C_{10})$aryl
- $(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, and $R^{20}OC(=O)O-$, —Y-therapeutic agent or -therapeutic agent or two of each $R^6$, $R^7$, $R^8$ are connected by $-C(=O)$, $S(=O)_n$ wherein n=1 or 2, $-CR^{20}R^{17}-$, $CR^{20}(-Y-$therapeutic agent)-, $-CR^{20}(-$therapeutic agent)-

$R^9$=H
- $CH_3$
- Y-therapeutic agent
- therapeutic agent
- $(C_1-C_6)$alkyl
- $(C_1-C_6)$alkenyl
- $(C_1-C_6)$alkynyl, wherein alkyl, alkenyl, alkynyl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}OR^{21}NC(=O)-$, and $R^{20}OC(=O)O-$, —Y-therapeutic agent or -therapeutic agent $R^{10}$=C(=O)-aryl
- therapeutic agent
- H
- $(C_1-C_6)$alkyl
- $(C_1-C_6)$alkenyl
- $(C_1-C_6)$alkynyl, wherein alkyl, alkenyl, alkynyl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^2C(=O)NH-$, $R^{20}R^{21}NC(=O)-$, and $R^{20}OC(=O)O-$, —Y-therapeutic agent or -therapeutic agent $R^{11}$=H
- $(C_1-C_6)$alkyl
- $(C_1-C_6)$alkenyl
- $(C_1-C_6)$alkynyl, wherein alkyl, alkenyl, alkynyl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}OR^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, $R^{20}OC(=O)O-$, —Y-therapeutic agent or -therapeutic agent, or $R^{11}$=—Y-therapeutic agent, -therapeutic agent, $-C(=O)R^{17}$ $R^{12}$, $R^{13}$=independently H
- $(C_1-C_6)$alkyl
- $(C_1-C_6)$alkenyl
- $(C_1-C_6)$alkynyl
- $(C_3-C_{10})$cycloalkyl
- $(C_1-C_9)$heterocycloalkyl
- $(C_6-C_{10})$aryl
- $(C_1-C_9)$heteroaryl, wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, $R^{20}OC(=O)O-$, —Y-therapeutic agent or -therapeutic agent, or $R^{12}$, $R^{13}$=independently $-C(=O)R^{17}$, —Y-therapeutic agent, -therapeutic agent, $-S(=O)_2R^{17}$ providing $R^{17}$ is not hydrogen, $-C(=O)NR^{17}R^{18}$ $R^{14}$=independently
- therapeutic agent
- H
- $(C_1-C_6)$alkyl
- $(C_1-C_6)$alkenyl
- $(C_1-C_6)$alkynyl
- $(C_3-C_{10})$cycloalkyl
- $(C_1-C_9)$heterocycloalkyl
- $(C_6-C_{10})$aryl
- $(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, $R^{20}OC(=O)O-$, —Y-therapeutic agent or -therapeutic agent $R^{15}$=independently
- H
- $C(=O)R^{17}$
- Y-therapeutic agent
- therapeutic agent
- $S(=O)_2R^{17}$ providing $R^{17}$ is not hydrogen
- $C(=O)NR^{17}R^{18}$
- $(C_1-C_6)$alkyl
- $(C_1-C_6)$alkenyl
- $(C_1-C_6)$alkynyl
- $(C_3-C_{10})$cycloalkyl
- $(C_1-C_9)$heterocycloalkyl
- $(C_6-C_{10})$aryl
- $(C_1-C_9)$heteroaryl, wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, and $R^{20}OC(=O)O-$, —Y-therapeutic agent or -therapeutic agent $R^{16}$=H
  $OR^{17}$
  $OR^{22}$
$R^{17}$, $R^{18}$=independently H
  $(C_1-C_6)$alkyl
  $(C_1-C_6)$alkenyl
  $(C_1-C_6)$alkynyl
  $(C_3-C_{10})$cycloalkyl
  $(C_1-C_9)$heterocycloalkyl
  $(C_6-C_{10})$aryl
  $(C_1-C_9)$heteroaryl wherein alkyl, alkenyl, alkynyl, cycloalkyl, heterocycloalkyl, aryl, heteroaryl groups are optionally substituted by one to five substituents selected independently from halogen, $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, and $R^{20}OC(=O)O-$, —Y-therapeutic agent or -therapeutic agent or provided that connected to a nitrogen, $R^{17}$, $R^{18}$ may form a cyclic structure of 4 to 7 members (including the nitrogen). $R^{17}$ and $R^{18}$ then can represent a fragment from the type of $-[C(AB)]_m-\Xi_n-[C(DE)]_o-\Psi_p-[C(GJ)]_q$ wherein m, n, o, p and q independently are 0, 1, 2, 3, 4, 5, or 6, $\Xi$ and $\Psi$ independently are —O—, —S—, —NK— and A, B, D, E, G, J, and K independently are hydrogen, $(C_1-C_4)$ alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $R^{20}R^{21}N-$, $R^{20}C(=O)-$, $R^{20}C(=O)O-$, $R^{20}OC(=O)-$, $R^{20}NHC(=O)-$, $R^{20}C(=O)NH-$, $R^{20}R^{21}NC(=O)-$, and $R^{20}OC(=O)O-$ $R^{20}$, $R^{21}$=independently H
  $(C_1-C_6)$alkyl
$R^{22}$=independently
  $C(=O)R^{17}$
  Y-therapeutic agent
  therapeutic agent
  $S(=O)_2R^{17}$ providing $R^{17}$ is not hydrogen, $-C(=O)NR^{17}R^{18}$.

In further embodiments, the compound has the following formula:

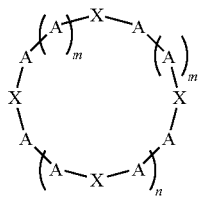

Wherein
m=independently, 0, 1, 2, 3
n=0-7
X=independently
  O
  S
  Se
  $NR^1$
  $PR^1$ with the proviso, that at least one $X=-NR^1-$
A=independently
  $CH_2$
  $CHR^2$
  $CR^2R^3$
  $C(=O)$ with the proviso, that at least one $X=-NR^1-$ is not an amide $R^1$=independently,
  H
  $(C_1-C_{10})$alkyl optionally substituted by fluoro, cyano, $R^4$, $R^4O_2C$,
    $R^4C(=O)NH$ and $R^4S(=O)_k$ wherein k is 0, 1 or 2
  $R^4C(=O)$, $R^4S(=O)_k$ wherein k is 0, 1 or 2

$R^2$, R=independently $NH_2$
  $NHR^1$
  $NR^1R^5$
  OH,
  $OR^4$
  $R^4C(=O)$ $(C_1-C_6)$alkyl
  $(C_2-C_{12})$alkenyl
  $(C_2-C_{12})$alkynyl
  $(C_3-C_{10})$cycloalkyl$(C_1-C_6)$alkyl
  $(C_2-C_9)$heterocycloalkyl$(C_1-C_6)$alkyl
  $(C_6-C_{10})$aryl$(C_1-C_6)$alkyl
  $(C_2-C_9)$heteroaryl$(C_1-C_6)$alkyl, wherein the alkyl, alkenyl, alkynyl, cycloalkyl, heterocycloalkyl, aryl, and heteroaryl groups are optionally substituted by one to three halo, $(C_1-C_4)$alkoxy, hydroxy, nitro, cyano, $-C(=O)-OR^8$, $-C(=O)N(H)R^8$, $(C_6-C_{10})$aryl, $(C_2-C_9)$heteroaryl, $N^*R^5R^6R^7$ wherein * is no or a positive charge, one or two of $R^2$, $R^3$ can be a directly coupled therapeutic agent $R^4$=independently
  $NH_2$
  $NHR^9$
  $NR^9R^5$
  OH
  $OR^9$
  $(C_1-C_6)$alkyl
  $(C_2-C_{12})$alkenyl
  $(C_2-C_{12})$alkynyl
  $(C_3-C_{10})$cycloalkyl$(C_1-C_6)$alkyl
  $(C_2-C_9)$heterocycloalkyl$(C_1-C_6)$alkyl
  $(C_6-C_{10})$aryl$(C_1-C_6)$alkyl
  $(C_2-C_9)$heteroaryl$(C_1-C_6)$alkyl, wherein the alkyl, alkenyl, alkynyl, cycloalkyl, heterocycloalkyl, aryl, and heteroaryl groups are optionally substituted by one to three halo, $(C_1-C_4)$alkoxy, hydroxy, nitro, cyano, $R^8$, $-C(=O)-OR^8$, $-C(=O)N(H)R^8$, $(C_6-C_{10})$aryl, $(C_2-C_9)$heteroaryl, $N^*R^5R^6R^7$ wherein * is no or a positive charge, or therapeutic agent $R^5$, $R^6$=independently H
  $(C_1-C_6)$, optionally substituted by hydroxy
  $(C_6-C_{10})$aryl
  $(C_2-C_9)$heteroaryl
$R^7$=independently
  lone electron pair
  $CH_3$
  $C_2H_5$
  $C_3H_7$
  $CH_2-C_6H_5$
$R^8$=independently,
  therapeutic agent $R^9$=independently,
 ($C_1$-$C_6$) alkyl
 ($C_2$-$C_{12}$)alkenyl
 ($C_2$-$C_{12}$)alkynyl
 ($C_3$-$C_{10}$)cycloalkyl($C_1$-$C_6$)alkyl
 ($C_2$-$C_9$)heterocycloalkyl($C_1$-$C_6$)alkyl
 ($C_6$-$C_{10}$)aryl($C_1$-$C_6$)alkyl or
 ($C_2$-$C_9$)heteroaryl($C_1$-$C_6$)alkyl, wherein the alkyl, alkenyl, alkynyl, cycloalkyl, heterocycloalkyl, aryl, and heteroaryl groups are optionally substituted by one to three halo, ($C_1$-$C_4$)alkoxy, hydroxy, nitro, cyano, $R^8$, —C(=O)—$OR^8$, —C(=O)N(H)$R^8$, ($C_6$-$C_{10}$) aryl, ($C_2$-$C_9$)heteroaryl, N*$R^5R^6R^7$ wherein * is no or a positive charge, or therapeutic agent.

Preferred molecules can be compounds that are recognized by a transport enzyme in the membrane of the cell of the tissue that is to target. This can be a molecule that fulfills the structural requirements in order to be recognized by an oligopeptide transporter.

Compounds recognized by transport enzymes can be identified by performing a transport assay with the compound in question in cells expressing the transport protein in question, and comparing the level of compound accumulation with those from parallel uptake assays performed using cells which do not express the target transport protein.

According to well known models these structures may be as exemplified in the following sketches:

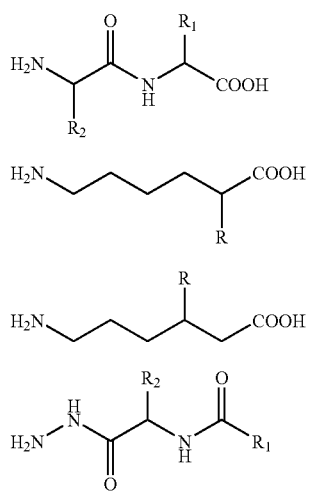

In these examples R (including $R_1$ and $R_2$) may represent a chemical residue that will modify the recognition by the transporting enzyme or at least not inhibit it. R may be comprised of the therapeutic agent that is to be delivered or the pharmaceutical entity is for example an amino acid itself as in example A.

Necessary for transport through an oligopeptide transporter seems to be a basic group spaced 4 or 5 bonds from an hydrogen bond accepting group like preferably carboxylate (example A-C) or less preferred amide (example D).

Example A: $R_1$ and $R_2$ are hydrogen or lower alkyl, branched or linear from $C_1$ to $C_5$, or benzyl or p-hydroxy benzyl, or hydroxy or mercapto methyl, or any group responsible for the desired pharmacological effect.

Example B: R can be the moiety responsible for the pharmacological effect, or the pharmacologically relevant group linked on the carbon chain by a chemical linker like an amide (amido-R=NH(C=O)—R' (R'=pharmacologically relevant group)).

Example C: R can be the moiety responsible for the pharmacological effect, or the pharmacologically relevant group linked on the carbon chain by a chemical linker like an amide (amido-R=NH(C=O)—R' (R'=pharmacologically relevant group)).

Example D: R2 can be hydrogen or lower alkyl, branched or linear from C1 to C5, or benzyl or p-hydroxy benzyl, or hydroxy or mercapto methyl, while R1 consists of the pharmacologically relevant therapeutic agent. Preferably the therapeutic agent would contain a carboxylic acid that by linking to the amino function of an amino acid hydrazide would obtain the general structure of example D.

Therapeutic agents and Transportophores can be directly connected or via a linking element. This element typically is a bifunctional molecule of low molecular mass, which can react subsequently with the therapeutic agent and the transportophore. Ideally the therapeutic agent can be released from this linker under physiological conditions. This may be achieved oxidatively (i.e. by action of a cytochrome C), reductively (i.e. by action of NADH), hydrolytically (i.e. by action of a protease), or initiated by radicals (i.e. by the action of superoxide radicals). The mechanisms of therapeutic agent release are not limited to the above examples.

Linkers have the following formula:

Where can be:
$F^1$, $F^2$=independently a functional group, suitable to react with a counterpart in the therapeutic agent or in the transportophore. $F^1$ and $F^2$ are, but are not limited to
 $X^1$ wherein $X^1$ is a halogen atom or a sulfonate ester or another suitable leaving group;
 C(=O)$X^2$ wherein $X^2$ is Cl, Br or I,
 CHO;
 C(=O)$OR^a$ wherein $R^a$ is ($C_1$-$C_4$)alkyl or aryl, optionally substituted by 1-5 halogen atoms;
 C(=O)OC(=O)$OR^b$ wherein $R^b$ is ($C_1$-$C_5$)alkyl or ($C_1$-$C_5$)alkenyl;
 OH;
 $NHR^c$ wherein $R^c$ is H, ($C_1$-$C_4$)alkyl;
 $NCX^3$ wherein $X^3$ is S or O;
 C(=O)CR=CHR', wherein R and R' are independently —H, —$CH_3$, —Cl, —Br, —F, —O($C_1$-$C_4$)alkyl, —C(=O)O($C_1$-$C_4$)alkyl, —$NO_2$, —S(=O)$_k$(O)$_l$($C_1$-$C_4$) alkyl wherein k is 0, 1 or 2 and 1 is 0 or 1, $SiR^1R^2R^3$ wherein $R^1$, $R^2$ and $R^3$ independently are ($C_1$-$C_4$)alkyl;
 $SX^4$ wherein $X^4$ is —H, —Cl, —$S_k$($C_1$-$C_4$)alkyl, $S_k$($C_6$-$C_{10}$)aryl wherein k is 1 or 2.

$F^1$ and $F^2$ can be connected to form a cyclic anhydride or di- or trisulfide.

M is a spacing element which is, but is not limited to
 ($C_1$-$C_8$)alkyl,
 ($C_1$-$C_8$)alkenyl,
 ($C_1$-$C_8$)alkynyl,
 ($C_3$-$C_{10}$)cycloalkyl,
 ($C_6$-$C_{10}$)aryl,
 ($C_2$-$C_9$)heteroalkyl,
 ($C_2$-$C_9$)heteroaryl.

Alkyl-, alkenyl, alkynyl, cycloalkyl, aryl or heteroaryl spacing elements are optionally substituted by ($C_1$-$C_6$)alkyl, 1-4 halogens, ($C_1$-$C_4$)alkoxy, ($C_1$-$C_4$)alkoxycarbonyl, hydroxy, amino, ($C_1$-$C_4$)alkylamino, ($C_1$-$C_4$)dialkylamino, ($C_3$-$C_{10}$)cycloalkyl, ($C_1$-$C_6$)alkylcarbonyloxy, ($C_1$-$C_6$)alkylcarbonylamido, ($C_1$-$C_4$)alkylamidocarbonyl, ($C_1$-$C_4$)dialkylamidocarbonyl, nitro, cyano, ($C_1$-$C_4$)alkylimino, mercapto and ($C_1$-$C_4$)alkylmercapto functions.

TABLE 1

Non-limiting examples of Linkers useful in the synthesis of T-L-C molecules.*

| Donor linking function | Recipient linking function | | |
|---|---|---|---|
| | COOH | NH2 | OH |
| COOH | Ethylendiamine, Glycol, (2-Aminoethyl)-(2-hydroxyethyl)amino | N-Methoxycarbonyl-4-hydroxyproline, Glycolic acid, β-Alanin, β-hydroxy propanoic acid | N-Methoxycarbonyl-4-hydroxyproline, Glycolic acid, β-Alanin, β-hydroxy propanoic acid |
| NH2 | N-Methoxycarbonyl-4-hydroxyproline, Glycolic acid, β-Alanin, β-hydroxy propanoic acid | Ethylendiamine, 2,2-Dimethylsuccinic acid, Succinic acid, Glutaric acid, 2,4-Dimethylglutaric acid, Methyl dicarboxymethylamino | 2,2-Dimethylsuccinic acid, Succinic acid, Glutaric acid, 2,4-Dimethylglutaric acid, Methyl dicarboxymethylamin, 2-Aminoethyl-2-hydroxyethylamino |
| OH | N-Methoxycarbonyl-4-hydroxyproline, Glycolic acid, β-Alanin, β-hydroxy propanoic acid | 2,2-Dimethylsuccinic acid, Succinic acid, Glutaric acid, 2,4-Dimethylglutaric acid, Methyl dicarboxymethylamin, 2-Aminoethyl-2-hydroxyethylamino | β-Hydroxy propanoic acid, 2,2-Dimethylsuccinic acid, Succinic acid, Glutaric acid, 2,4-Dimethylglutaric acid, Methyl dicarboxymethylamino |

*The donor linking function in vertical refers to a functional group on T; the recipient linking function in horizonal refers to a functional group on L; and the chemical groups in the boxes are the linkers (L).

The non-antibiotic therapeutic agent can be an anti-inflammatory agent, an anti-infectious agent (including anti-virals), an anti-cancer agent, an allergy-suppressive agent, an immune-suppressant agent, an agent for treating a hematopoietic disorder, a lipid lowering agent, an agent for treating a lysosomal storage disorder, a sterol synthesis modifying agent, agents active on protozoa, or an agent for treating a metabolic disease.

As used herein, an "immune selectivity ratio" is the ratio of the concentration of a compound in immune cells (e.g., neutrophils, monocytes, and lymphocytes) to the concentration of the compound in erythrocytic cells after the compound has been incubated in a mixture of blood cells including erythrocytes. A protocol of determining the immune selectivity ratio is described in Example 1.

A "therapeutic agent," as used herein, is a molecule with pharmacological activity (e.g., a therapeutic agent, medicine, medicament, or active agent), a disease modification agent, or any other molecule that can be covalently attached to a transportophore via a bond or a linker which may have a desirable mode of action in immune or target cells. A therapeutic agent may be released from a compound described above in response to the enzyme activity or the physicochemical environment of the targeted cells. Thus, the therapeutic agent is selectively accumulated in a cell due to specific characteristics of the cell membranes, specific expression of membrane proteins, specific conditions within the cell, notably to expression of specific proteins such as granule proteins, binding sites in the cytoplasm, or other membrane bound or soluble proteins, and is thus trapped in the cell and therefore exhibits an enhanced or desired activity therein.

An "amphiphilic molecule," as used herein, is a molecule having a hydrophilic (polar) and hydrophobic (non-polar) functional groups (e.g., atoms) or a combination of groups (or atoms). The pKa of this molecule is in the range of 6.5 to 9.5.

The term "cyclic" refers to a hydrocarbon cyclic ring including fully saturated, partially saturated, and unsaturated mono-, bi-, and tri-cyclic rings having 4 to 34 ring atoms, preferably, 7 to 10, or 10 to 15 ring atoms. The term "heterocyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms having one or more heteroatoms, such as S, O, or N in each ring.

The term "sugar" refers to a mono-, di-, or tri-saccharide including deoxy-, thio-, and amino-saccharides. Examples of sugar include, but are not limited to, furanose and pyranose.

The terms "halogen" and "halo" refer to radicals of fluorine, chlorine, bromine or iodine.

The term "macrolactone" refers to a large lactone ring (i.e., cyclic ester) having at least 10 (e.g., 10 to 25) ring atoms.

The term "macrocyclic ether" refers to an ether having at least 10 (e.g., 10 to 25) ring atoms.

The term "macrolide" refers to a chemical compound characterized by a large lactone ring (having at least 10, e.g., 10 to 25 ring atoms) containing one or more keto and hydroxyl groups, or to any of a large group of antibacterial antibiotics containing a large lactone ring linked glycosidically to one or more sugars; they are produced by certain species of Streptomyces and inhibit protein synthesis by binding to the 50S subunits of 70S ribosomes. Examples include erythromycin, azithromycin, and clarithromycin.

The term "ketolide" refers to a chemical compound characterized by a large lactone ring (having at least 10 ring atoms) containing one or more keto groups.

The term "alkyl" (or "alkenyl" or "alkynyl") refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. Alkenyl groups and alkynyl groups have one or more double or triple carbon-carbon bonds, respectively, in the chain.

The term "aryl" refers to a hydrocarbon ring system (mono-cyclic or bi-cyclic) having the indicated number of carbon atoms and at least one aromatic ring. Examples of aryl moieties include, but are not limited to, phenyl, naphthyl, and pyrenyl.

The term "heteroaryl" refers to a ring system (mono-cyclic or bi-cyclic) having the indicated number of ring atoms including carbon atoms and at least one aromatic ring. The ring system includes at least one heteroatom such as O, N, or S (e.g., between 1 and 4 heteroatoms, inclusive, per ring) as part of the ring system. Examples of heteroaryl moieties include, but are not limited to, pyridyl, furyl or furanyl, imidazolyl, benzimidazolyl, pyrimidinyl, thiophenyl or thienyl, quinolinyl, indolyl, and thiazolyl.

The term "alkoxy" refers to an —O-alkyl radical.

The term "cycloalkyl" refers to a nonaromatic hydrocarbon ring system (mono-cyclic or bi-cyclic), containing the indicated number of carbon atoms.

The term "heterocycloalkyl" refers to a nonaromatic ring system (mono-cyclic or bi-cyclic), containing the indicated number of ring atoms including carbon atoms and at least one heteroatom such as O, N, or S (e.g., between 1 and 4 heteroatoms, inclusive, per ring) as part of the ring system.

"Alkyliden" is a bivalent alkyl group.

"Aryliden" is a bivalent aryl group.

"Erythrocytic cell" is a mature red blood cell that normally does not have a nucleus: it is a very small, circular disk with both faces concave, and contains hemoglobin, which carries oxygen to the body tissues.

The compounds described above include the compounds themselves, as well as their salts, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Further, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

In another aspect, this invention features a method for treating an inflammatory disorder. The method includes administering to a subject in need thereof an effective amount of a compound described above, wherein the compound contains a non-antibiotic therapeutic agent that is an anti-inflammatory agent. Optionally, the method includes co-usage with other anti-inflammatory agents or therapeutic agents. The method is able to improve therapy by concentrating a compound preferentially in immune cells including neutrophils, monocytes, eosinophils, macrophage, alveolar macrophage, B and T-lymphocytes, NK cells, giant cells, Kupfer cells, glial cells, and similar target cells using a variety of means of concentrative compound uptake common to such cells. As such, the invention is advantageous in that selective concentration of compounds conforming to the definition of "therapeutic agent" above, can improve therapy and that, for the purposes of illustration only, concentration of agents in immune cells can confer improved characteristics on compounds with suitable modes of action for the treatment of inflammatory diseases.

In another aspect, the invention features a means of improving the action of a compound in vivo by reducing its exposure to the action of detoxification enzymes. Such reduced exposure is a result of the structure of the conjugate molecule causing it to be differently retained in the cells and organs of the organism and thus reducing or limiting the amount of material in a given metabolic compartment.

In another aspect, the invention provides for means to improve the action of a compound through improved retention in the cells and tissues of the organism such that it is less efficiently eliminated by the normal processes of circulation and filtration. Such avoidance of elimination is, at least in part, a consequence of efficient uptake into cells resulting in reduced concentrations of the drug being available from plasma.

In another aspect, the invention provides for a means of improving the action of a drug by assisting its uptake from the intestine through the overall effects on membrane permeability of the compound that are associated with the invention. Uptake from oral administration is a means of providing sustained exposure to the compound from the parts of the intestine to which it is permeable. Oral availability is not a property of all compounds.

This invention also features a method of treating a disease (e.g., an infectious disease including viral, fungal, or parasitic diseases, cancer, allergy, metabolic, cardiovascular, pulmonary, dermatological, rheumatological or immune disease). The method comprises administering to a subject in need thereof an effective amount of a compound described above, wherein the compound contains a non-antibiotic therapeutic agent (e.g., an anti-infectious agent, an anti-cancer agent, an agent for treating a hematopoietic disorder, an agent for treating a lysosomal storage disorder, an allergy-suppressive agent, a lipid lowering agent, a sterol synthesis modifying agent, agents active on protozoa or an immune-suppressant agent). Optionally, the method includes co-usage with other therapeutic agents. As described above, the method provides for means to improve therapy by concentrating a compound preferentially in any of the myeloid, hepatic, respiratory, epithelial, endothelial, other target and immune cells. Therefore, the invention is advantageous in that selective concentration of compounds conforming to the definition of "therapeutic agent" above, via the methods described, can improve therapy and that, for the purposes of illustration only, concentration of agents in immune cells can confer improved characteristics on compounds with suitable modes of action for the treatment of diseases of infectious, allergic, autoimmune, transplant, traumatic or neoplastic origin or association.

The present invention also features a pharmaceutical composition including at least one compound of this invention and a pharmaceutically acceptable carrier. Optionally, the pharmaceutical composition includes one or more other therapeutic agents.

This invention further features a method for making any of the compounds described above. The method includes taking any intermediate compound delineated herein, reacting it with any one or more reagents to form a compound of this invention including any processes specifically delineated herein.

In another aspect, this invention features a method of identifying a compound useful for enhancing efficacy of a therapeutic agent. The method includes incubating a compound in blood cells; separating immune cells from erythrocytic cells (e.g., by density gradient centrifugation, antibody mediated capture, lectin based capture, absorption to plastic, setting, simple centrifugation, peptide capture, activation mediated capture, or flow cytometry); and determining the ratio of the concentration of the compound in the immune cells to the concentration of the compound in the erythrocytic cells (e.g., by mass spectrometry, NMR, PET, fluorescence detection, infrared fluorescence, colorimetry, normal detection methods associated with gas chromatography, Fourrier transform spectrometry method, or radioactive detection); wherein the compound comprises a transportophore and a therapeutic agent, in which the transportophore is covalently bonded to the therapeutic agent via a bond or a linker. The therapeutic agent can be, for example, an anti-inflammatory agent, an anti-infectious agent, an anti-cancer agent, an allergy-suppressive agent, an immune-suppressant agent, an agent for treating a hematopoietic disorder, a lipid lowering agent, an agent for treating a lysosomal storage disorder, a sterol synthesis modifying agent, agents active on protozoa, or an agent for treating a metabolic disease.

In still further another aspect, this invention features a method for delivering a therapeutic agent with a selective concentration. The method includes identifying a compound using the just-described method, and delivering the compound to a cell (e.g., a cell of respiratory tissue, a cell of neoplastic tissue, or a cell mediating allergic responses).

Also within the scope of this invention are a composition having one or more of the compounds of this invention (optionally including one or more other therapeutic agents) for use in treating various diseases described above, and the use of such a composition for the manufacture of a medicament for the just-described use.

The invention provides several advantages. For example, a compound of this invention achieves one or more of the following improvements relative to a therapeutic agent itself: (i) improved uptake across the intestinal, jejunal, duodenal, colonic, or other mucosa; (ii) reduced first pass effect by mucosal oxygenases; (iii) reduced or altered detoxification by degradative enzymes of the body; (iv) reduced efflux; (v) selective accumulation of the therapeutic agent in one or more immune, fibroblast, hepatic, renal, glial, or other target cells; (vi) potential for hydrolytic or other forms of separation on a timescale compatible with therapy and the other desired disposition events; (vi) enhanced pharmacological effect in the target cells through greater concentration, sustained release, reduced substrate competition effect or other mechanisms; (vii) reduced or modified dose; (viii) modified route of administration; (ix) reduced or altered side effects; (x) alternative uses; and (xi) alternative formulations.

Other advantages, objects, and features of the invention will be apparent from the description and drawings, and from the claims.

DETAILED DESCRIPTION

Figure 1:
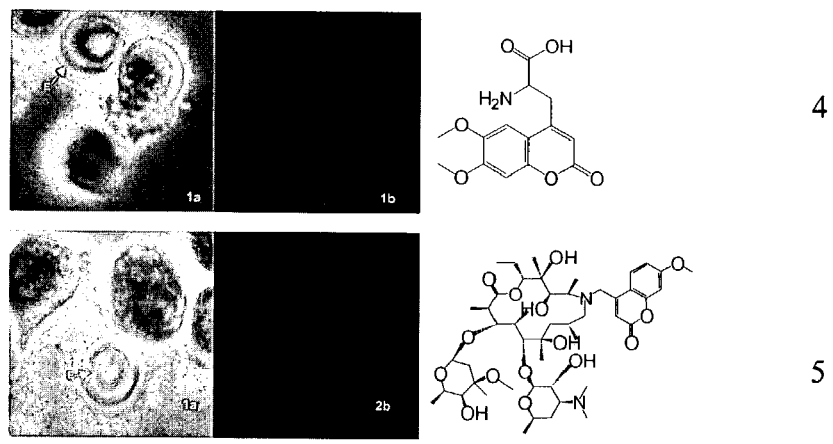
FIG. 1 depicts comparison of selective uptake of diverse structure types into white blood cells from a complex blood mix. These data show that an amino acid (4), a macrolide (5), a sugar (1), a piperazine (2), and a macrolide (3). These data show that diverse properties can be exploited for concentrative uptake and that macrolides can mediate even distribution of their cargo in the cytoplasm.

The invention describes a method for identifying compounds that act to improve the uptake of therapeutic agents into cells such as those that constitute the immune system in mammals. The invention further comprises compounds identified using the method and compounds that could be made based on the teaching provided. The invention provides for the rational improvement of therapeutic agents intended for action in inflammatory disease, infection, cancer, allergy, transplantation, cardiovascular, pulmonary, dermatological, rheumatological and metabolic disease. The invention also provides for methods to engender unoptimized molecules or those with activity only in vitro with improved properties in vivo through simple conjugation with molecules that meet the criteria outlined herein.

The method provides for the selection, in vitro, of combinations of a transportophore and a therapeutic agent that exhibits adequate concentrative uptake and also scission with a half life adequate for agent accumulation and agent action. To identify such a combination, one can contact a sample of native mammalian blood cells (e.g., human blood cell), which contain at least erythrocytes, neutrophils, monocytes, and lymphocytes, with one or more transportophores and determining the relative concentration of those transportophores in the immune cells (at least neutrophils, monocytes and lymphocytes) relative to the concentration of them in the erythrocytes. Then, one can select a transportophore with significantly enhanced concentration in the immune cells and use the transportophore to covalently link to one or more therapeutic agents, via a bond or a linker, to obtain a compound of this invention. Such a compound, containing the transportophore and the therapeutic agent, is also concentrated in immune cells after it is incubated with blood cells. Finally, one can select a linker that provides appropriate cleavage rates between the transportophore and the therapeutic agent in the target cells.

More specifically, a method described in Example 1 achieves an estimate of immune cell selective uptake in a complex and competitive biological fluid such that the observed uptake is relevant to the in vivo situation while simultaneously measuring cell specific uptake. Data from other Examples suggest that the molecules that exhibit preferential uptake in this system are also highly available via the oral route while also being stable in the liver.

A number of variations are possible in the application of the method. The basic method includes contacting the immune cell-erythrocyte preparation with a compound or known compounds and specifically detecting those molecules and their metabolites. A further variation is the use of the method in screening complex mixtures of compounds with separation and detection of the resultant cytoplasmic extracts using Mass selective detection combined with a chromatographic separation technique.

In a further variation, the compounds designated as transportophores are used in the synthesis of libraries such that the final reaction combines library elements with a transportophore using a labile bond allowing the preferential uptake of a compound and its likely scission in an intracellular compartment. Such libraries have the advantage that in cell based assays, there is a reasonable likelihood of adequate therapeutic agent being present at the site of action.

The compound described in the "Summary" section can be prepared by methods known in the art, as well as by the synthetic routes disclosed herein. For example, one can react a transportophore having a reactive moiety with a therapeutic agent having another reactive moiety. One of the two reactive moieties is a leaving group (e.g., —Cl, OR) and the other is a derivatizable group (e.g., —OH, or —NH—). Then, the transportophore is covalently bonded to the therapeutic agent via a reaction between the two reactive moieties. In the case when a linker is present, each of the two reactive moieties, independently, is a leaving group or a derivatizable group, and each reacts with its reactive counterpart in the linker to form a covalent bond. Detailed routes including various intermediates are illustrated in the examples herein.

The chemicals used in the afore-mentioned methods may include, for example, solvents, reagents, catalysts, protecting group and deprotecting group reagents and the like.

The methods described above may also additionally comprise steps, either before or after the steps described specifically herein, to add or remove suitable protecting groups in order to ultimately allow synthesis of the compound of the formulae described herein.

As can be appreciated by the skilled artisan, the synthetic routes herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A therapeutic agent includes any with modes of action that include anti-inflammatory, anti-viral, anti-fungal, immune suppressant, cytostatic, anti-parasitic, lipid lowering, a sterol synthesis modifying, or metabolaregulatory action. The following is a non-exclusive list of potentially useful therapeutic agents.

Anti-Inflammatory Therapeutic Agents

Non-Steroidal Anti-Inflammatory Therapeutic Agents

Diclofenac, Diflunisal, Etodolac, Fenoprofen, Floctafenine, Flurbiprofen, Ibuprofen, Indomethacin, Ketoprofen, Meclofenamate, Mefenamic, Meloxicam, Nabumetone, Naproxen, Oxaprozin, Phenylbutazone, Piroxicam, Sulindac, Tenoxicam, Tiaprofenic, Tolmetin, Acetaminophen, Aspirin, Salicylamide, acetylsalicylic acid, salicylsalicylic acid.

Celecoxib, rofecoxib, JTE-522,

Corticosteroids

Betamethasone, Budesonide, Cortisone, Dexamethasone, Hydrocortisone, Methylprednisolone, Prednisolone, Prednisone, Triamcinolone, Fluticasone Anti-Viral Systemic:

(i) nucleoside/nucleotide reverse transcriptase inhibitors (NRTIs) including but not limited to zidovudine (AZT), didanosine (ddI), zalcitabine (ddC), stavudine (d4T), lamivudine (3TC), abacavir (ABC), emtricitabine [(−)FTC], tenofovir (PMPA) disoproxil fumarate and phosphoramidate and cyclosaligenyl pronucleotides of d4T or similar chemistries.

(ii) non-nucleoside reverse transcriptase inhibitors (NNRTIs) including but not limited to, nevirapine, delavirdine, efavirenz, emivirine (MKC-442) or recent derivatives including capravirine and the novel quinoxaline, quinazolinone, phenylethylthiazolylthiourea (PETT) and emivirine (MKC-442) analogues.

(iii) protease inhibitors (PIs) including but not limited to, saquinavir, ritonavir, indinavir, nelfinavir, amprenavir, and lopinavir or those based on alternative non-peptidic scaffolds such as cyclic urea (DMP 450), 4-hydroxy-2-pyrone (tipranavir)

(iv) viral entry, through blockade of the viral coreceptors including but not limited to, CXCR4 and CCR5 [bicyclams (i.e. AMD3100), polyphemusins (T22), TAK-779, MIP-1 alpha LD78 beta isoform];

(v) virus-cell fusion, through binding to the viral glycoprotein including but not limited to, gp41 [T-20 (pentafuside) (DP-178), T-1249 (DP-107), siamycins, betulinic acid derivatives], and potentially zintevir, L-chicoric acid, CGP64222;

(vi) viral assembly and disassembly, through NCp7 zinc finger-targeted agents including but not limited to, [2,2'-dithiobisbenzamides (DIBAs), azadicarbonamide (ADA) and NCp7 peptide mimics];

(vii) proviral DNA integration, through integrase inhibitors such as L-chicoric acid and diketo acids (i.e. L-731,988);

(viii) viral mRNA transcription, through inhibitors of the transcription (transactivation) process (fluoroquinolone K-12, Streptomyces product EM2487, temacrazine, CGP64222).

(ix) adefovir dipivoxil, emtricitabine and entecavir, aciclovir, valaciclovir, penciclovir, famciclovir, idoxuridine, trifluridine, brivudin, ganciclovir, foscarnet, cidofovir, fomivirsen, maribavir, amantadine and rimantadine, the neuraminidase inhibitors, zanamivir and oseltamivir, ribavirin, levovirin Antifungal, Systemic—
candicidin, echinocandin caspofungin,
Azole antifungal therapeutic agents
Imidazoles:
Clotrimazole, ketoconazole, miconazole, Butoconazole, econazole, oxiconazole, Sulconazole,
Triazoles: fluconazole, itraconazole, Terconazole, Tioconazole (Fluorinated pyrimidines, flucytosine/5-fluorocytosine, 5-fluorouracil.
Penicillium-derivatives,
griseofulvin (oral),
Allylamine and morpholine antifungal therapeutic agents, squalene epoxidase inhibitors
naftifine, terbinafine, amorolfine,
Other,
Dapsone, Haloprogin, Cytostatics and Immune Suppressants
Alkylating agents,
Nitrogen Mustard Derivatives, Chlorambucil, Cyclophosphamide, Ifosfamide, Mechlorethamine, Melphalan, Uracil Mustard,
Nitrosoureas, Carmustine, Lomustine, Streptozocin, Aziridine, Thiotepa,
Methanesulfonate Ester, Busulfan, chronic myelogenous leukemia
Nonclasic Agents, Dacarbazine, Procarbazine,
Platinum Complexes, Carboplatin, Cisplatin,
Antitumor antibiotics, Dactinomycin, Daunorubicin, Doxorubicin, Idarubicin, Mitomycin, Mitoxantrone,
Antimetabolites, Fluorouracil, Floxuridine, Capecitabine,
Cytidine Analogs, Cytarabine, Gemcitabine,
Purines, Cladribine, Fludarabine, Mercaptopurine, Methotrexate, Pentostatin, Thioguanine
Plant Alkaloids, (DNA repair enzyme inhibitors)
Semisynthetic Podophylline Derivitives, Etoposide, Teniposide
Taxoid Plant Alkaloids, Docetaxel, Paclitaxel,
Synthetic camptothecin
Plant Alkaloid Derivitives, Irinotecan, Topotecan,
Vinca Alkaloids, Vinblastine, Vincristine, Vinorelbine,
Other agents,
All-trans-retinoic acid, Imatinab mesylate, 2-deoxycoformycin, all-trans retinoic, thalidomide calicheamycin, protein kinase inhibitors Therapeutic Agents Active on Allergy Anti-Histamines
Astemizole, Azatadine, Brompheniramine, Cetirizine, Chlorpheniramine, Clemastine, Cyproheptadine, Dexchlorpheniramine, Dimenhydrinate, Diphenhydramine, Doxylamine, Hydroxyzine, Loratadine, Phenindamine, Terfenadine, Tripelennamine.

Lipid Lowering and Sterol Modifying Agents
Atorvastatin, Pravastatin, Simvastatin, Lovastatin, Cerivastatin, Roxuvastatin, Fluvastatin, Gemfibrozil Also within the scope of this invention is a pharmaceutical composition that contains an effective amount of at least one of the compound of this present invention and a pharmaceutically acceptable carrier.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, mesylate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

Further, this invention covers a method of administering an effective amount of one or more compounds of this invention to a subject (a human, a mammal, or an animal, e.g., dog, cat, horse, cow, or chicken) in need of treatment for a disease or disease symptom (e.g., an inflammatory disease, an infectious disease, cancer, allergy, or an immune disease, or symptoms thereof).

The term "treating" or "treated" refers to administering a compound of this invention to a subject with the purpose to cure, heal, alleviate, relieve, alter, remedy, ameliorate, improve, or affect a disease, the symptoms of the disease or the predisposition toward the disease. "An effective amount" refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 20 mg/Kg. Effective doses will also vary, as recognized by those skilled in the art, depending on route of administration, excipient usage, and the possibility of co-usage with other agents for treating a disease, including an inflammatory disease, a cardiovascular disease, an infectious disease, cancer, allergy, and an immune disease.

The methods delineated herein can also include the step of identifying that the subject is in need of treatment of for a disorders and or condition in athe subject. The identification can be in the judgment of a subject or a health professional and can be subjective (e.g., opinion) or objective (e.g., measurable by a test or a diagnostic method).

The following is a non-exclusive list of diseases and disease symptoms, which may be treated or prevented by administration of the compounds and compositions thereof herein and by the methods herein.

Inflammation and Related Disorders

Inflammation Secondary to Trauma or Injury
Post traumatic regeneration injury including but not limited to Ischemia, reperfusion injury, scarring, CNS trauma, spinal section, edema, repetitive strain injuries including tendonitis, carpal tunnel syndrome, Cardiovascular Diseases
specifically atherosclerosis, inflamed or unstable plaque associated conditions, restinosis, infarction, thromboses, post-operative coagulative disorders, acute stroke, Autoimmune Diseases Alopecia Areata, Ankylosing Spondylitis, Antiphospholipid Syndrome, Autoirrimune Addison's Disease, aplastic anemia, Autoimmune Hemolytic Anemia, Autoimmune Hepatitis, Behcet's Disease, biliary cirrhosis, Bullous Pemphigoid, Canavan Disease, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, dermatomyositis, Diffuse Cerebral Sclerosis of Schilder, Discoid Lupus, Essential Mixed Cryoglobulinemia, Fibromyalgia-Fibromyositis, Fuch's heterochromic iridocyclitis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin dependent Diabetes, Intermediate uveitis, Juvenile Arthritis, Lichen Planus, Lupus, Ménière's Disease, Mixed Connective Tissue Disease, Multiple Sclerosis, Myasthenia Gravis, nephrotic syndrome, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammag-lobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Vasculitis, Vitiligo, VKH (Vogt-Koyanagi-Harada) disease, Wegener's Granulomatosis, Anti-Phospholipid Antibody Syndrome (Lupus Anticoagulant), Churg-Strauss (Allergic Granulomatosis), Dermatomyositis/Polymyositis, Goodpasture's Syndrome, Interstitial Granulomatous Dermatitis with Arthritis, Lupus Erythematosus (SLE, DLE, SCLE), Mixed Connective Tissue Disease, Relapsing Polychondritis, HLA-B27 associated conditions including Ankylosing spondylitis, Psoriasis, Ulcerative colitis, Crohn's disease, IBD, Reiter's syndrome, Uveal diseases: Uveitis, Pediatric Uveitis, HLA-B27 Associated Uveitis, Intermediate Uveitis, Posterior Uveitis, Iritis, Dermatological Disease Psoriasis, atopic dermatitis, acne Rheumatological Disease Osteoarthritis and various forms of autoimmune arthritis.

Neurodegenerative Disease

Inflammatory Degenerative Diseases

Including variants and major forms of: Alzheimer's, Huntington's Parkinson's and Creutzfeldt Jakob disease Infection Respiratory Diseases of Diverse Origin Including:

Pharyngitis ("sore throat"), Tonsilitis, Sinusitis & Otitis Media, Influenza, Laryngo-Tracheo Bronchitis (Croup), Acute Bronchiolitis, Pneumonia, Bronchopneumonia, Bronchiolitis, Bronchitis, Acute pharyngitis with fever, Pharyngoconjunctival fever, Acute follicular conjunctivitis, Pneumonia (and pneumonitis in children), COPD, asthma, Gastrointestinal Diseases Gastroenteritis of diverse origin Viral Diseases Target viruses include but are not limited to: Paramyxo-, Picoma-, rhino-, coxsackie-, Influenza-, Herpes-, adeno-, parainfluenza-, respiratory syncytial-, echo-, corona-, Epstein-Barr-, Cytomegalo-, Varicella zoster, Hepatitis variants including hepatitis C Virus (HCV), Hepatitis A Virus (HAV), Hepatitis B Virus (HBV), Hepatitis D Virus (HDV), Hepatitis E Virus (HEV), Hepatitis F Virus (HFV), Hepatitis G Virus (HGV), Human immunodeficiency- Parasitic Diseases Helminthiases and Similar Diseases Larva Migrans, Toxocara canis, Hookworm Infections (Ancylostomiasis) Necator spp. Ancylostoma duodenale and Necator americanus, Filariasis, Wuchereria bancrofti & Brugia malayi, Loiasis, Ascariasis, Ascaris lumbricoides -, Dracunculiasis, Schistosomiasis, Schistosoma mansoni, male & female [P Darben]-(AU), Onchocerciasis (River Blindness), Whipworm Infections, Ascaris lumbricoides and Trichuris trichiura, Trichinosis, Trichinella, Cestode Infections, Diphyllobothriasis, Diphyllobothrium spp., Echinococcosis, Echinococcisis (Hydatid Disease), Echinococcus multilocularis, Taeniasis, (Tapeworm Infection), Cysticercosis Leishmaniasis (Kala Azar), Leishmania donovani, Enterobius vermicularis, Anal Pinworms, Dientamoebiasis, Dientamoeba fragilis, Anisakiasis, Anisakis simplex, Giardiasis, *Giardia lamblia, Giardia muris*

Protozoan Infection

Acanthamoeba sp. Flagellates, Amebiasis, Naegleria, Acanthamoeba and Balamuthia, Entamoeba, Trichomonas Infections, Blastocystis hominis infections (not on MeSH), Malaria, Plasmodium falciparum, Toxoplasmosis, Cryptosporidiosis, Cyclosporiasis, Cyclospora cayetanensis, Babesiosis, Trypanosomiasis, Trypanosomiasis, Trypanosoma brucei, Chagas Disease Neoplastic Disease leukemia, lymphoma, myeloma hepatomas, other major organ carcinomas and sarcomas glioma, neuroblastoma, Astrocytic and glial tumors, Invasive or non-invasive (Anaplastic (malignant) astrocytoma, Glioblastoma multiforme variants: giant cell glioblastoma, gliosarcoma, Pilocytic astrocytoma, Subependymal giant cell astrocytoma, Pleomorphic xanthoastrocytoma)

Oligodendroglial Tumors

Ependymal cell tumors, Mixed gliomas, Neuroepithelial tumors of uncertain origin, Tumors of the choroid plexus, Neuronal and mixed neuronal-glial tumors, Pineal Parenchyma Tumors, Tumors with neuroblastic or glioblastic elements (embryonal tumors), Neuroblastoma, ganglioneuroblastoma, Tumors of the Sellar Region, Hematopoietic tumors, Primary malignant lymphomas, Plasmacytoma, Granulocytic sarcoma, Germ Cell Tumors, Tumors of the Meninges Allergy Rhinitis, bronchitis, asthma and conditions relating to excessively active or stimulated cosinophils.

Transplant Medicine

Renal, hepatic, corneal, stem cell, pulmonary, cardiac, vascular, and myeloid transplants Metabolic Disease, Various disorders clustered in the liver cirrhosis, dyslipidemia, diabetes, obesity and hypercholesterolemia groupings.

Benefits of the Invention:

The conjugates described here represent improvements on their parent therapeutic agents in two main respects. First, these conjugates provide a facile means of improving the activity of a therapeutic agent through their ability to make the therapeutic agent more easily available either from the gut, or from the blood stream. This is especially important for those therapeutic agents that have good activity in vitro but are unable to exert that activity in vivo. Where the non-manifestation of activity is related to inefficient uptake and distribution, simple conjugations according to the schemes described here are an efficient means to generate improved activity.

The invention also has specific benefits. By targeting cells, and achieving higher concentration in those cells than in plasma or general tissue, the therapeutic agent may exert a more specific action resulting in fewer systemic side effects. Where efficacy is limited by the ability to place sufficient therapeutic agent at the site of action, such concentration effects are significant in achieving improved in vitro effect. This may be understood more clearly by examination of non-limiting but representative examples from different therapeutic areas.

In Examples 10-16, improved anti-inflammatory therapeutic agents are described in which the active moleculs are concentrated into immune cells in vitro through conjugation with a macrolide. These conjugates display superior immune suppressive and anti-inflammatory action in vivo when compared with the effect of a mixture of the two component molecules in the same system. The mechanism for this action is unknown but the effect in protection appears to be qualitatively similar for the mixture and the conjugate suggesting that the conjugate is largely a delivery mechanism for the therapeutic agent. One potential non-exclusive explanation is that immune cells produce high levels of arachidonate, the substrate of cyclooxygenase enzymes, resulting in competition between this substance and NSAID therapeutic agents for sites on cyclo-oxygenase enyzymes (substrate competition is known in the art as a common means of reducing the efficiency of an inhibitor). Enhanced concentration of the therapeutic agent has the potential to overcome this feedback inhibition resulting in a greater inhibition of flux through the enzyme. The conjugate also has other potential benefits including the prevention of metabolism through steric effects, increased residence time and traffic to sites of inflammation when it is taken up into target cells which are tropic for the inflamed tissues. Some action of the conjugate itself cannot be ruled out when it is present at high concentrations in a cell.

In example 24, an anti-viral therapeutic agent conjugate is cited that also achieves higher levels in immune cells which may act as a reservoir of integrated viral material. If therapeutic agent is selectively conjugated such that it is concentrated in these cells, it has two potential benefits including, the ability to suppress viral replication at lower systemic doses, and the ability to prevent resistance through the maintenance of persistently higher concentrations of therapeutic agent such that mutations with minor effect cannot accumulate.

Similar themes but contrasting mechanisms apply to the field of graft rejection where one focus of therapy is the prevention of T-cell responses to the donor organ. Various mechanisms are known but all would benefit if a greater proportion of chemical effect were focused on the T-cells themselves such that the systemic dose were reduced. Example 21. cites conjugates of mycophenolic acid that are highly concentrated in immune cells. These conjugates are also highly bioavailable in the rat and cleave slowly to release mycophenolic acid. Despite slow cleavage, the compounds have very similar anti-proliferative activity in vitro when compared with unconjugated mycophenolic acid suggesting that concentration can compensate for slow hydrolysis such that the conjugate becomes an intracellular reserve for the slow release of mycophenolate.

Similar advantages can be cited for cancer where those neoplasms are of a type that takes up the conjugates to the same extent seen in immune cells. Cancers of myeloid origin are a good example of a target neoplasm. In such cancers, concentration of the therapeutic agent has potential to compensate for common resistance mechanisms such as gene amplification and the over expression of efflux systems. In certain cancers, the tumour is associated with an intense local inflammation. The inflammatory infiltrate may serve as a means of further concentration of the conjugate drugs in the environs of the tumour.

In cardiovascular diseases such as atherosclerosis, it is commonly known that there is a strong inflammatory component to the events which result in the thickening and fragmentation of the plaque. This inflammation may be effectively reduced by the application of a range of agents including conjugates of compounds that are antiinflammatory in effect.

Data to support these observations may be found in various examples and is summarized here by reference in a non-limiting manner.

To practice the method of treating a disease, the compounds of this invention can be administered to a patient, for example, in order to treat a disease described above. The compound can, for example, be administered in a pharmaceutically acceptable carrier such as physiological saline, in combination with other therapeutic agents, and/or together with appropriate excipients. The compound described herein can, for example, be administered by injection, intravenously, intraarterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.1 to about 20 mg/kg of body weight, preferably dosages between 10 mg and 1000 mg/dose, every 4 to 120 hours, or according to the requirements of the particular therapeutic agent. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, therapeutic agent combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying therapeutic agent delivery systems (SEDDS) such as D-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A suitable in vitro assay can be used to preliminarily evaluate a compound of this invention in treating a disease. In vivo screening can also be performed by following procedures well known in the art. See the specific examples below.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following example. It should be understood that these examples are for illustrative purposes only and are not to be construed as limiting this invention in any manner.

EXAMPLES

| Example number | Subject |
|---|---|
| 1. | Method for determining immune cell partition |
| 2. | Transportophore: Compound 39 |
| 3. | Transportophore: Compound 40 |
| 4. | Transportophore: Compound 41 |
| 5. | Transportophore: Compound 42 |
| 6. | Transportophore: Compound 44 |
| 7. | Transportophore: Compound 45 |
| 8. | Transportophore: Compound 46 |
| 9. | Transportophore: Compound 47 |
| 10. | Transportophore: Compound 48 |
| 11. | Transportophore: Compound 49 |
| 12. | Transportophore: Compound 50 |
| 13. | NSAID Conjugate: Diclofenac Conjugates; Compound 52, 53, 54, & 55 |
| 14. | NSAID Conjugate: Compound 56 |
| 15. | NSAID Conjugate: Compound 57 |
| 16. | NSAID Conjugate: Compound 58 |
| 17. | NSAID Conjugate: Compound 59 |

-continued

| Example number | Subject |
|---|---|
| 18. | NSAID Conjugate: Compound 60 |
| 19. | NSAID Conjugate: Compound 61 |
| 20. | Conjugates of cytotoxic agents: Compound 62 |
| 21. | Conjugates of cytotoxic agents: Compound 64 |
| 22. | Neotrofin conjugate: Compound 65 |
| 23. | Gemfibrozil conjugate: Compound 66 |
| 24. | Mycophenolic Acid conjugates: CompoundS 67, 68, 69, 71, 73, 74, 75, 78, 79, 80, & 81 |
| 25. | Steroid Conjugates: Compounds 82, 83, 84, 85, & 86 |
| 26. | Statin Conjugates: Compounds 87 & 88 |
| 27. | Antifungal Conjugate: Compound 89 |
| 28. | Antiviral Nucleoside Conjugates: Compounds 90, 92, 94, 97, & 101 |
| 29. | NSAID Conjugate: Compound 106 |
| 30. | Coumarin Conjugates: Compounds 108, 109 |
| 31. | Imatinab Conjugate: Compound 110 |
| 32. | Proliferation Assay |
| 33. | Cell-Based IMPDH Assay with Guanosine Rescue |
| 34. | Efficacy Testing of Drugs using Collagen-Induced Arthritis in Mice |
| 35. | Efficacy Testing of Immunosuppressive Drugs Using a Mouse Skin Transplant Model |
| 36. | Testing of Antibiotic Activity of Drugs |

Example 1

Determination of the Immune Selectivity Ratio Coefficient (PISR)

Uptake of Compounds

Freshly drawn heparinised blood or buffy coat preparations are used for the determination of immune cell partition ratios. Buffy coat preparations are preferred. These may be obtained from donor blood by simple centrifugation of whole blood (4795 g for 10 minutes). Following centrifugation, plasma is collected from the surface, after which immune cells are expressed from the donor bags along with the erythrocytes lying immediately below the leukocyte layer. This ensures high yields and a sufficient population of erythrocytes for partition. 5 ml of the resulting cell suspension are dispensed into T25 culture flasks. Substrates are added to a final concentration between 1 and 10 µM and the suspensions incubated at 37° C., in a 5% $CO_2$ atmosphere. For analysis of uptake kinetics, samples are withdrawn at 0, 2, 5, 10, 30, 60, 90, 180, or 240 min after substrate addition. For screening purposes, samples are taken at 0 and 120 minutes.

Buffers and Solutions

PBS 73 mM NaCl, 2.7 mM KCl, 1.5 mM $KH_2PO_4$, 8 mM $Na_2HPO_4$, pH 7.4

DPBS 137 mM NaCl, 3 mM KCl, 8 mM $Na_2HPO_4$, 1 mM $KH_2PO_4$, 1 mM $CaCl_2$, 0.5 mM $MgCl_2$, 5 mM Glucose, pH 7.4

Separation of Blood Cell Fractions—Density Gradient Centrifugation

Cell fractions were prepared using density gradient centrifugation. Mononuclear cells and polymorphonuclear cells are separated from erythrocytes essentially by layering the cell suspension on a viscous medium typically composed of a solution containing Ficoll or similar (commercial suppliers include: Lymphoprep, Axis Shield, 1031966; Lymphoflot HLA, 824010; or PMN Separation Medium Robbins Scientific 1068-00-0). The layered suspension is then centrifuged at 600 g, 20 min, after which the cell fractions and the plasma (incubation medium) fraction are removed by gentle aspiration, washed twice in PBS buffer, followed by estimation of the cell number and pellet volume.

Analysis

Uptake of fluorescent compounds is monitored using fluorescence microscopy. Excitation and emission wavelengths depend of the fluorescence label in use. A typical label is a methoxy coumarin for which the appropriate wavelengths are 360 and 450 nm respectively. Fluorescent analogs of the compounds under study permit the estimation of appropriate uptake intervals as well as the likely intracellular distribution of the compounds. Fluorescent analogs also allow the estimation of losses in washing or other cell manipulations.

Cell preparations are lysed in water and the debris sedimented at 16100 g, 10 min. The supernatant is recovered and sub-sampled for protein and DNA content. Protein in the supernatant is precipitated by bringing the solution to 100% v/v ethanol and centrifuging again at 16100 g, 10 min.

Compound uptake is normalized according to cytoplasmic volume of cells in order to obtain the average concentration in the cells. Cell volume is estimated by correlation of DNA, protein or haem content of lysed cell aliquots to cell number and packed volume prior to lysis.

Cell lysates are analysed using a HP 1100 HPLC System (Agilent Technologies, Waldbronn, Germany) with a Kromasil 3.5µ C18, 50×2.0 mm column and guard cartridge system (both, Phenomenex, Aschaffenburg, Germany) run at 30° C. A gradient elution was performed using water, 0.05% formic acid (A) and acetonitrile 0.05% formic acid (B) (0 min. 5% B, 2.5 min 5% B, 2.8 min 40% B, 10.5 min 85% B, 12.0 min 95% B, 16.5 min 95% B) at a flow rate of 300 µl/min. Re-equilibration of column was at 5% B, at a flow rate of 750 µl/min for 2.4 min. The HPLC-eluate from retention time 0.0 min to 2.5 min was directed directly to waste. Detection was via a UV cell at 214 nm followed by a ⅙ split to an An API-qTOF 1 (Micromass, Manchester, UK) mass spectrometer, (calibrated daily using a mixture of NaI, RbI and CsI). The mass spectrometer is routinely operated in the positive electrospray ionization mode using the following settings: Capillary voltage 4000 V; cone voltage 30 V; RF Lens offset 0.38 V; source block temperature 80° C.; desolvation gas temperature 140° C.; desolvation gas 240 l/h; LM/HM Resolution 0.0; Collision energy 4.0 V; Ion energy 5.0 V.

Masses are monitored according to the known or expected M/Z ratios. Ion currents across the expected range of masses (including metabolites) are recorded and the chromatograms for specific masses used to estimate the peak area for a given molecular ion (area proportional to concentration over a given range). Normalisation to DNA and/or protein and/or haem content of cells (all three measured with standard methods (Bisbenzimide staining (Sigma), BCA protein assay kit (Pierce) and haem absorbance at 535 nm, respectively)) to cell number (hemocytometer count) and cell volume is employed to calculate average compound concentration in the cell fraction (expressed in uM). Formation of metabolites or hydrolysis products was also monitored for each T—L—C conjugate and the rate of hydrolysis estimated from both the total uptake and the loss of metabolites to the medium. The final ratio is computed by comparing the concentration of a component in the immune cell compartment with that in both the erythrocytes and the plasma. The $P_{ISR}$, is then the concentration in immune cells/concentration in erythrocytes using the same concentration units. Thus a $P_{ISR}$ of 2 indicates a two-fold concentration relative to erythrocytes.

Selection and Definition of Carrier Compounds

Figure 2:
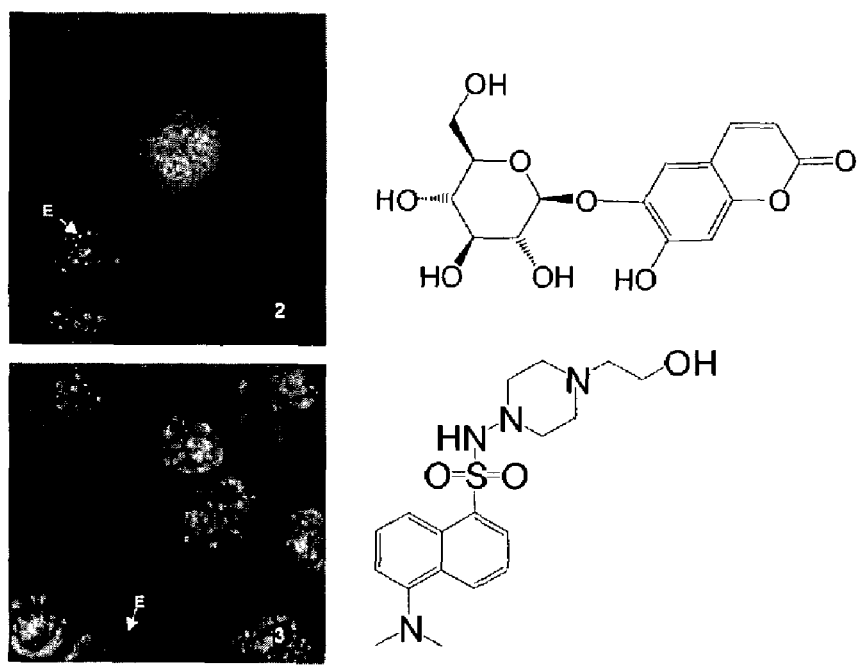
FIG. 2 depicts comparison of sugar and piperazine driven uptake of a fluorophore.
Figure 3:
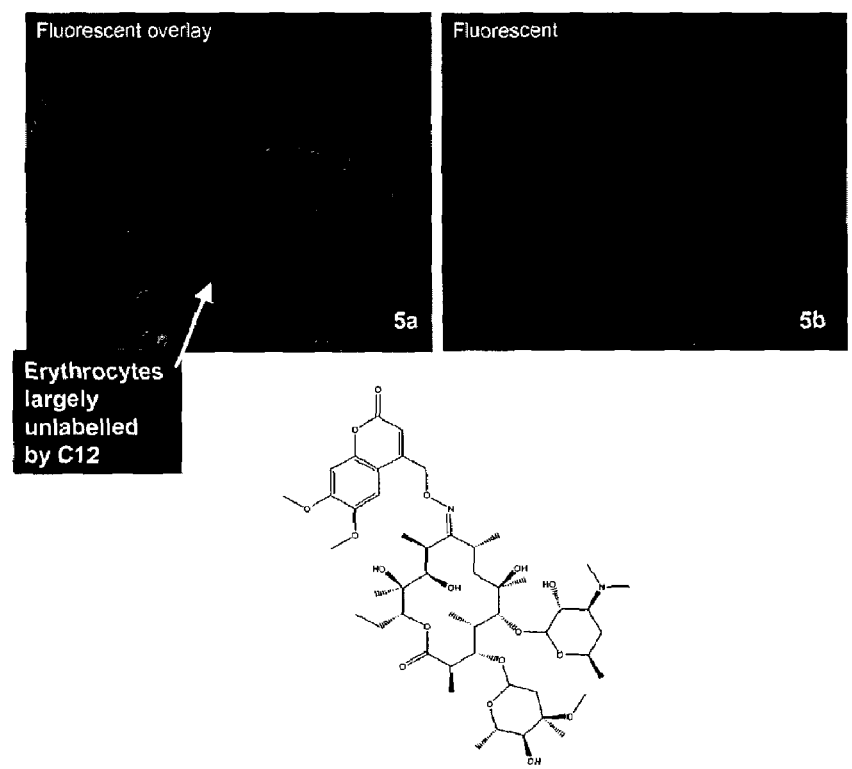
FIG. 3 is bright-field overlay and fluorescent image of polymorphonuclear cells that have taken up a fluorescent macrolide (compound 3). The images suggest even distribution with some concentration near the nucleus.
Figure 4:
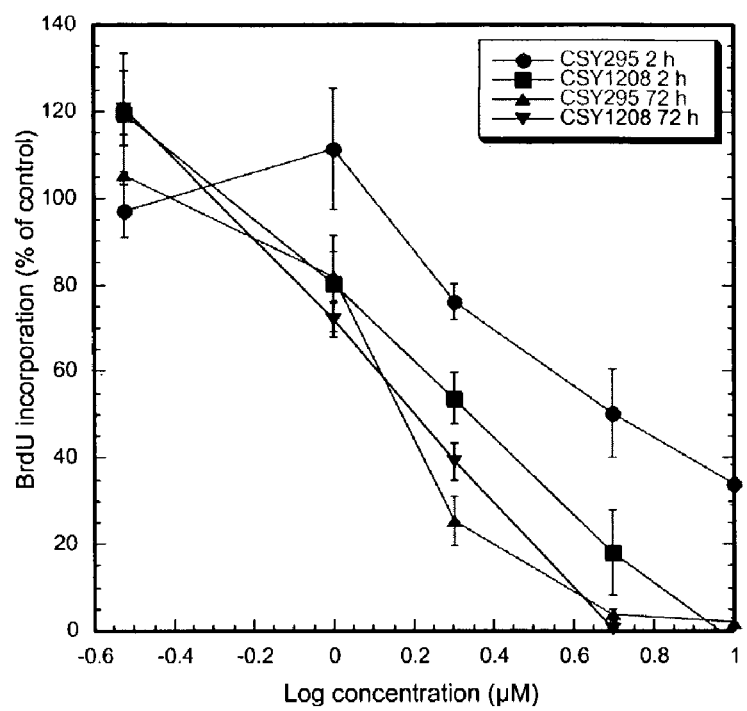
FIG. 4 is an example of results from a proliferation assay showing increased efficacy of a T—L—C conjugate following concentrative uptake into lymphocytes.
Figure 5:
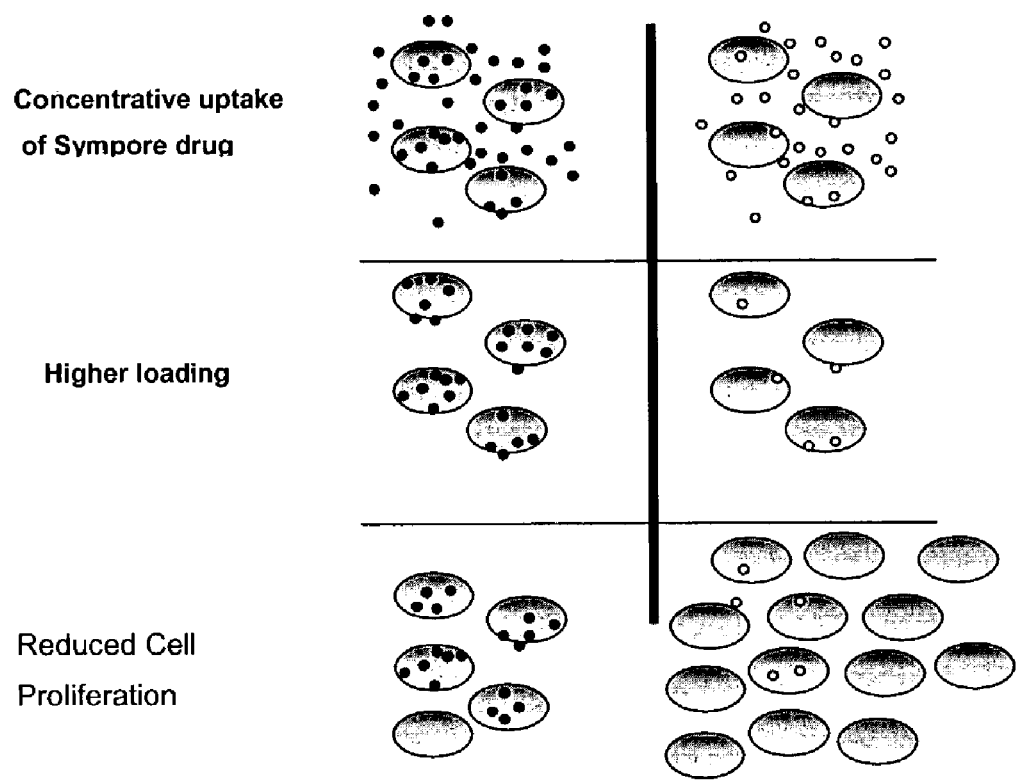
FIG. 5 depicts a model to demonstrate the advantage of uptake into target cells.
Figure 6:
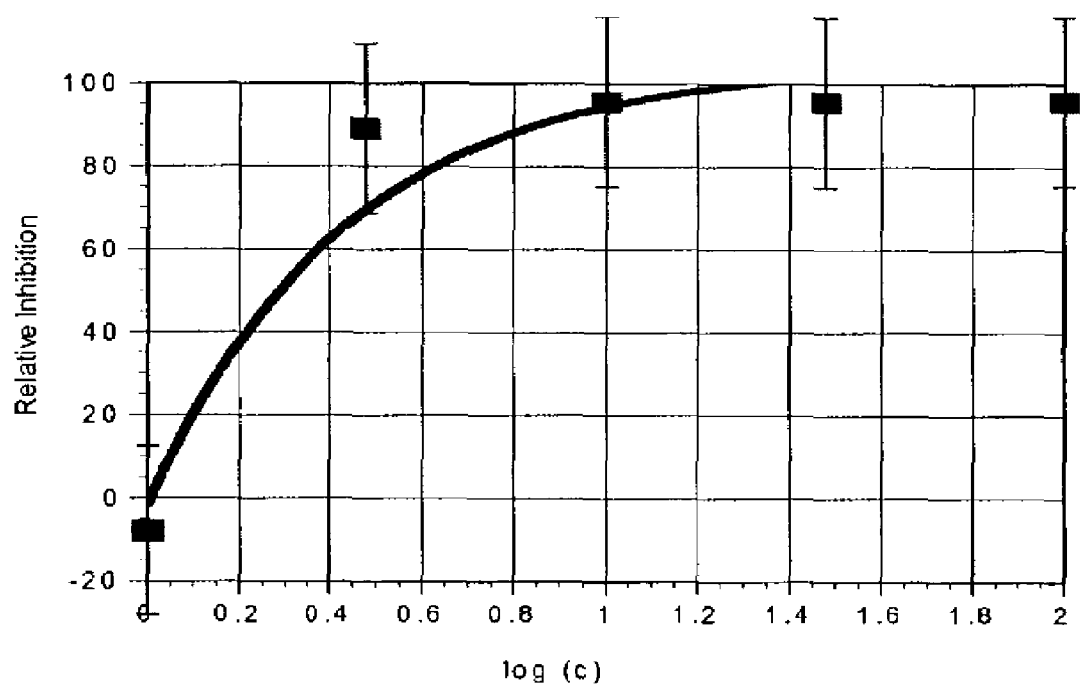
FIG. 6 is an example of a response of HeLa cells to a mycophenolic acid conjugate.
Figure 7:
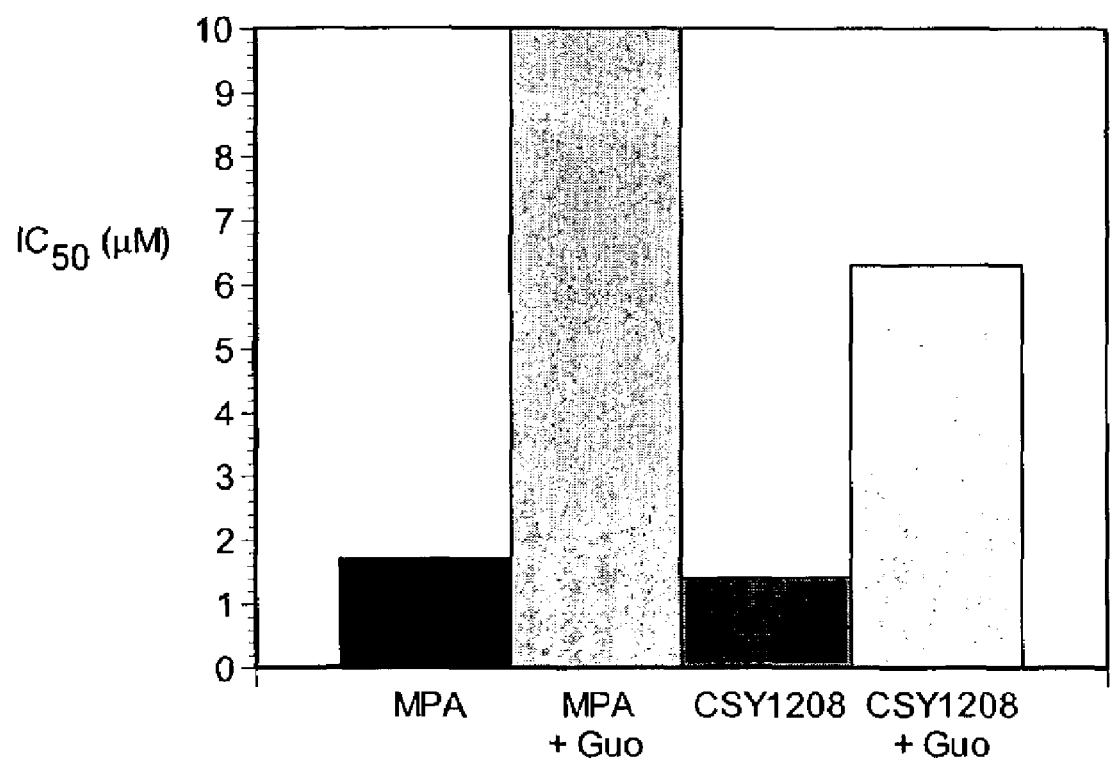
FIG. 7 is an example of guanosine amelioration following treatment of fresh PBMNCs with either mycophenolic acid or a T—L—C conjugate thereof.
Figure 8:
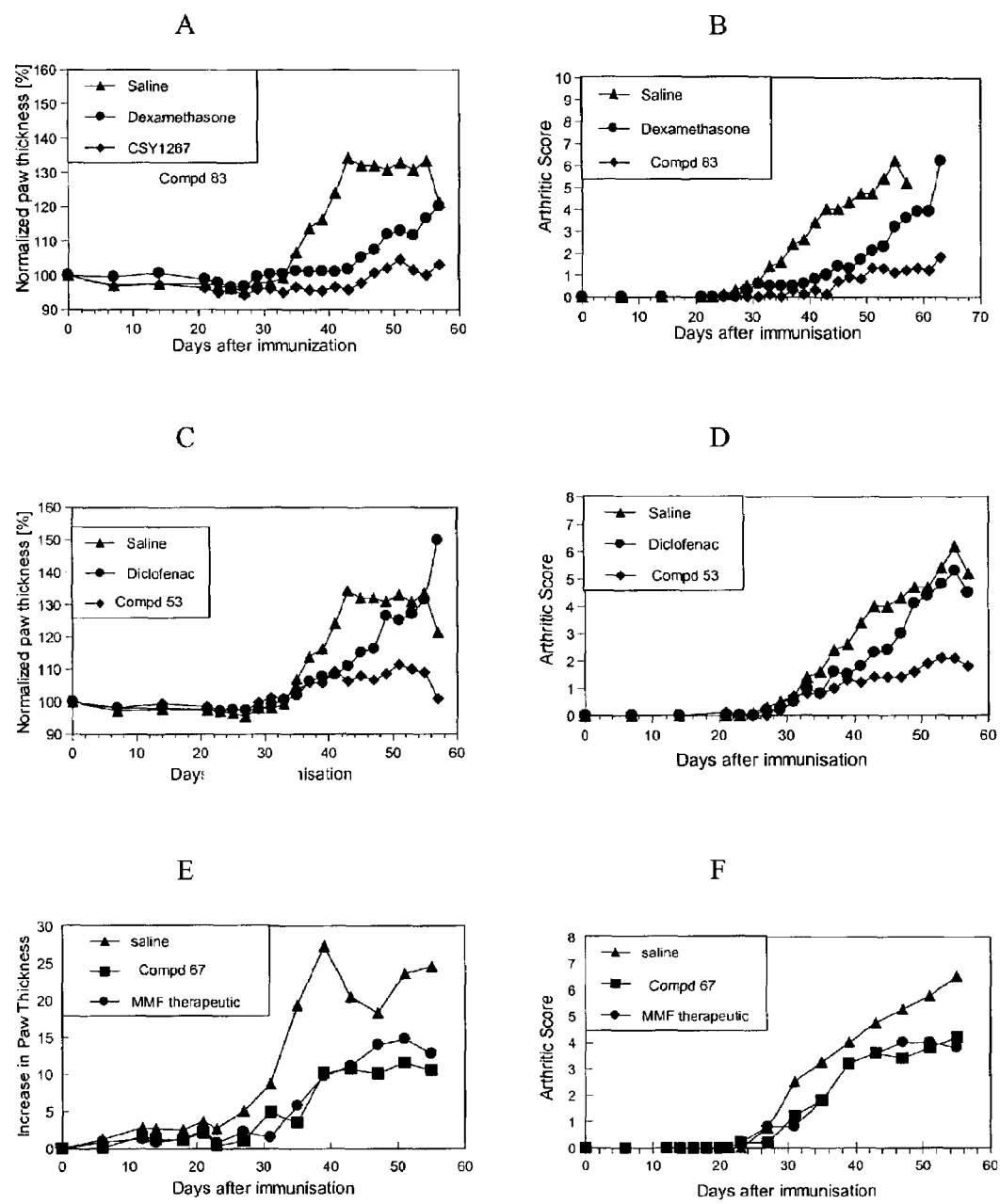
FIG. 8 shows changes in normalized paw thickness (left) and the corresponding arthritic scores (right) of mice treated with different conjugates. Saline and unconjugated compounds are included as controls.

Immune cell selectivity assays provide data in the form of micrographs of fluorescent analogs and quantitative estimates of compound concentration. Micrographs are useful in determining the intracellular disposition of compounds (FIG. 1). It is apparent from the illustrations that compound distribution is generally uniform with some examples appearing granular or nuclear. The analysis of fluorescent libraries by this method provides an efficient means of selecting T molecules that are capable of mediating the transport of diverse substances into a cell. Examples of molecules assayed in this way are summarized in Table 2 along with their uptake data and selectivity. These data show that similar molecules with similar properties can exhibit quite different uptake into immune cells, hence the difficulty in employing general specifications known in the art (Lipinski et al., 2001) Further, it is clear from the images obtained during the course of uptake (FIG. 1, FIG. 2, or FIG. 3) that for some structures, the process is a slow one relative to pure lipophilic diffusion. This is indicative of processes in uptake that depend on factors other than diffusion alone. Certain investigators have proposed that compounds of the macrolide type are subject to active, protein mediated concentrative mechanisms although these remain unknown (Labro, 1998). The data presented here for compounds 4 and 5 suggest that uptake is rapid but that it varies with each structure which does not exclude a concentrative mechanism involving protein action.

Compounds exhibiting high uptake are outlined in Table 2 along with similar structures that do not. It is clear from an inspection of the structures that there exist a variety of chemical and physical properties compatible with selective entry into white blood cells. These data are consistent with there being a multiplicity of mechanisms for cell entry and accumulation including passive entry and active uptake. These data further suggest that compounds with properties supposedly compatible with facile uptake into actively metabolizing cells such as immune cells do not exhibit such properties. Simple addition of basic functions is not always effective, even in in vitro screening. In contract, addition of sugars, amino acids, or peptides can enhance entry of fluorescent compounds. Based on both the micrographs above and analysis of immune cells following uptake, it is clear that macrolide structures are very effective at mediating the entry of fluorescent molecules into cells and that other basic compounds did not exhibit this property. In sum, it is clear that an empirical method is the only reliable means of selecting and guiding synthetic chemistry toward compounds that are well distributed and concentrated in immune cells.

TABLE 2

Compounds exhibiting concentrative uptake in white cells

| Substrate | Structure | cLogP | Concentrative uptake |
|---|---|---|---|
| Compound 3 | 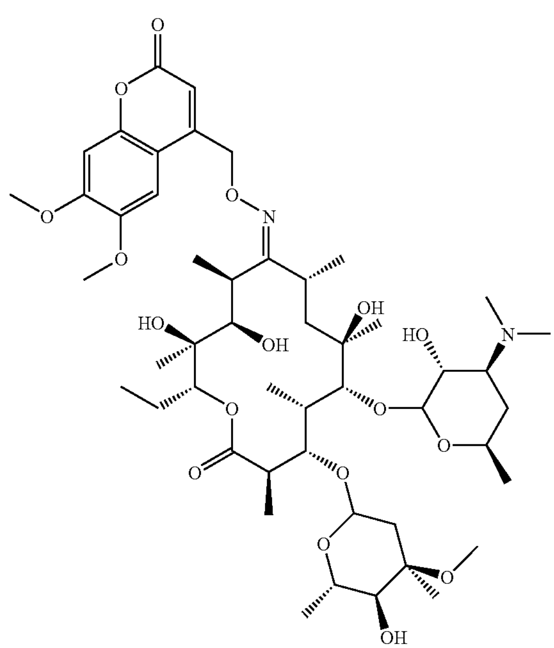 | n.d. | Y |

TABLE 2-continued

Compounds exhibiting concentrative uptake in white cells

| Substrate | Structure | cLogP | Concentrative uptake |
|---|---|---|---|
| Compound 6 | | n.d. | Y |
| Compound 7 | | n.d. | Y |

TABLE 2-continued

Compounds exhibiting concentrative uptake in white cells

| Substrate | Structure | cLogP | Concentrative uptake |
|---|---|---|---|
| Compound 8 | 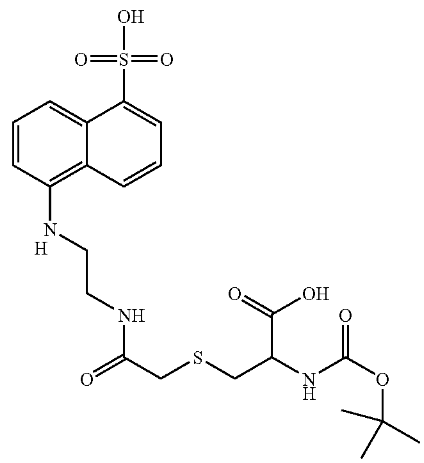 | 1.02 | Y |
| Compound 4 | 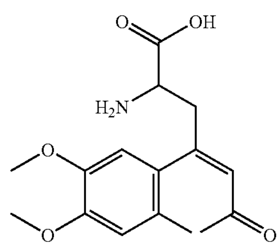 | 0.01 | Y |
| Compound 1 | 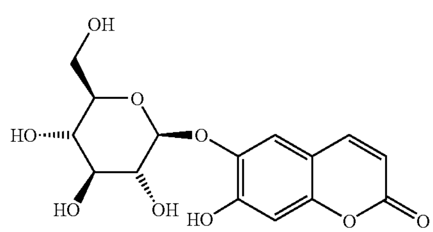 | −0.79 | Y |
| Compound 9 | 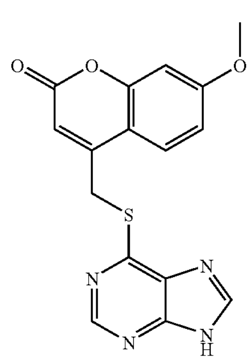 | 1.86 | N |

TABLE 2-continued

Compounds exhibiting concentrative uptake in white cells

| Substrate | Structure | cLogP | Concentrative uptake |
|---|---|---|---|
| Compound 10 | 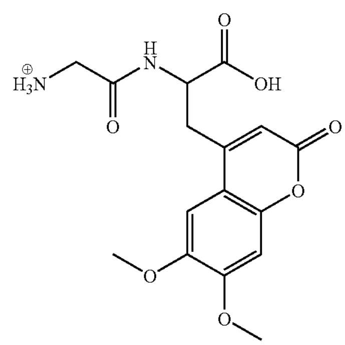 | −1.14 | N |
| Compound 11 | 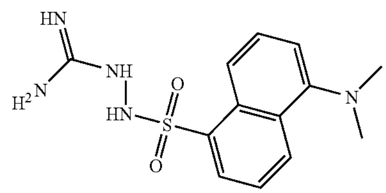 | 1.48 | N |
| Compound 12 | 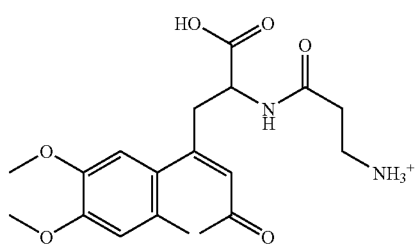 | −0.68 | N |
| Compound 13 | 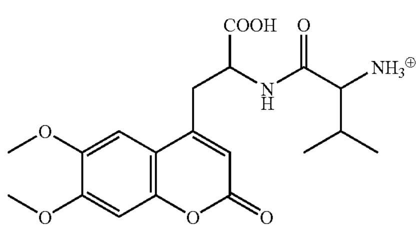 | −0.56 | N |
| Compound 14 | 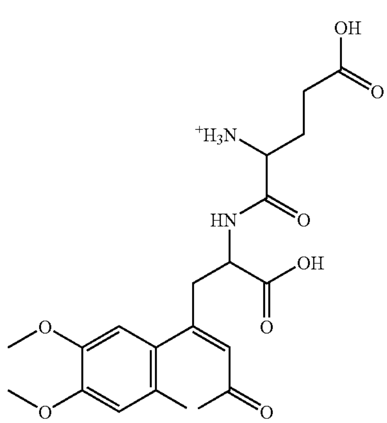 | −1.63 | N |

TABLE 2-continued

Compounds exhibiting concentrative uptake in white cells

| Substrate | Structure | cLogP | Concentrative uptake |
|---|---|---|---|
| Compound 15 | | n.d. | Y |
| Compound 16 | | n.d. | Y |
| Compound 17 | | n.d. | Y |

TABLE 2-continued

Compounds exhibiting concentrative uptake in white cells

| Substrate | Structure | cLogP | Concentrative uptake |
|---|---|---|---|
| Compound 18 | | n.d. | Y |
| Compound 19 | | n.d. | N |
| Compound 20 | | −1 | Y |

TABLE 2-continued
Compounds exhibiting concentrative uptake in white cells
| Substrate | Structure | cLogP | Concentrative uptake |
|---|---|---|---|
| Compound 21 | 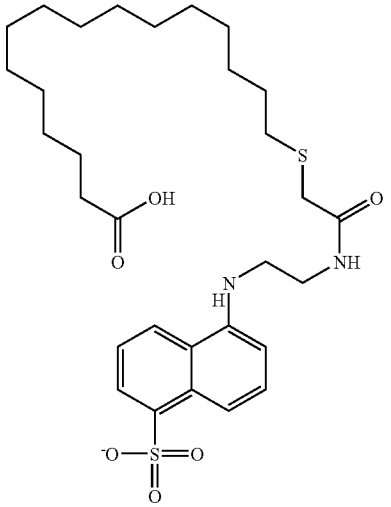 | 5.59 | Y |
| Compound 22 | 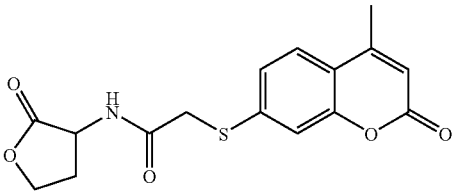 | 0.84 | Y |
| Compound 23 | 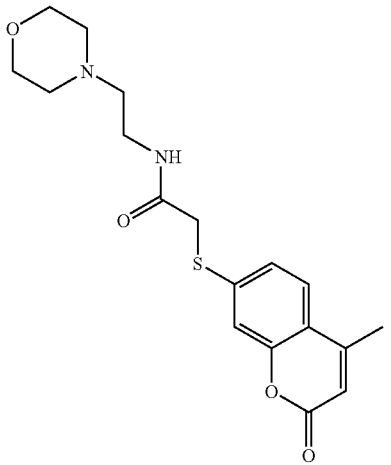 | 0.89 | Y |

TABLE 2-continued

Compounds exhibiting concentrative uptake in white cells

| Substrate | Structure | cLogP | Concentrative uptake |
|---|---|---|---|
| Compound 24 | 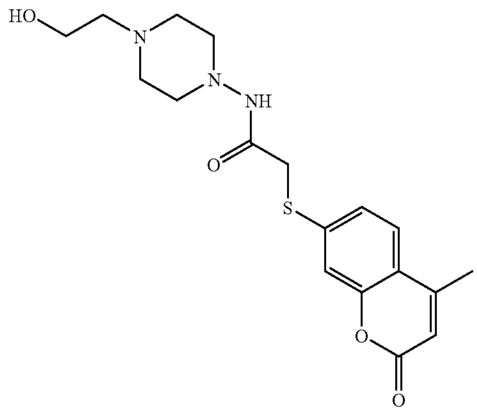 | 0.58 | N |
| Compound 25 | 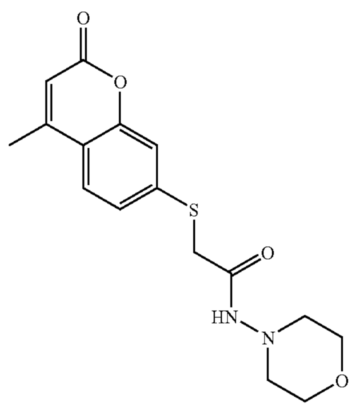 | 0.94 | N |
| Compound 26 | 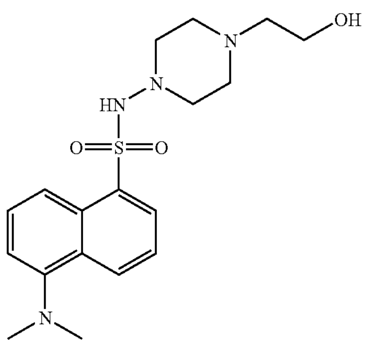 | 1.92 | Y |
| Compound 27 | 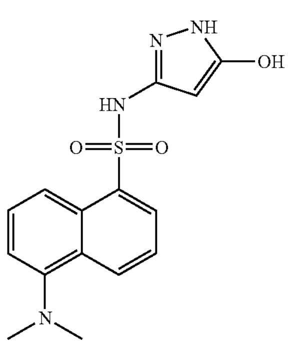 | 2.34 | Y |

TABLE 2-continued

Compounds exhibiting concentrative uptake in white cells

| Substrate | Structure | cLogP | Concentrative uptake |
|---|---|---|---|
| Compound 28 | 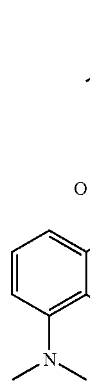 | 1.11 | Y |
| Compound 29 | 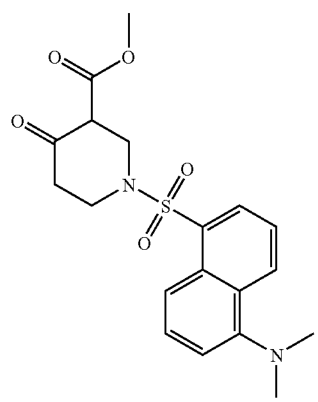 | 1.77 | N |
| Compound 30 | 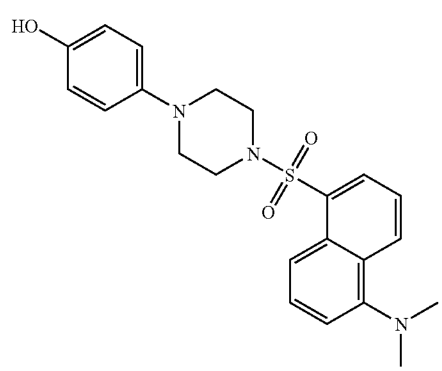 | 4.04 | N |
| Compound 31 | 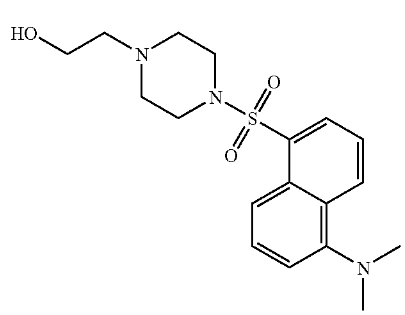 | 1.83 | N |

TABLE 2-continued

Compounds exhibiting concentrative uptake in white cells

| Substrate | Structure | cLogP | Concentrative uptake |
|---|---|---|---|
| Compound 32 | 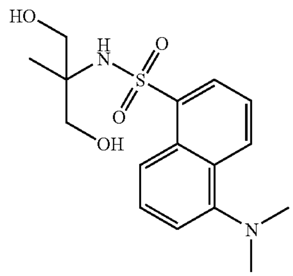 | 2.28 | N |
| Compound 33 | 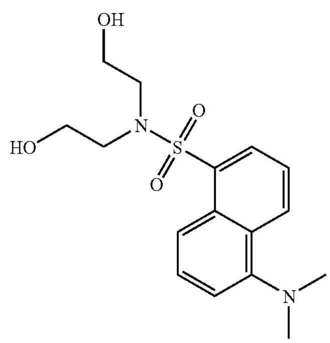 | 1.56 | N |
| Compound 34 | 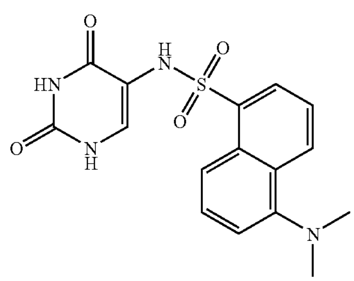 | 0.46 | N |
| Compound 35 | 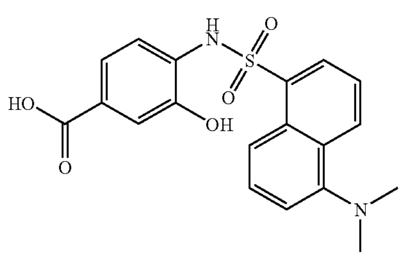 | 2.88 | N |
| Compound 36 | 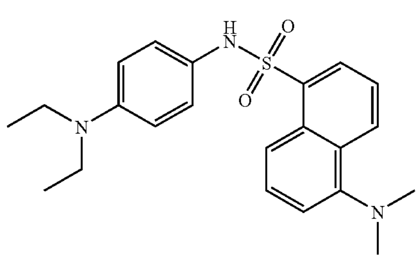 | 4.68 | N |

TABLE 2-continued

Compounds exhibiting concentrative uptake in white cells

| Substrate | Structure | cLogP | Concentrative uptake |
|---|---|---|---|
| Compound 37 | 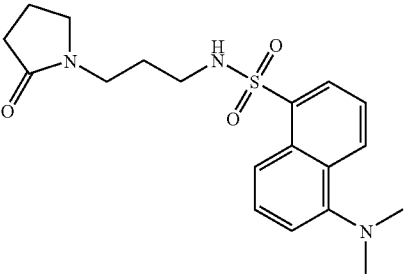 | 3.56 | N |
| Compound 38 | 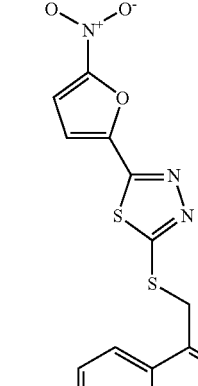 | n.d. | N |

Transportophores

Example 2

Compound 39

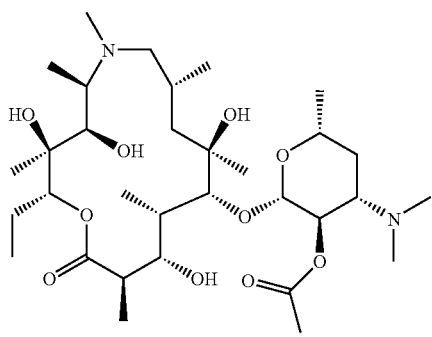

15.8 g (21.1 mmol) Azithromycin (9a-aza-9a-methyl-9-deoxo-9a-homoerythromycin A, Compound 43) was dissolved in an icecold 6 N hydrogen chloride solution (100 ml). The reaction mixture was stirred at 0° C. for 4 hours. The solution turned from yellow to green. The solution was poured on ice (200 g) and 28 ml sodium hydroxide solution (50%) were added. The solution was extracted with ethylacetate (300 ml). The organic layer was discarded. After addition of 30 ml sodium hydroxide solution (50%) to the water layer a colorless precipitate formed. The suspension was extracted with dichloromethane (300 ml). The organic layer was separated, dried over $Na_2SO_4$ and concentrated under reduced pressure. After drying in high vacuum 12.8 g (100%) of a colorless foam were obtained which were used without further purification.

The product was dissolved in dry dichloromethane (150 ml) and 3.1 ml (32.7 mmol) acetic acid anhydride were added. The solution was stirred at room temperature overnight, then diluted with dichloromethane (200 ml) and washed with saturated sodium bicarbonate solution (150 ml). The organic layer was separated, dried over $Na_2SO_4$ and concentrated under reduced pressure. 12.3 g (92%) of compound 39 were obtained as a colorless foam, which was dried in high vacuum and used without further purification.

Example 3

Compound 40

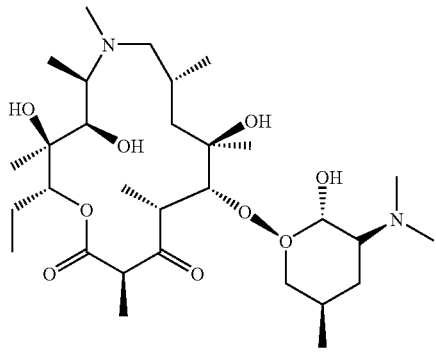

A solution of 610 mg (4.5 mmol) N-chlorosuccinimide in dry dichloromethane (50 ml) was chilled to -30° C. and 0.59 ml (8 mmol) dimethylsulfide were added. A colorless precipitate formed immediately and the suspension was kept between -30° C. and -10° C. for 30 min. Then the reaction mixture was cooled to -40° C. and 1.9 g (3.0 mmol) of compound 43 were added in one portion. After 20 min the precipitate was completely dissolved and 0.77 ml (4.5 mmol) of ethyl diisopropylamine were added to the colorless solution. The reaction mixture was allowed to reach ambient temperature slowly. Stirring was continued at room temperature for another hour. The reaction mixture was diluted with $CH_2Cl_2$ (50 ml) and washed with saturated sodium bicarbonate solution (100 ml). The organic layer was separated, dried over $Na_2SO_4$ and concentrated under reduced pressure. A colorless oil was obtained which was redissolved in methanol (75 ml) and stirred at 50° C. overnight. The solvent was removed under reduced pressure and the residue subjected to column chromatography on silica gel with chloroform/methanol/7N ammonia in methanol (20:1:1) as eluent to yield 1.0 g (59%) of compound 40 as a colorless oil.

Example 4

Compound 41

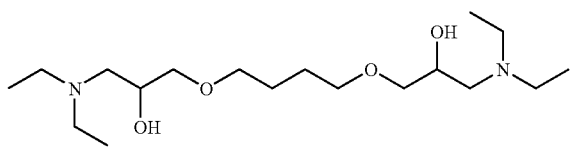

To a solution of 35 ml of diethylamine in 50 ml of ethanol was added 1.5 ml of 1,4-butandioldiglycidyl ether. The solution was allowed to stand for 48 h at ambient temperature. All volatiles were evaporated then and the residue used without further purification.

Example 5

Compound 42

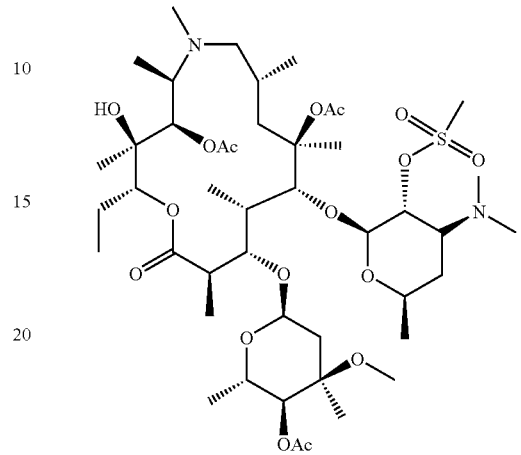

A solution of 15 g (20 mmol) of Compound 43 in 50 ml of acetic anhydride is treated with 2 g of potassium carbonate and heated to reflux for 3 h. After cooling the mixture is poured onto ice and neutralized with potassium carbonate. The mixture is extracted with ethyl acetate, washed with water and brine and concentrated after drying ($Na_2SO_4$). The residue is redissolved in methanol and heated to 50° C. overnight. After removal of the methanol in vacuum the residue id redissolved in chloroform. Triethylamine (10 ml) is added and the solution cooled to 0° C. Under stirring methansulfonic acid chloride (4.6 ml, 60 mmol) is added within 15 min and the mixture is allowed to warm to ambient temperature. After 3 h the mixture is washed with aqueous potassium carbonate solution and brine, dried ($Na_2SO_4$) and concentrated in vacuum. The residue is chromatographed on silica gel, elution with ethyl acetate to yield 3.5 g (22%) of slightly yellowish foam that is used without further purification.

Example 6

Compound 44

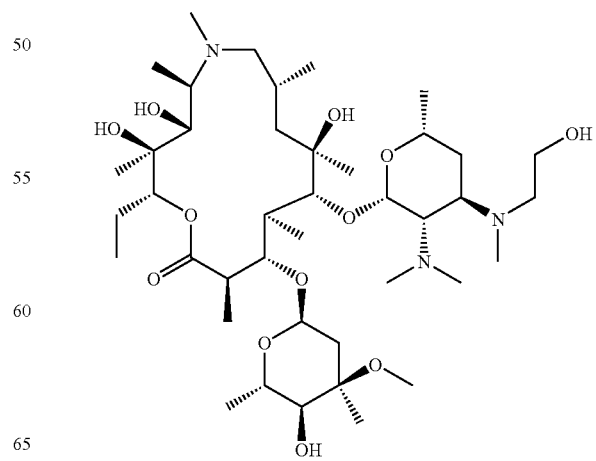

To a solution of Compound 42 (850 mg, 1 mmol) in DMF (7 mL), prepared as described before, N-methyl amino-2-ethanol (0.12 ml, 2 mmol) is added. After stirring for 24 h at 70° C. the mixture is concentrated in vacuum and the residue is dissolved in ethyl acetate, washed with water and brine, dried (Na$_2$SO$_4$) and the solvent evaporated in vacuum to yield 644 mg (80%) of yellowish foam that can be used without further purification.

Example 7

Compound 45

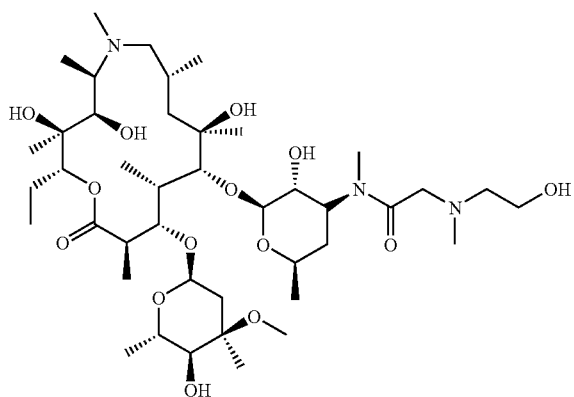

A solution of 1.1 g (1.5 mmol) of Compound 96 (See Example 24) in 5 ml of dichloromethane was combined with 415 mg (2.25 mmol) of iodo acetic acid and 450 mg (2.25 mmol) of DCC. After 2 h at ambient temperature the mixture was filtered and used without purification or concentration.

Example 8

Compound 46

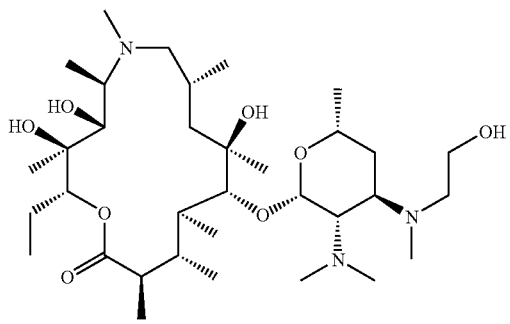

A solution of 2.0 g (2.5 mmol) of Compound 44 in 50 ml of 6 M HCl is kept for 15 min at ambient temperature and then extracted with 10 ml of ethyl acetate. The organic phase is discarded and the aqueous phase neutralised with potassium carbonate and extracted with ethyl acetate. The combined organic phases are dried (Na$_2$SO$_4$) and concentrated in vacuum to yield 1.47 g (91%) of a slightly yellowish solid that is used without further purification.

Example 9

Compound 47

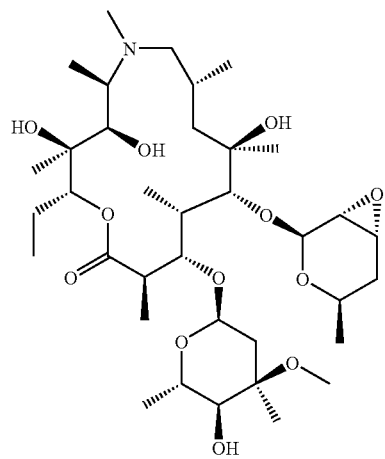

To a solution of 3.75 g (5.0 mmol) of Compound 43 in 5 ml of DMF is added 2.5 ml of epichlorohydrin and the mixture is heated to 60-65° C. for 2 d. After cooling most of the volatiles are removed in vacuum and the residue poured onto water and extracted with ethyl acetate. The combined organic phases are washed with brine, dried (Na$_2$SO$_4$) and concentrated in vacuum. The residue is chromatographed on silica gel, elution with ethyl acetate to yield 1.4 g (40%) of a colorless waxy solid.

Example 10

Compound 48

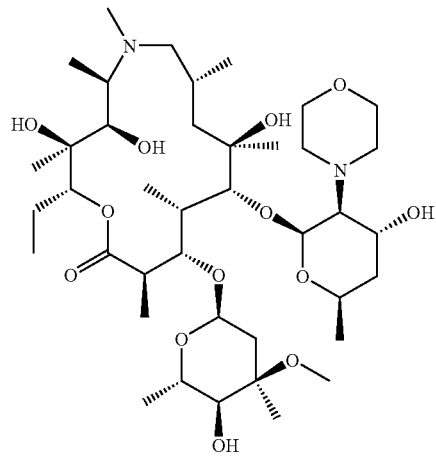

A solution of 1.5 g (2.1 mmol) of Compound 47 and 2 ml of morpholine in 15 ml of isopropanol is heated to reflux for 12 h. The mixture is cooled, poured onto water and extracted with ethyl acetate. The organic phase is washed with water, then with brine, dried (Na$_2$SO$_4$) and concentrated in vacuum.

The yellowish residue can be used without further purification, or purified by chromatography on silica gel, and eluted with chloroform/isopropanol/ammonia 20:1:1.

Example 11

Compound 49

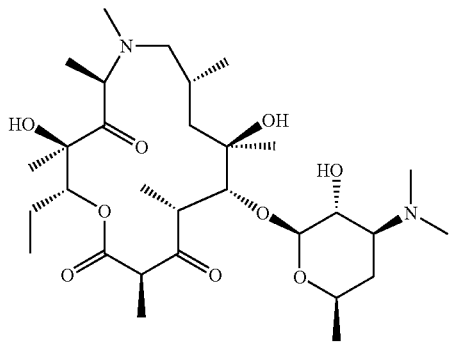

A solution of 1.63 g (12.0 mmol) N-chlorosuccinimide in dry dichloromethane (50 ml) was chilled to −40° C. and 1.3 ml (18 mmol) dimethylsulfide were added. A colorless precipitate formed immediately and the suspension was kept at −20° C. for 30 min. The reaction mixture was cooled to −40° C. and 1.9 g (3.0 mmol) of compound 43 prepared as described above were added in one portion. After 15 min 2.0 ml (12.0 mmol) of ethyl diisopropylamine were added. The precipitate dissolved and the solution was allowed to reach ambient temperature slowly. Stirring was continued at room temperature for 1 hour. The reaction mixture was diluted with $CH_2Cl_2$ (50 ml) and washed with saturated sodium bicarbonate solution (100 ml). The organic layer was separated, dried over $Na_2SO_4$ and concentrated under reduced pressure. A colorless oil was obtained which was redissolved in methanol (75 ml) and stirred at 50° C. overnight. The solvent was removed under reduced pressure and the residue subjected to column chromatography on silica gel with chloroform/methanol/7N ammonia in methanol (30:1:1) as eluent to yield 1.1 g (62%) of compound 49 as a colorless foam.

Example 12

Compound 50

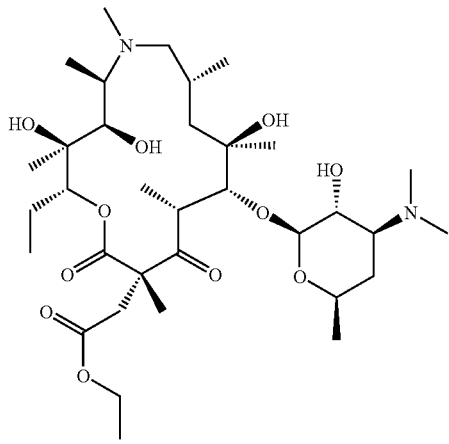

To a stirred solution of 589 mg (1 mmol) of Compound 40 in methanol (20 ml) was added 1.26 ml (10 mmol) of hydrogen peroxide (30%). After stirring for 3 days at room temperature the reaction mixture was chilled to −78° C. and a solution of 1.26 g (10 mmol) sodium sulfite in 10 ml of water was added. The suspension was allowed to warm up to room temperature and then all volatile compounds removed under reduced pressure. The residue was resuspended in methanol and filtered. The filtrate was concentrated under reduced pressure to furnish the crude product. Column chromatography on silica gel with chloroform/methanol/7N ammonia in methanol (15:4:1) as the eluent yielded 327 mg (54%) of compound 51 as a colorless oil.

To a stirred solution of 870 mg (1.4 mmol) of Compound 51 in dry N,N'-dimetylacetamide (20 ml) was added 370 mg (3.3 mmol) potassium tert-butoxide. The colorless solution turned slowly orange and was chilled to −15° C. 0.25 ml (2.2 mmol) ethyl bromoacetate were added and the reaction mixture allowed to warm up to room temperature. 2.0 ml of triethylamine were added and stirring continued for another hour. The reaction mixture was diluted with ethanol (20 ml) and acetic acid (2.0 ml) and 0.3 g of Pd/C (10%) were added. The reaction mixture was shaken under an atmosphere of hydrogen overnight. After filtration all volatile compounds were removed under reduced pressure. The crude product was subjected to column chromatography on silica gel with chloroform/methanol/7N ammonia in methanol (15:1:1) as the eluent to yield 340 mg (35%) of compound 50 as a colorless oil.

Acids

Example 13

Diclofenac Conjugates Compound 52

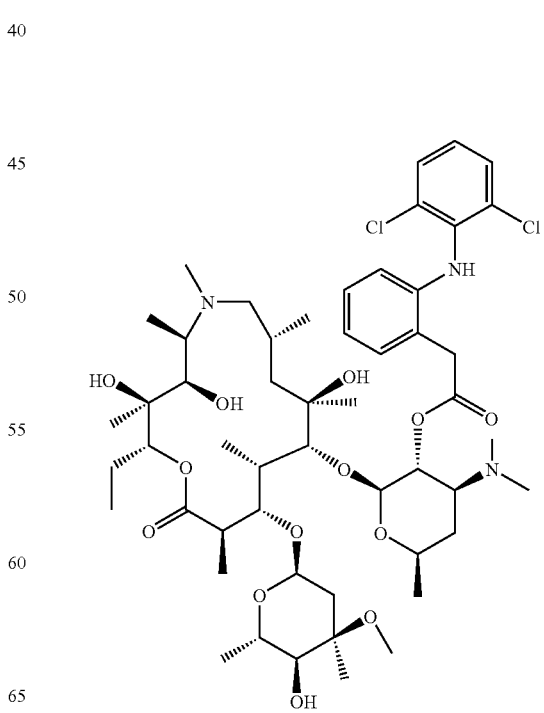

A solution of Diclofenac (0.67 g; 2.25 mmol) in methylene chloride (10 ml), is treated with N,N'-carbonyldiimidazole (0.38 g; 2.25 mmol). After stirring for 30 min at RT, Compound 43 (0.57 g; 0.75 mmol) is added. Reaction is stirred for 3 h at RT. The reaction solution was concentrated in vacuum and the residue purified by column chromatography on silica gel, elution with chloroform/isopropanol/methanolic ammonia 60:1:1 to yield Compound 52 (0.15 g; yield: 20%) as a white foam.

Compound 53

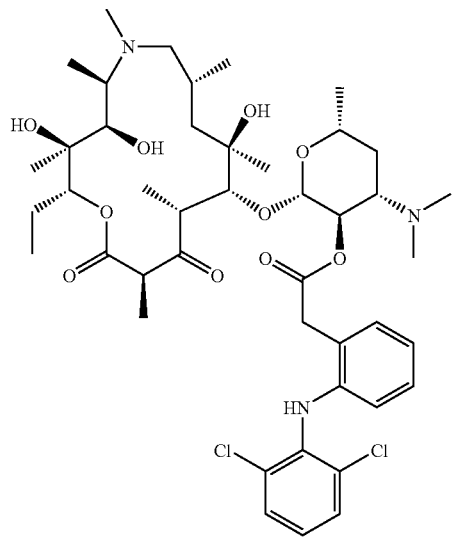

A suspension of 590 mg (2.0 mmol) of diclofenac in 6 ml of dichloromethane is treated with 324 mg (2.0 mmol) of carbonyl diimidazole at 0° C. After 5 min at this temperature 294 mg (0.5 mmol) of Compound 40 is added and the mixture kept at ambient temperature for 48 h. The mixture is then concentrated and the residue chromatographed on silica gel, elution with chloroform/isopropanol/methanolic ammonia 40:1:1 to yield 330 mg (76%) of a colorless solid.

Compound 54

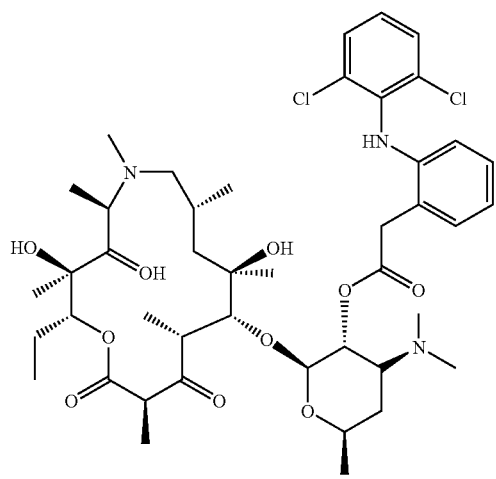

To a turbid solution of 740 mg (2.5 mmol) diclofenac in dry dichloromethane (20 ml) was added a solution of 1N hydrogen chloride in ether (2.5 ml) and 440 mg (2.7 mmol) of 1,1'-carbonyldiimidazole. The solution was stirred for 60 min at room temperature. Then 587 mg (1 mmol) of Compound 49 were added and stirring continued overnight. The mixture was diluted with CH$_2$Cl$_2$ (30 ml) and washed with saturated sodium bicarbonate solution (50 ml). The organic layer was separated, dried over Na$_2$SO$_4$ and concentrated under reduced pressure to furnish a reddish oil. Column chromatography on silica gel with chloroform/methanol/7N ammonia in methanol (30:1:1) as eluent yielded 450 mg (52%) of compound 54 as a colorless oil.

Compound 55

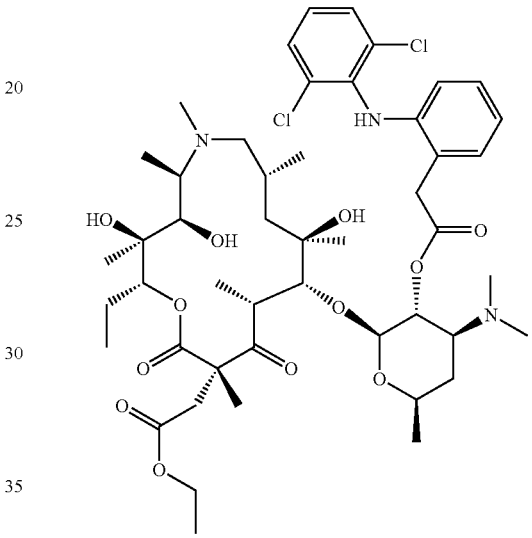

To a turbid solution of 740 mg (2.5 mmol) diclofenac in dry dichloromethane (20 ml) was added a solution of 1N hydrogen chloride in ether (2.5 ml) and 440 mg (2.7 mmol) of 1,1'-carbonyldiimidazole. The solution was stirred for 60 min at room temperature. Then 340 mg (0.5 mmol) of compound 50 prepared as described above were added and stirring continued overnight. The mixture was diluted with CH$_2$Cl$_2$ (30 ml) and washed with saturated sodium bicarbonate solution (50 ml). The organic layer was separated, dried over Na$_2$SO$_4$ and concentrated under reduced pressure to furnish a reddish oil. Column chromatography on silica gel with chloroform/methanol/7N ammonia in methanol (10: 1:1) as eluent yielded 214 mg (45%) of compound 55 as a colorless oil.

Example 14

Compound 56

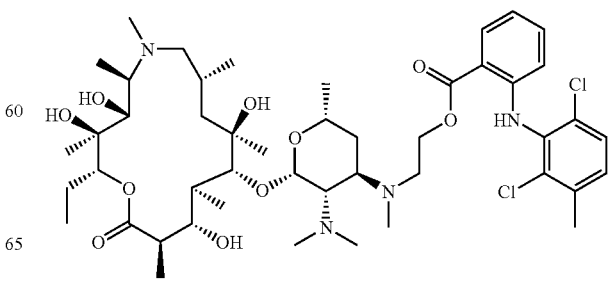

A solution of Meclofenamic acid (0.36 g; 1.2 mmol) in methylene chloride (15 ml), is treated with N,N'-carbonyldiimidazole (0.20 g; 1.2 mmol). After stirring for 30 min at RT, Compound 44 (0.47 g; 0.75 mmol) is added. Reaction is stirred for 3 h at RT. The reaction solution is concentrated in vacuum and the residue purified by column chromatography on silica gel, elution with chloroform/isopropanol/methanolic ammonia 60:1:1. The appropriate fractions are collected and concentrated to yield 0.17 g (25%) of Compound 56 as a white foam.

Example 15

Compound 57

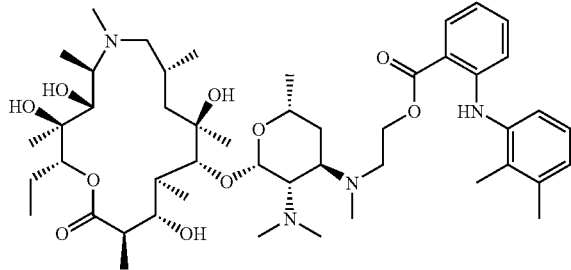

A solution of Mefenamic acid (0.29 g; 1.2 mmol) in methylene chloride (5ml), is treated with N,N'-carbonyldiimidazole (0.20 g; 1.2 mmol). After stirring for 30 min at ambient temperature, Compound 44 (0.47 g; 0.75 mmol) is added. Reaction is stirred for 3 h at ambient temperature. The reaction solution is concentrated in vacuum and the residue purified by column chromatography, elution with chloroform/isopropanol/methanolic ammonia 60:1:1. The appropriate fractions are collected and concentrated to produce Compound 57 (0.16 g; yield: 25%) as a white foam.

Example 16

Compound 58

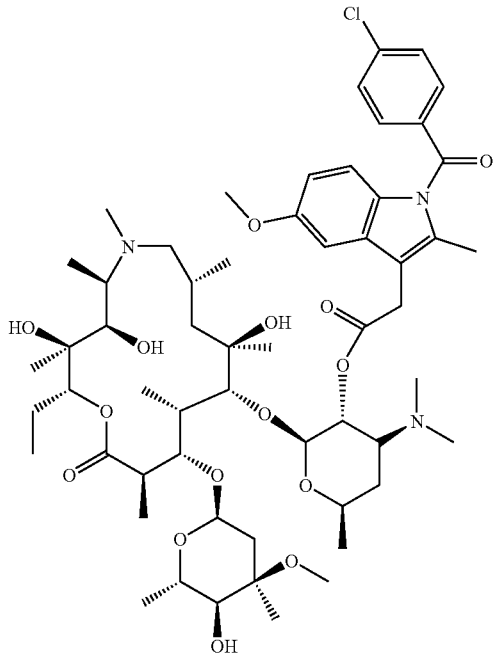

A solution of Indomethacin (0.80 g; 2.25 mmol) in methylene chloride (10 ml), is treated with N,N'-carbonyldiimidazole (0.38 g, 2.25 mmol). After stirring for 30 min at RT, Compound 40 (0.44 g; 0.75 mmol) is added. Reaction is stirred for 3 h at RT. The reaction solution was concentrated in vacuum and the residue purified by column chromatography on silica gel, elution with isopropanol to yield 0.20 g (25%) of Compound 58 a white foam.

Example 17

Compound 59

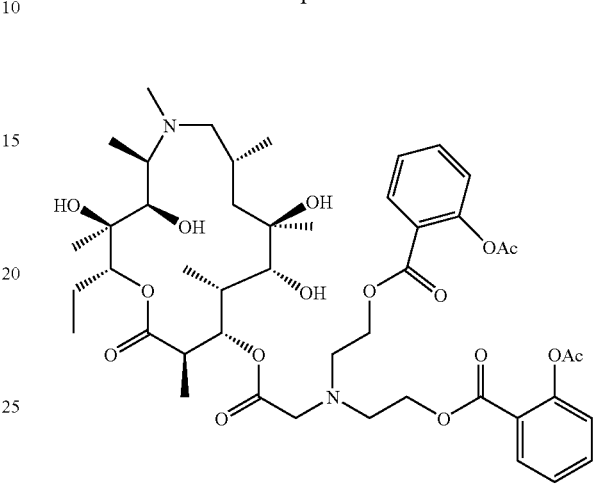

A solution of 360 mg (2.0 mmol) of acetyl salicylic acid is treated with 1.5 ml (16 mmol) oxalylic chloride in 10 ml of chloroform. A drop of DMF is added and the mixture is allowed to stand at ambient temperature for 1 h. All volatiles are removed in vacuum and the residue dissolved in 20 ml of dichloromethane. After cooling to 0° C. 376 mg (0.65 mmol) of Compound 104 (See Example 24) is added followed by 1 ml of pyridine. The mixture is allowed to warm to ambient temperature and after 2 h concentrated in vacuum. The residue is chromatographed on silica gel, elution with chloroform/isopropanol/methanolic ammonia 60:1:1 to yield 205 mg (35%) of Compound 59 as a white solid.

Example 18

Compound 60

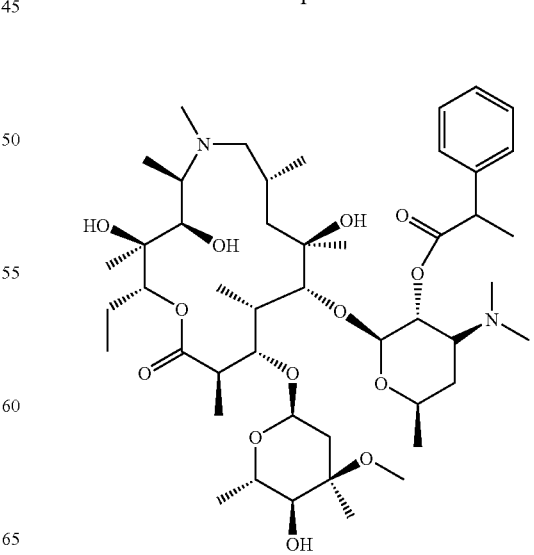

A solution of Ibuprofen (0.47 g; 2.25 mmol) in methylene chloride (10 ml), is treated with N,N'-carbonyldiimidazole (0.38 g, 2.25 mmol). After stirring for 30 min. at RT, Compound 43 (0.56 g; 0.75 mmol) is added. Reaction is stirred for 3 h at RT. The reaction solution was concentrated in vacuum and the residue purified by column chromatography on silica gel, elution with isopropanol to yield 0.17 g (25%) of white foam, Compound 60.

Example 19

Compound 61

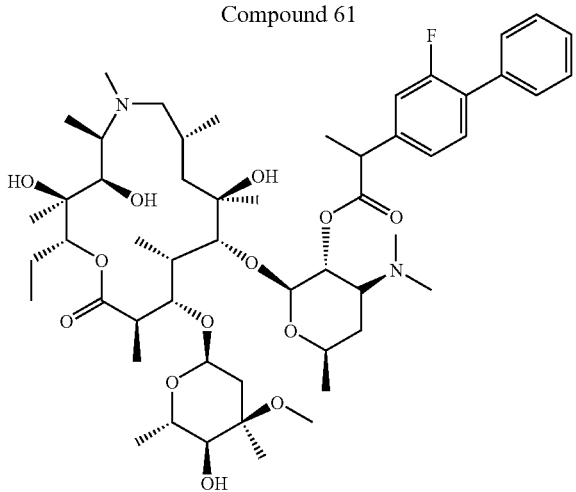

A solution of flurbiprofen (0.27 g; 1.2 mmol) in methylene chloride (5 ml), is treated with N,N'-carbonyldiimidazole (0.20 g; 1.2 mmol). After stirring for 30 min. at ambient temperature, Compound 46 (0.47 g; 0.75 mmol) is added. Reaction is stirred for 3 h at ambient temperature. The reaction solution was concentrated in vacuum and the residue purified by column chromatography on silica gel, and elution with chloroform/isopropanol/methanolic ammonia 60:1:1 to yield 0.16 g (25%) of product Compound 61, a white foam.

Example 20

Compound 62

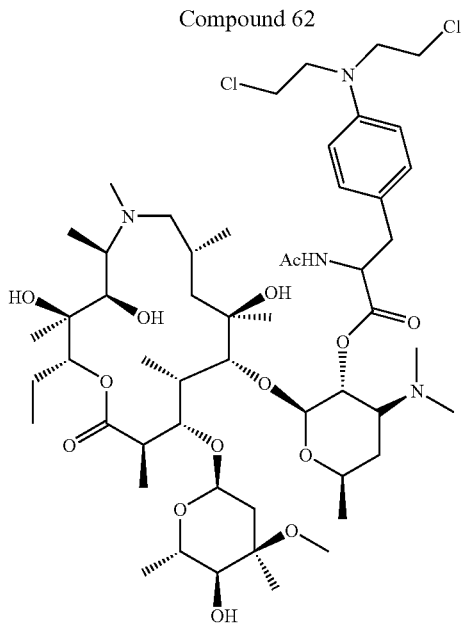

600 mg of melphalan (63) is suspended in 25 ml of water containing 500 mg of sodium carbonate. 10 ml of dioxane is added and 1 ml of acetic anhydride. After stirring at ambient temperature for 1 h citric acid is added and the mixture extracted with ethyl acetate. After washing with water and brine the organic phase is dried (sodium sulfate) and concentrated in vacuum. Removal of all volatiles yields the crude N-acetylmelphalan that is carried on to the next step without further purification.

A solution of N-acetylmelphalan (0.35 g; 1.0 mmol) dissolved in methylene chloride (5ml), is treated with N,N'-carbonyldiimidazole (0.17 g; 1.0 mmol). After stirring for 30 min. at RT, Compound 43 (0.29 g; 0.50 mmol) is added. After 3 h the reaction solution is concentrated in vacuum and the residue purified by column chromatography on silica gel, elution with chloroform/isopropanol/methanolic ammonia 60:1:1. The appropriate fractions are collected and concentrated to produce 0.12 g (25%) of Compound 62 as a white foam.

Example 21

Compound 64

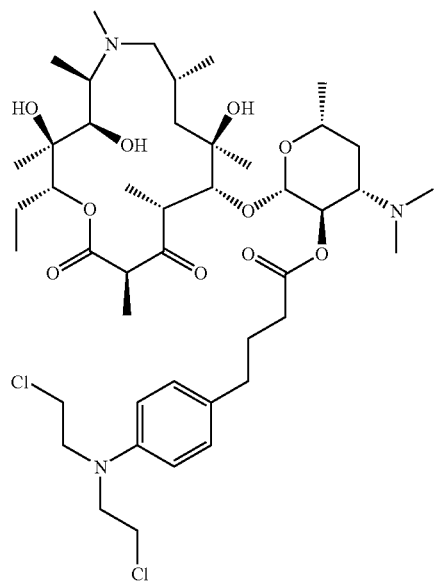

To a solution of chlorambucil (303 mg; 1 mmol) in methylene chloride (5 ml), is added N,N'-carbonyldiimidazole (130 mg; 1 mmol). After 30 min stirring at ambient temperature, Compound 43 (750 mg; 1 mmol) is added. After stirring at the same temperature for 3 h the mixture is washed with ice water and ice cold $Na_2CO_3$ solution. The organic layer is dried (Na2SO4), concentrated in vacuum and chromatographed on silica gel, elution with isopropanol to afford 207 mg (20%) of a white foam, Compound 64, MS (M+2H$^+$: 517).

Example 22

Compound 65

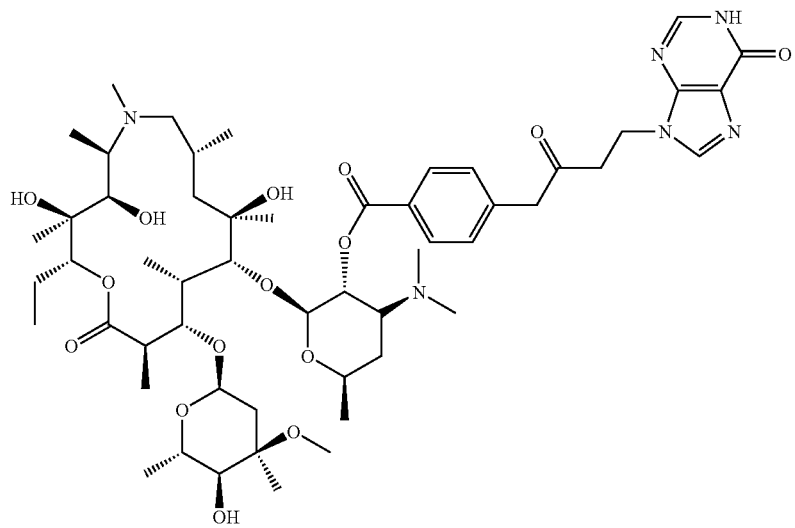

A suspension of neotrofin (0.73 g; 2.25 mmol) in methylene chloride (15 ml), is treated with N,N'-carbonyldiimidazole (0.38 g; 2.25 mmol). After stirring for 2 h at ambient temperature Compound 43 (0.57 g; 0.75 mmol) is added. Reaction is stirred for 48 h at ambient temperature. The reaction solution is concentrated in vacuum and the residue purified by column chromatography on silica gel, elution with chloroform/isopropanol/methanolic ammonia 60:1:1. The appropriate fractions are collected and concentrated to produce Compound 65 (0.20 g; yield: 25%) as a white foam.

Example 23

Compound 66

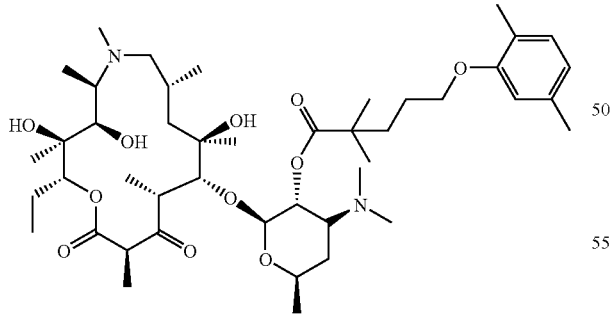

A solution of Gemfibrozil (0.56 g; 2.25 mmol) in methylene chloride (10 ml), is treated with N,N'-carbonyldiimidazole (0.38 g; 2.25 mmol). After stirring for 30 min. at ambient temperature, Compound 40 (0.44 g; 0.75 mmol) is added. Reaction is stirred for 48 h at ambient temperature. The reaction solution was concentrated in vacuum and the residue purified by column chromatography on silica gel, elution with chloroform/isopropanol/methanolic ammonia 60:1:1. The appropriate fractions are collected and concentrated to produce Compound 66 (0.15 g; yield: 25%) as a white foam.

Example 24

Mycophenolate Derivatives

Compound 67

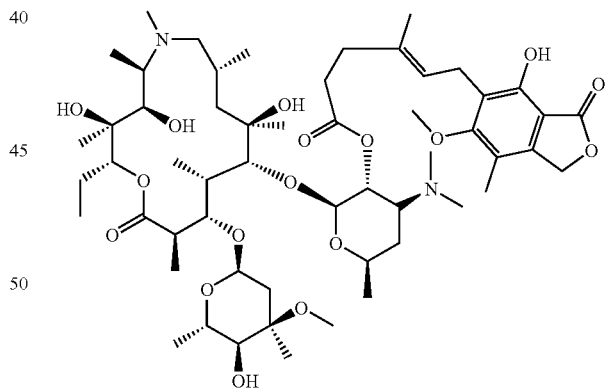

To a mixture of 375 mg of Compound 43, 400 mg of triphenyl phosphine and 960 mg of mycophenolic acid is added 4 ml of THF under nitrogen. Diisopropyl azodicarboxylate (0.3 ml) is added drop wise at 0° C. within 4 h while the reaction mixture is rapidly stirred. Cooling is continued for another 4 h and the mixture then allowed to warm to ambient temperature within 5 h. The mixture is then dissolved in a mixture consisting of 50 ml of toluene and 20 ml of ethyl acetate and extracted with ice-cold 0.5 M hydrogen chloride (3×150 ml). The aqueous phase is washed several times with small amounts of toluene and then with potassium carbonate till no foaming occurs any more upon addition. The mixture is extracted with dichloromethane and the organic phase is washed with brine, dried and concentrated in vacuum to yield white solid foam that can be used without further purification, or further purified on a silica gel column, eluting with isopropanol.

Compound 68

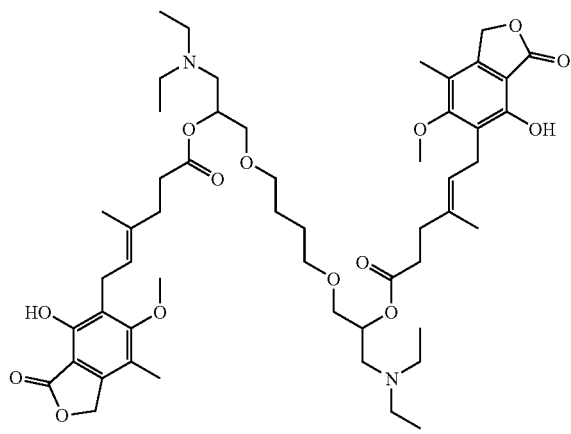

To a solution of 170 mg of Compound 41, 400 mg of triphenylphosphine and 500 mg of mycophenolic acid in 3 ml of THF were added under nitrogen 0.3 ml of diisopropyl azodicarboxylate within 4 h at 0°. The mixture was allowed to stir at 0° C. for 3 h and was then allowed to warm to ambient temperature slowly. The reaction mixture was diluted with 70 ml of toluene and 30 ml of ethyl acetate and extracted repeatedly with ice-cold 0.5 M hydrogen chloride. The combined aqueous phases were extracted several times with a small quantity of toluene. The organic phases were discarded. The aqueous phase was treated with potassium carbonate till gas evolution had stopped and was then extracted with dichloromethane. Drying (sodium sulfate) and concentration in vacuum yielded an oily residue that was purified by filtration through a short pad of silica gel (elution with ethyl acetate-triethylamine) to afford 185 mg (39%).

Compound 69

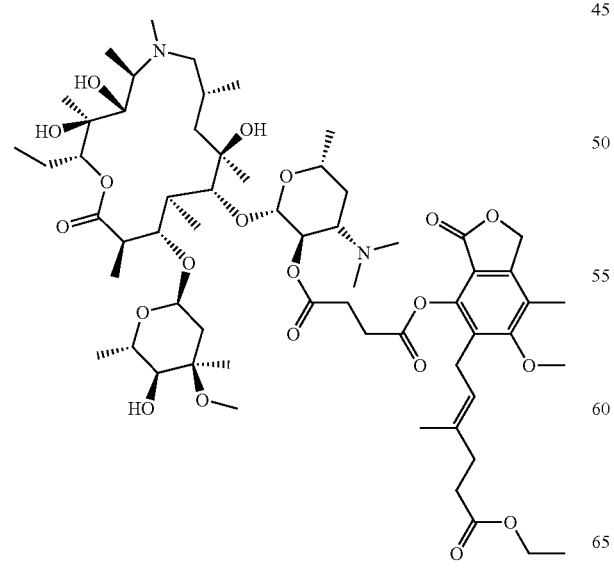

A solution of 750 mg (1.0 mmol) of Compound 43 in 10 ml of dichloromethane is treated with 100 mg (1.0 mmol) of succinic anhydride. After stirring at ambient temperature for 12 h the mixture is concentrated in vacuum to yield Compound 70, a colorless solid that is used with out further purification.

To a solution of mycophenolic acid ethyl ester (175 mg, 0.5 mmol) in chloroform (1 ml) is added ethyldiisopropylamine (85 µL, 0.5 mmol). After stirring for 1 min Compound 70 (425 mg, 0.5 mmol) is added under nitrogen at 0-4° C. and afterwards chlor-N,N,2-trimethylpropenamine (1 mL; 0.5 mmol; 0.5 mmol/mL solution in chloroform) is added drop-wise. The mixture is stirred at 0-4° C. for 0.5 h and 12 h at room temperature. The mixture is concentrated in vacuum and the residue chromatographed on silica gel, elution with chloroform/2-propanol/ammonia 30:1:1, affording 147 mg (25%) of a colorless solid.

Compound 71

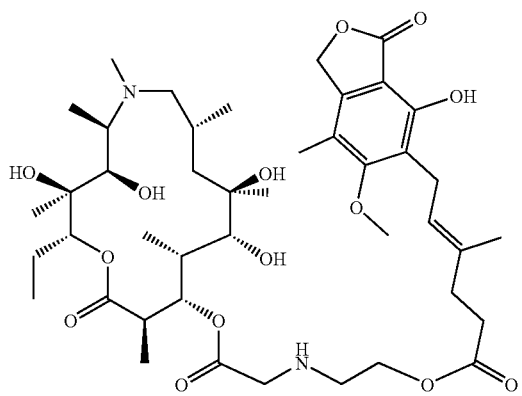

To mycophenolic acid (0.50 g; 1.5 mmol) and carbonyldiimidazole (0.25 g; 1.5 mmol), dissolved in methylene chloride (2 mL) is added after 1 minute stirring at 0-4° C. a solution of Compound 72 (0.27 g, 0.5 mmol) in 1 ml of dichloromethane. After stirring for 30 min at 0-4° C. the mixture is stirred for 12 h at room temperature. The mixture is concentrated in vacuum and the residue chromatographed on silica gel, elution with chloroform/2-propanol/ammonia 30:1:1, affording 98 mg (23%) of a colorless solid.

Compound 73

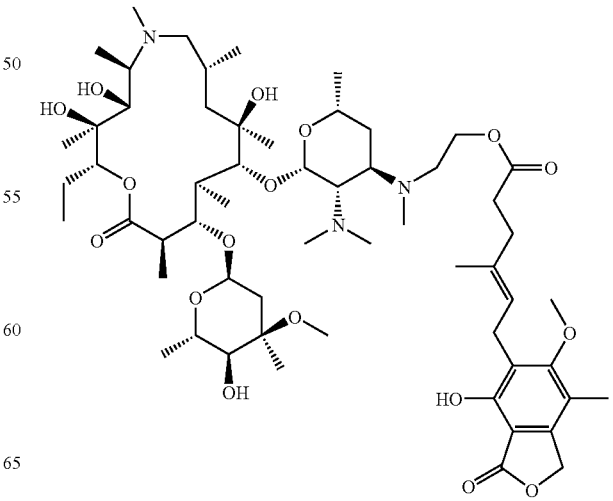

Mycophenolic acid (0.50 g; 1.5 mmol) is suspended in 3 ml of dichloromethane and treated with carbonyldiimidazole (0.25 g; 1.5 mmol). After 10 min a solution of Compound 44 (0.38 g; 0.5 mmol) in dichloromethane is added. After 30 min at 0° C. the mixture is stirred for 12 h at room temperature. The mixture is concentrated in vacuum and the residue chromatographed on silica gel, elution with chloroform/2-propanol/ammonia 30:1:1, affording 126 mg (22%) of a colorless foam.

Compound 74

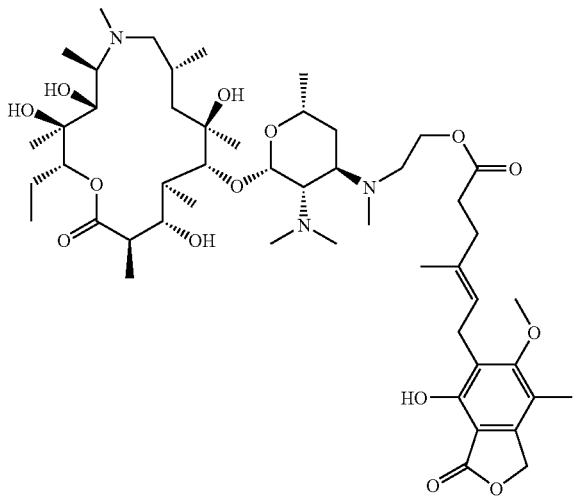

A solution of Compound 73 in 6 M HCl (20 ml) is kept at ambient temperature for 15 min and then extracted 5 ml of ethyl acetate. The organic phase is discarded and the aqueous phase neutralized with potassium carbonate and extracted with methylene chloride. The organic phase is dried (Na2SO4) and concentrated in vacuum to yield 400 mg (84%) of a colorless foam.

Compound 75

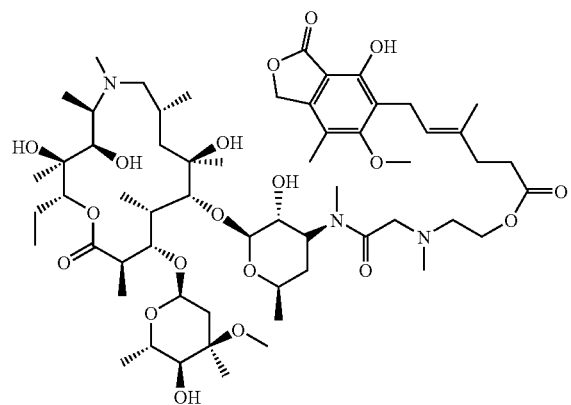

A solution of 1.1 g (1.5 mmol) of Compound 43 in 5 ml of dichloromethane was combined with 415 mg (2.25 mmol) of iodoacetic acid and 450 mg (2.25 mmol) of DCC. After 2 h at ambient temperature the mixture was filtered and the resulting Compound 76 was used without purification or concentration.

A solution 720 mg of (0.8 mmol) of Compound 76 in 3 ml of dichloromethane, prepared as described above, is diluted with 20 ml of DMF and 0.1 ml (1.2 mmol) of N-methyl amino ethanol is added. The mixture is kept at ambient temperature for 24 h. The mixture is poured onto a solution of potassium carbonate in water and extracted with dichloromethane. The organic phase is washed with brine, dried (Na2SO4 and concentrated in vacuum. The residue is chromatographed on silica gel, elution with chloroform/isopropanol/methanolic ammonia 80:1:1 to yield 210 mg (31%) of Compound 77, a colorless solid.

A suspension of mycophenolic acid (0.50 g; 1.5 mmol) in 8 ml of dichloromethane was treated with carbonyldiimidazole (0.25 g; 1.5 mmol at 0° C. After 10 min a solution of Compound 77 (0.40 g, 0.5 mmol) in 2 ml of dichloromethane was added. After stirring for 30 min. at 0-4° C. the mixture is stirred for 24 h at room temperature. The mixture is concentrated in vacuum and the residue chromatographed on silica gel, elution with chloroform/2-propanol/ammonia 30:1:1, affording 175 mg (32%) of Compound 75.

Compound 78

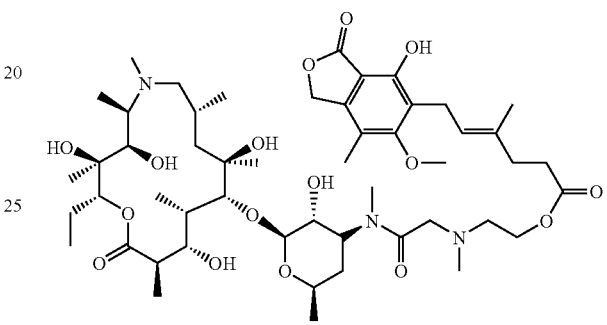

A solution of Compound 75 (550 mg, 0.5 mmol) prepared as described before in 20 ml of 6 M HCl is kept at ambient temperature for 10 min and then extracted with diethylether. The organic phase is discarded and the aqueous phase neutralized with potassium carbonate and extracted with dichloromethane. The organic phase is washed with brine, dried (Na$_2$SO$_4$) and concentrated in vacuum to yield 420 mg (89%) as a slightly yellowish foam.

Compound 79

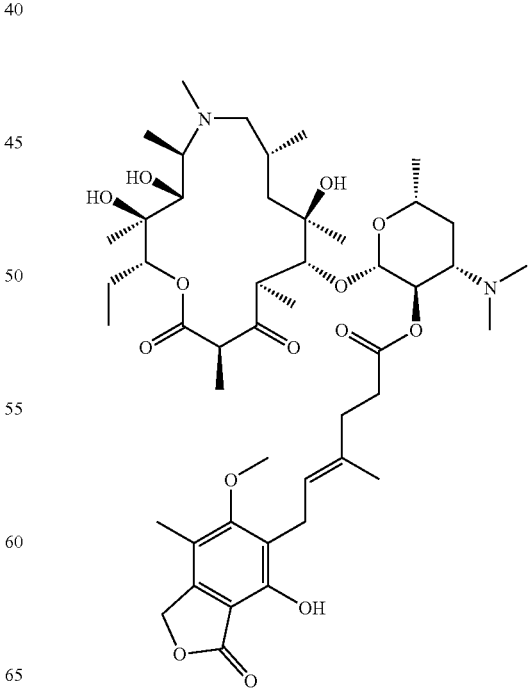

A suspension of mycophenolic acid (0.30 g; 0.9 mmol) in 8 ml of dichloromethane is treated with carbonyldiimidazole (0.15 g; 0.9 mmol) at 0° C. After 10 min a solution of Compound 40 (0.20 g, 0.3 mmol) in 2 ml of dichloromethane was added. After stirring for 30 min. at 0-4° C. the mixture is stirred for 24 h at room temperature. The mixture is concentrated in vacuum and the residue chromatographed on silica gel, elution with chloroform/2-propanol/ammonia 30:1:1, affording 100 mg (35%) of a colorless foam.

Compound 80

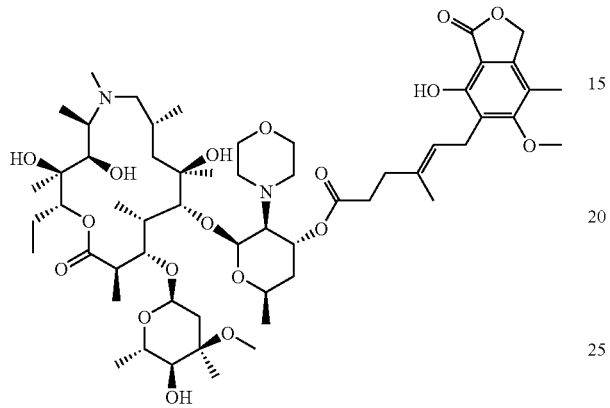

A mixture of 120 mg of Compound 48, 320 mg of mycophenolic acid and 300 mg of triphenyl phosphine is dissolved in 2 ml of THF under nitrogen. At 0° C. 0.1 ml (0.5 mmol) diisopropyl azodicarboxylate is added in several portions within 4 h. After this time the mixture is allowed to warm to ambient temperature overnight. The reaction mixture is concentrated in vacuum and chromatographed on silica gel, elution with isopropanol.

Compound 81

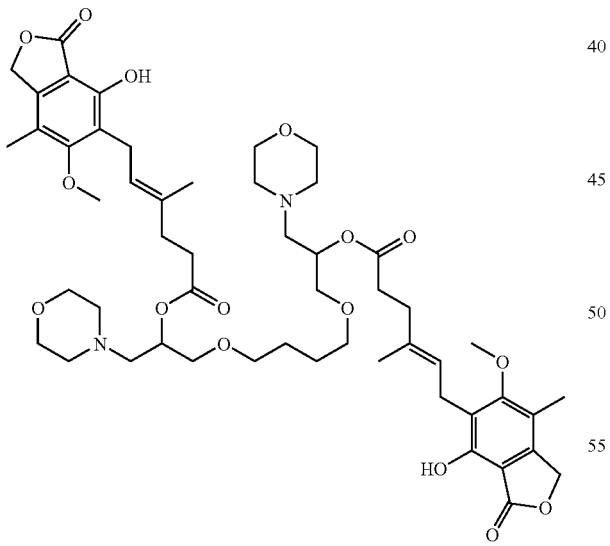

To a solution of 188 mg of Compound 41, 400 mg of triphenylphosphine and 500 mg of mycophenolic acid in 3 ml of THF were added under nitrogen 0.3 ml of diisopropyl azodicarboxylate within 4 h at 0° C. The mixture was allowed to stir at 0° C. for 3 h and was then allowed to warm to ambient temperature slowly. The reaction mixture was diluted with 70 ml of toluene and 30 ml of ethyl acetate and extracted repeatedly with ice-cold 0.5 M hydrogen chloride. The combined aqueous phases were extracted several times with a small quantity of toluene. The organic phases were discarded. The aqueous phase was treated with potassium carbonate until gas evolution had stopped and was then extracted with dichloromethane. Drying ($Na_2SO_4$) and concentration in vacuum yielded an oily residue that was purified by filtration through a short pad of silica gel (elution with ethyl acetate-triethyl amin) to yield 255 mg (52%) of a yellowish oil.

Example 25

Steroid Conjugates

Compound 82

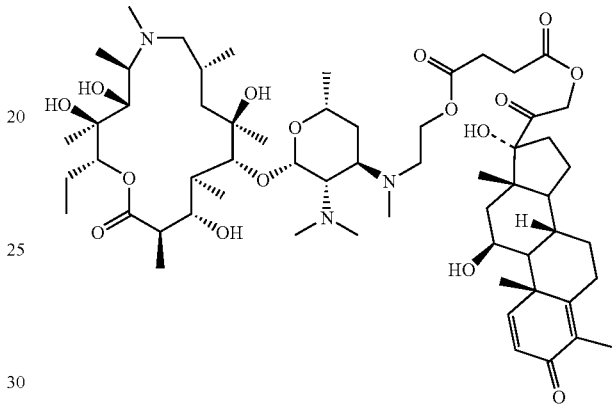

Prednisolone (180 mg, 0.5 mmol) is suspended in 3 ml of chloroform and 55 mg (0.55 mmol) of succinic anhydride is added. After 24 h at ambient temperature the mixture is cooled to 0° C. and 325 mg of Compound 46 (0.5 mmol) is added followed by chlor-N,N,2-trimethylpropenamine (0.2 ml, 1.5 mmol) in several portions. The resulting solution is subjected to column chromatography on silica gel, elution with isopropanol to yield a white solid.

Compound 83

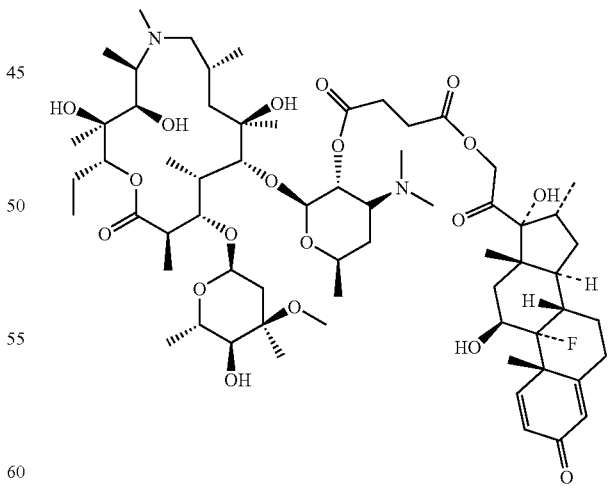

Dexamethasone (196 mg, 0.5 mmol) is suspended in 3 ml of chloroform and 55 mg (0.55 mmol) of succinic anhydride is added. After 24 h at ambient temperature 375 mg of Compound 43 (0.5 mmol) is added followed by chloro-N,N,2-trimethylpropenamine (0.2 ml, 1.5 mmol) in several portions. The resulting solution is after 1 h subjected to column chromatography on silica gel, elution with isopropanol to yield 198 mg (32%) of a white solid.

Compound 84

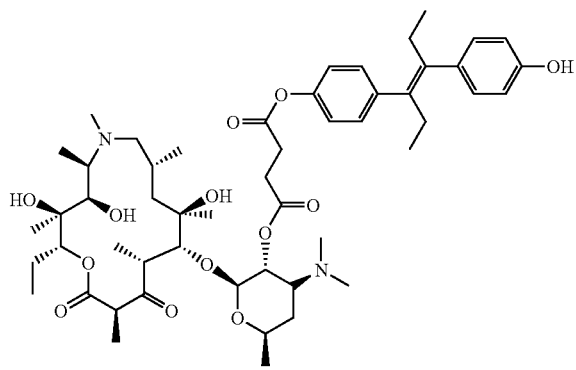

A solution of 295 mg (0.5 mmol) of Compound 40 in 4 ml of dichloromethane is treated with 55 mg (0.55 mmol) of succinic anhydride and the mixture stirred at ambient temperature overnight. To the reaction mixture diethylstilbestrol (174 mg, 0.5 mmol) and 0.15 ml of diisopropylethylamine is added followed by 0.133 ml of chloro-N,N,2-trimethylpropenamine (1.0 mmol) in several portions. After 1 h the reaction mixture is concentrated in vacuum and the residue chromatographed on silica gel, elution with ethyl acetate, changing to isopropanol, to yield 74 mg (16%) of a colorless solid.

Compound 85

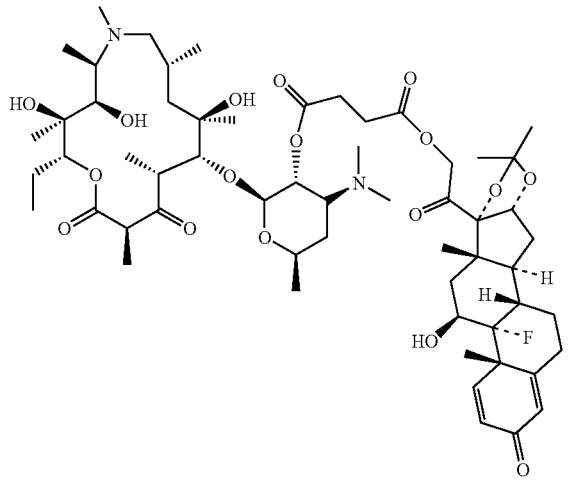

A solution of 217 mg (0.5 mmol) of triamcinolone acetonide, 55 mg (0.55 mmol) of succinic anhydride in 3 ml of dichloromthane and 1 ml of pyridine is reacted 2 d at ambient temperature. After this period all volatiles are removed and the residue taken up in THF. To this mixture 100 mg (0.62 mmol) of carbonyldiimidazole is added under nitrogen, followed by 300 mg (0.51 mmol) of Compound 40. The mixture was heated to 50° C. for 36 h. After cooling the mixture was concentrated in vacuum and the residue chromatographed on silica gel, elution with ethyl acetate, changing to isopropanol to yield 34 mg (6%) of a colorless solid.

Compound 86

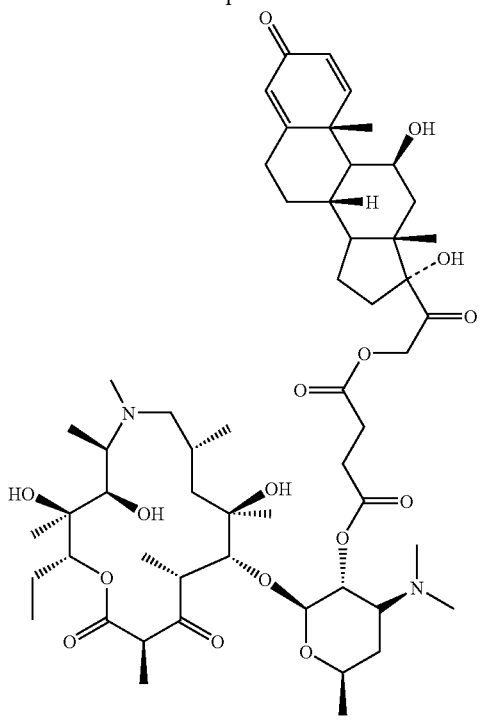

Prednisolone (180 mg, 0.5 mmol) is suspended in 3 ml of chloroform and 55 mg (0.55 mmol) of succinic anhydride is added. After 24 h at ambient temperature the mixture is cooled to 0° C. and 295 mg of Compound 40 (0.5 mmol) is added followed by chlor-N,N,2-trimethylpropenamine (0.2 ml, 1.5 mmol) in several portions. The resulting solution is subjected to column chromatography on silica gel, elution with isopropanol to yield 165 mg (32%) of a white solid Example 26

Statins

Compound 87

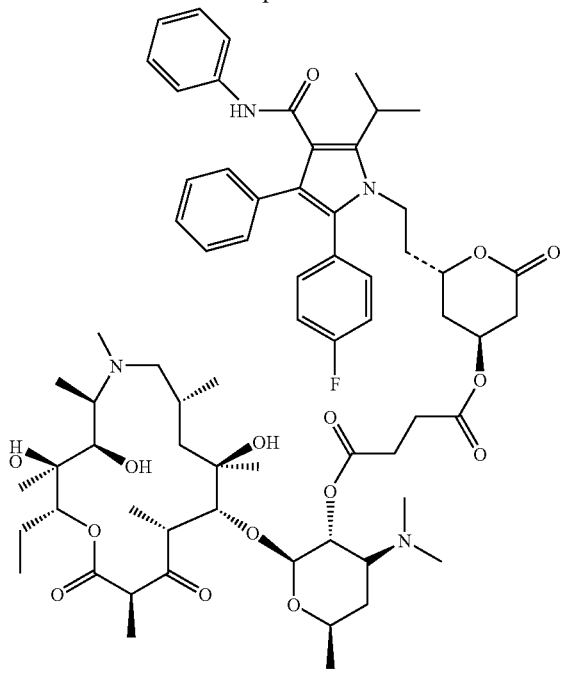

A solution of 560 mg (1 mmol) of atorvastatin in 10 ml of dichloromethane is treated with 2 ml of a 1 M solution of HCl in diethyl ether at ambient temperature for 12 h. The reaction mixture is washed with water and brine, dried (Na$_2$SO$_4$) and concentrated in vacuum. The residue is dissolved in 8 ml of chloroform and treated with 120 mg (1.2 mmol) of succinic anhydride and 123 mg (1.0 mmol) of DMAP under nitrogen. After 24 h at ambient temperature 194 mg (1.2 mmol) of carbonyldiimidazole is added, followed after 10 min by 700 mg (1.2 mmol) of Compound 40. The mixture is heated to 50° C. for 36 h and then cooled, concentrated in vacuum and chromatographed on silica gel, elution with chloroform/2-propanol/ammonia 30:1:1 to yield 125 mg (10%) of a colorless solid.

Compound 88

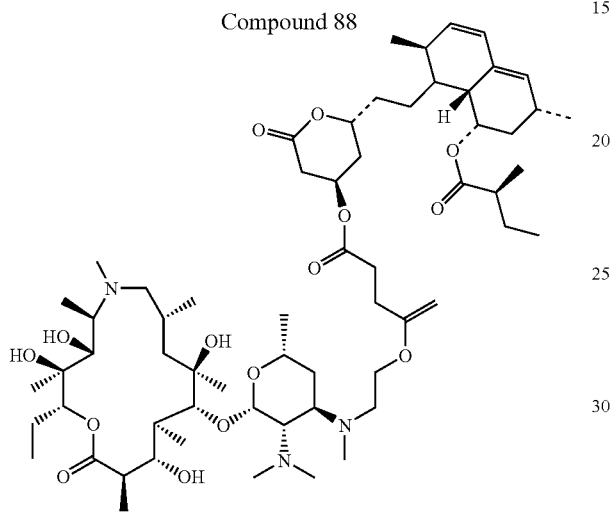

A solution of 25 mg (0.06 mmol) of lovastatin in 1 ml of dichloromethane was treated with 10 mg (0.1 mmol) of succinic anhydride under nitrogen. The mixture was kept at ambient temperature for 48 h and then 12 mg of carbonyldiimidazole is added followed after 10 min by 70 mg (0.11 mmol) of Compound 46. After stirring for 48 h at ambient temperature the mixture is concentrated in vacuum and the residue chromatographed on silica gel, elution with chloroform/2-propanol/ammonia 30:1:1 to yield 13 mg (19%) a white solid.

Example 27

Antifungal Conjugate

Compound 89

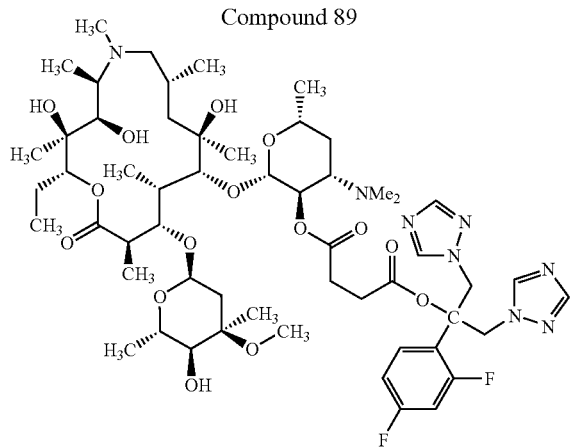

To a stirred solution of Fluconazole (0.67 g, 2.2 mmol) in anhydrous CH$_2$Cl$_2$ (20 ml) was added triethylamine (0.31 ml, 2.2 mmol) and succinic anhydride (0.22 g, 2.2 mmol). After stirring for 2 hours at ambient temperature N,N'-carbonyldiimidazole (0.37 g, 2.3 mmol) was added and stirred for another 2 hours. Subsequently Compound 43 (1.12 g, 1.5 mmol) was added and stirring continued overnight. Then the reaction mixture was diluted with CH$_2$Cl$_2$ (20 ml) und a saturated aqueous solution of sodium bicarbonate (30 ml). After separation, the organic layer was dried over Na$_2$SO$_4$, filtered and then concentrated under reduced pressure to furnish the crude product. Silica gel chromatography with THF-Hexane-NEt$_3$ (10:10:0.1) yielded Compound 89 as a white solid (0.20 g, 12%).

Alcohols

Example 28

Nucleosides

Compound 90

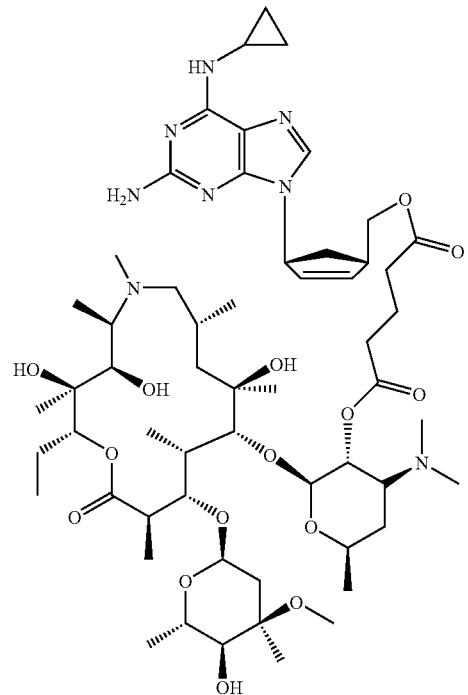

To a mixture of 800 mg glutaric acid (6 mmol, 6 eq.) and 500 mg CDI (3 mmol, 3 eq.) dissolved in 10 ml dry acetonitrile and stirred for 30 minutes at room temperature under argon, is added a solution of 750 mg Compound 43 (1 mmol) in the presence of a catalytic amount of DMAP dissolved in 5 ml acetonitrile. The reaction is refluxed overnight.

The solvent is removed in vacuo. The crude mixture is then purified by chromatography with chloroform/methanol/ammonia (94.5:10:0.5). The collected fractions yielded a white solid (340 mg, 45%). The expected Compound 91 is characterized by TLC (R$_f$=0.4 in chloroform/methanol/ammonia (90:9:1)) and by MS ([M+H]+=863).

43 mg Compound 91 (0.05 mmol) and 15 mg Abacavir (0.05 mmol) are reacted in the presence of 12 mg DCC (0.06 mmol, 1.2 eq.). The mixture is dissolved in 1 ml of dry THF and stirred overnight at room temperature. The cloudy solution is filtered off and the solvent is removed in vacuo. The crude product is purified by chromatography. The collected fractions are concentrated to yield a white solid (20 mg, 40%). The expected Compound 90 is characterized by TLC ($R_f$=0.6 in chloroform/methanol/ammonia (90:9:1)) and by MS (M+2H, 566).

This protocol can be applied to other alcohols, some of which are listed in Table 3

TABLE 3

Representative class of alcohol compounds, which can be used in conjugation reactions.

Pencyclovir

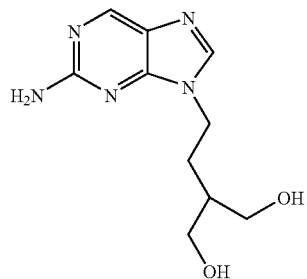

Lamivudine

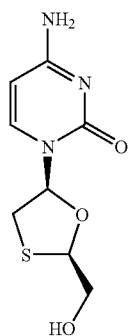

Carbovir

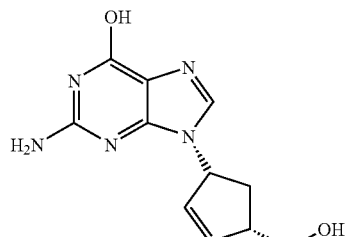

Abacavir

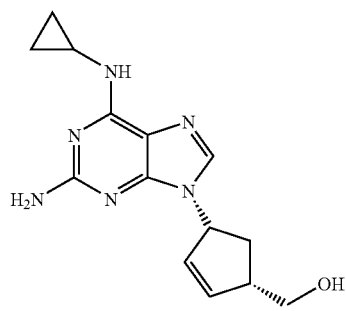

TABLE 3-continued

Representative class of alcohol compounds, which can be used in conjugation reactions.

Lodenosine

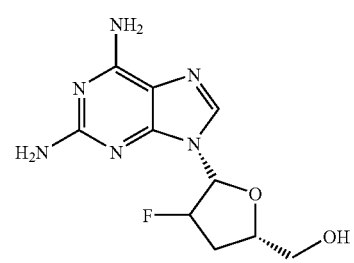

Mercaptopurine Riboside benzylidenacetal

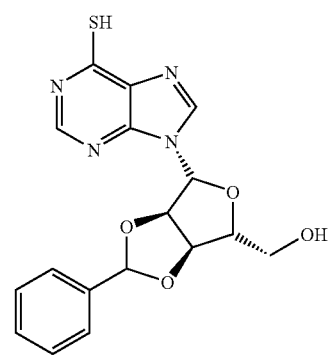

Zalcitabine

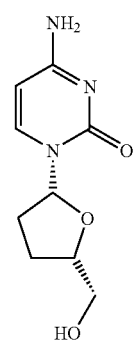

Gemcitabine

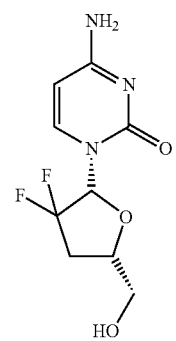

TABLE 3-continued

Representative class of alcohol compounds, which can be used in conjugation reactions.

Cytarabine

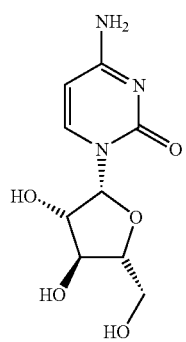

Levovirin
Benzylidene acetal

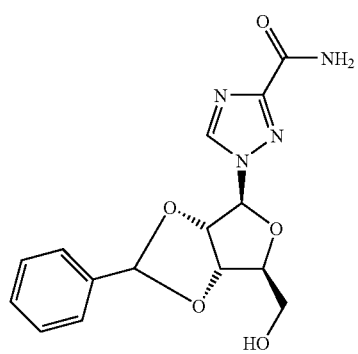

Ribavirin
Benzyliden acetal

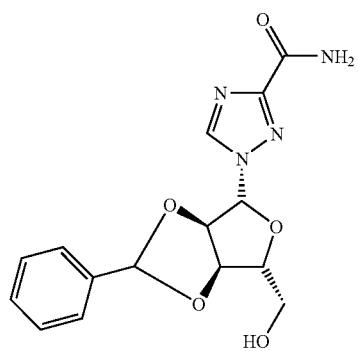

Compound 92

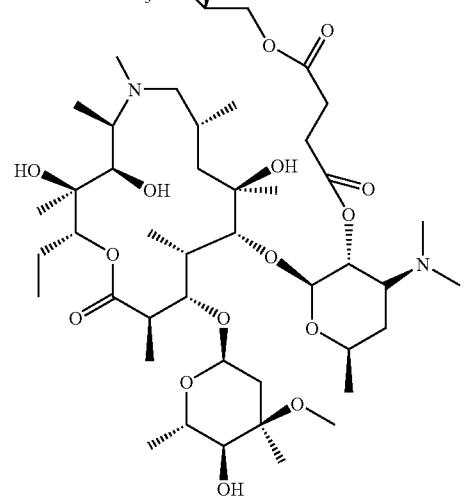

200 mg of Compound 43 (0.27 mmol) are treated with 30 mg succinic anhydride (0.3 mmol, 1.1 eq.) in 1 ml pyridine in the presence of a catalytic amount of DMAP. The reaction is stirred for 5 h at 40° C. After the completion of the reaction the product is separated by precipitation using hexane. The solution is decanted, and the recovered precipitate is washed several times with hexane to remove pyridine. The isolated compound is dried by high vacuum and yielded to a white solid (180 mg, 90%). The expected Compound 93 is characterized by MS ([M+H]+=850).

42 mg of Compound 93 (0.05 mmol) and 13 mg AZT (0.05 mmol) are coupled by using 11 mg DCC (0.055 mmol) in 0.5 ml of dry THF. The mixture is stirred overnight at room temperature. The cloudy solution is then filtered off to remove the urea.

The isolated crude product, obtained after removal of solvent, is purified by chromatography. The collected fractions yield after evaporation to a white solid (30 mg, 50%). The expected compound Compound 92 is characterized by TLC ($R_f$=0.3 in chloroform/methanol/ammonia (90:9:1)) and by MS (M+2H, 549.7).

This protocol can be applied to other alcohols, some of which are listed in Table 3.

Compoun 94

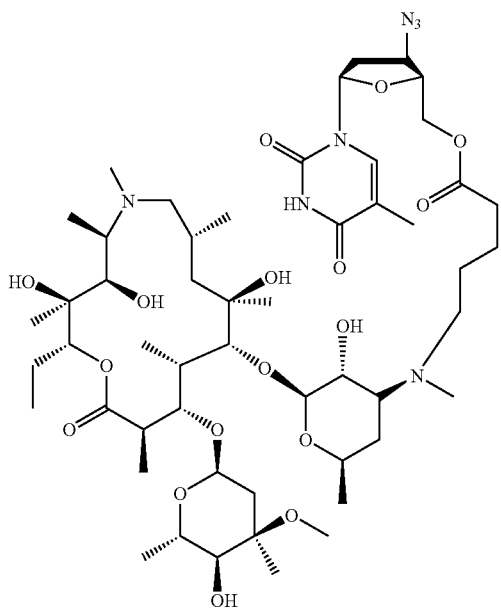

To a cloudy solution of 52 mg AZT (0.2 mmol), 43 mg 5-bromovaleric acid (0.24 mmol, 1.2 eq.), 106 mg BOP (0.24 mmol, 1.2 eq.), and a catalytic amount of DMAP in 1 ml dry THF are added 100 μl triethylamine (72 mg, 700 μmol, 3 eq.). The clear solution is then stirred for 4 h at room temperature. After completion of reaction the crude mixture is purified by preparative TLC. Removal from the plate yields a yellowish oily solid (60 mg, 70%). The expected compound 95 is characterized by TLC ($R_f$=0.7, chloroform/methanol/ammonia 90:9:1).

A solution of 6.0 g (8.0 mmol) of Compound 43 in 20 ml of THF is treated with 1.97 g (8.8 mmol) of N-iodosuccinic imide in several portions at 0° C. The mixture is kept at 10° C. for 12 h and then poured into a solution of potassium carbonate in water and extracted with dichloromethane. The organic phase is dried (Na2SO4), concentrated in vacuum and the residue chromatographed on silica gel, elution with cyclohexane/ethyl acetate/isopropanol/triethylamin 9:1:0.2:0.2 to yield 1.5 g (34%) of Compound 96, a colorless solid.

To a cloudy solution of 8 mg Compound 95 (0.02 mmol) and 26 mg Compound 96 (0.035 mmol, 2 eq.) in acetonitrile (0.5 ml) is added am excess of potassium carbonate. The reaction mixture is then set to 50° C. for 48 h. The crude mixture is purified by chromatography to yield a yellowish solid (4.5 mg, 20%). The expected Compound 94 is characterized by TLC ($R_f$=0.5 in chloroform/methanol/ammonia (90:9:1)) and by MS ([M+H]+=1113).

This protocol can be applied to other alcohols, some of which are listed in Table 3.

Compound 97

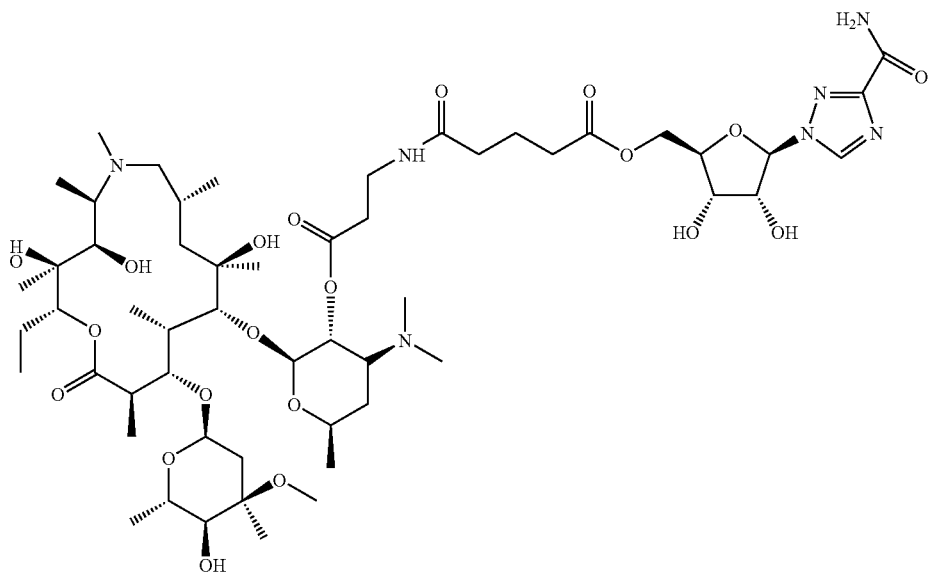

665 mg benzylidene-protected Ribavirin (2 mmol), 1.34 g glutaric acid (10 mmol, 5 eq.), 1 g CDI (6.2 mmol), and a catalytic amount of DMAP are suspended and heated in 20 ml of Chloroform for 3 h. The solvent is removed and the residue suspended in 1 M HCl, saturated with sodium chloride. The mixture is extracted twice with ethyl acetate, the organic layers are dried over sodium sulphate and evaporated to dryness. The residue is purified by chromatography to yield 760 mg (85%) of Compound 98, characterized by TLC (Rf=0.16 in THF/Hexane/Acetic acid 7:7:0.5) and MS ([M+H]+=447).

To a solution of 267 mg Z-β-alanine (1.2 mmol, 1.2 eq.) and 190 mg CDI (1.2 mmol, 1.2 eq.) in 2 ml of dry THF, which had been stirred for 30 minutes at room temperature under argon, 749 mg Compound 43 are added (1 mmol). The mixture is then stirred overnight at 40° C. The clear and colorless solution is purified by flash chromatography. The collected fractions are concentrated to yield to a yellow solid (460 mg, 50%). The expected compound is characterized by TLC ($R_f$=0.2 in chloroform/methanol/ammonia (90:9:1)) and by MS ([M+H]+=954.7). 450 mg of this compound (0.45 mmol) are dissolved in 5 ml of ethanol, to which an excess of Pd/C is added under argon. The flask with hydrogen. The mixture is shaken gently overnight at room temperature. The Pd/C is removed passing the solution through a celite plug. The removal of solvent yielded a slighty black solid (280 mg, 76%), a mixture of Compound 99 and Compound 43. The expected Compound 99 is characterized by TLC ($R_f$=0.2 in chloroform/methanol/ammonia (94.5:5:0.5)) and by MS ([M+H]+=890.5).

To a cloudy solution of 23 mg Compound 98 (0.05 mmol), and 41 mg free Compound 99. (0.05 mmol), 25 mg BOP (0,055 mmol, 1.1 eq.) and a catalytic amount of DMAP in 0.5 ml of dry THF are added 15 μl of triethylamine (11 mg, 0.11 mmol, 2 eq.). The clear solution is stirred overnight at room temperature. The mixture is purified by chromatography and yields 5 mg (10%) of a light yellowish solid. The expected Compound 100 is characterized by TLC ($R_f$=0.25 in chloroform/methanol/ammonia (90:9:1)) and by MS ([M+H]+= 1249).

5 mg of Compound 100 are dissolved in 5 ml 2-propanol and a tip of a spatula of Pd/C is added. The mixture is hydrogenated overnight. The catalyst is extracted with ethyl acetate and the extract purified by preparative TLC to yield 2.3 mg of the desired Compound 97, characterized by TLC ($R_f$=0.45, chloroform/2-propanol/methanol/ammonia 25:3:1:1) and MS ([M+H]+=1161).

Compound 101

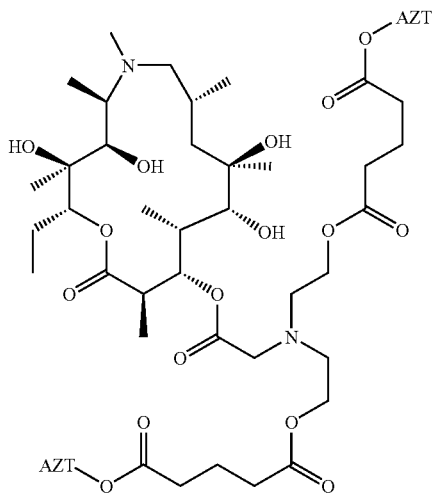

900 mg of Compound 43 (1.2 mmol) are treated with 10 ml 12 N HCl in an iced-water bath overnight. The completed reaction is worked up by an extraction with chloroform. The aqueous phase is further neutralized at 0° C. by addition of potassium hydroxide pellets to have a pH at 9-10. The orange basic aqueous phase is then extracted several times with chloroform. The combined organic layer is washed with brine and then dried over sodium sulphate. The crude product after evaporation of the solvent is purified by flash column chromatography to yield to a light yellowish solid (400 mg, 90%). The expected Compound 102 is characterized by TLC ($R_f$=0.35 in chloroform/methanol/ammonia (90:9:1)) and by MS ([M+H]+=434).

300 mg of the Compound 102 (0.7 mmol), 190 mg iodoacetic acid (1 mmol, 1.5 eq.) and 210 mg DCC (1 mmol, 1.5 eq.) are dissolved in 5 ml of dry chloroform at 0° C. under argon atmosphere under protection from light. The mixture is stirred overnight at room temperature. The yellowish cloudy solution is filtered off and the filtrate is concentrated under vacuum. Chromatography yields a fraction that contains mainly the monoacetylated product, Compound 103, (yield: 175 mg, 50%) is characterized by TLC ($R_f$=0.35 in chloroform/methanol/ammonia (90:9:1)) and by MS ([M+H]+= 602).

To a solution of 150 mg of Compound 103 (0.25 mmol) in 2 ml of dry acetonitrile are added 50 μl of diethanolamine (0.5 mmol, 2 eq.). The mixture is stirred at room temperature for 1 h. After removal of the solvent the crude mixture is purified by flash chromatography. The collected fractions are concentrated under vacuum and yield a yellowish solid (60 mg, 40%). The expected compound 104 is characterized by TLC ($R_f$=0.15 in chloroform/methanol/ammonia (90:9:1)) and MS ([M+H]+=579).

To a mixture of 800 mg glutaric acid (6 mmol, 6 eq.) and 500 mg CDI (3 mmol, 3 eq.) dissolved in 10 ml of dry acetonitrile, which is stirred for 30 minutes at room temperature under argon, are added 266 mg AZT (1 mmol) and a catalytic amount of DMAP. The cloudy reaction mixture is stirred overnight at 70° C. Chromatography yields a colorless sticky solid (120 mg, 35%). The expected compound 105 was characterized by TLC ($R_f$=0.25 in chloroform/methanol/ammonia (90:9:1)) and MS ([M+H]+=381).

To a cloudy solution of 55 mg of Compound 105 (0.15 mmol, 3 eq.), and 29 mg of Compound 104 (0.05 mmol, 1 eq.), 38 mg BOP (0.18 mmol, 3.3 eq.) and a catalytic amount of DMAP in 0.5 ml of dry THF are added 30 μl of triethylamine (0.25 mmol, 4 eq.). The clear solution is then stirred overnight at room temperature. The mixture is purified by chromatography. The collected fractions yielded to a light yellowish solid (5 mg, 10%). The expected double acylated Compound 101 is characterized by TLC ($R_f$=0.25 in chloroform/methanol/ammonia (90:9:1)) and by MS ([M+H]+ =1306).

This protocol can be applied to other alcohols, some of which are listed in Table 3. Abbreviations:

DMAP=4-(N,N-dimethylamino)pyridine

BOP=(Benzotriazol-1-yloxy)-tris-(dimethylamino)-phosphonium-hexafluorophosphate

CDI=Carbonyldiimidazole

Z—=Benzyloxycarbonyl-

Example 29

Compound 106

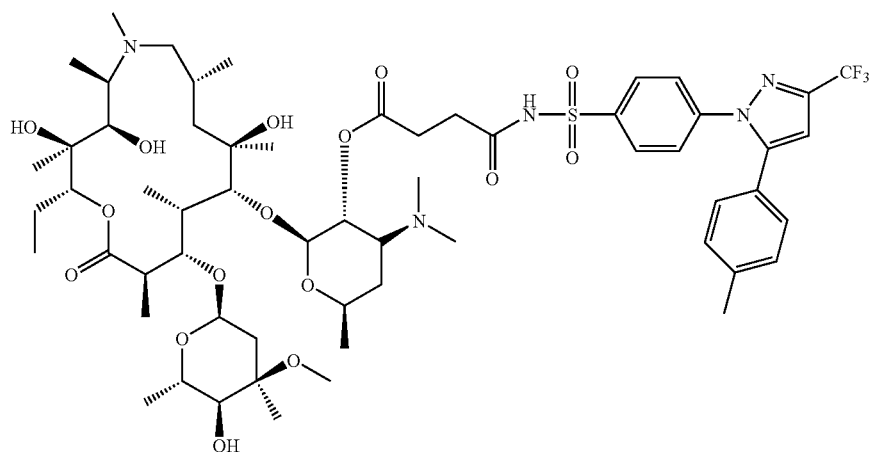

286 mg of Celecoxib (750 µmol), 300 mg of succinic anhydride (3 mmol, 4 eq.), and 50 mg of DMAP are dissolved in 8 ml of dry acetonitrile. 420 µl (300 µg, 3 mmol, 3 eq.) of triethylamine are added, and the reaction mixture is stirred overnight. 3 ml 1M aqueous sodium hydroxide and 5 ml of THF are added to remove excess succinic anhydride, the mixture is stirred for 2 h. 180 µl of acetic acid (3.1 mmol) are added and the mixture is evaporated to dryness. The resulting oil is suspended in ethyl acetate. Diluted aqueous ammonia is added, and the aqueous phase is separated and evaporated until the gas evolution ceases. Concentrated HCl is added to obtain a yellow precipitate. The residue is dissolved in ethanol, evaporated to dryness and dried at 30° C./0.01 mbar for 2 h. The yield of the resulting Compound 107 is 350 mg (93%), and can be used for the following step without further purification.

240 mg of Compound 107 (500 µmol) are stirred together with 110 mg of CDI (650 µmol, 1.3 eq.) in 8 ml of dry dichloromethane for 2 h. 300 mg (400 µmol, 0.8 eq.) of Compound 43 are added and the mixture is stirred for another 2 h. The mixture is subjected to chromatography after evaporation to yield 80 mg (16%) of the desired product, Compound 106 (MS: [M+H]+=1213).

Example 30

Compound 108

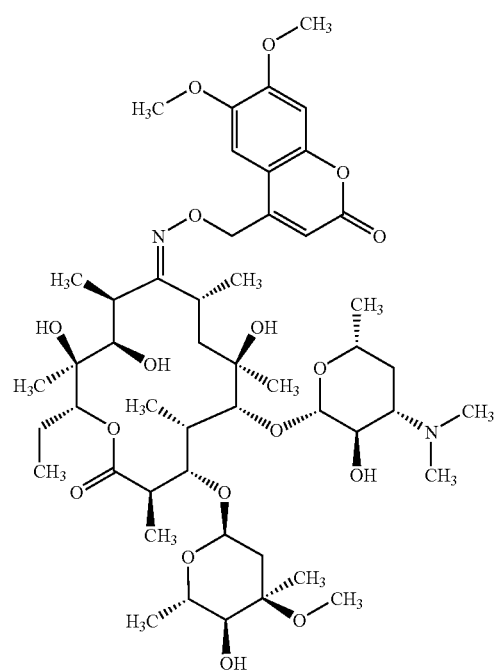

To a stirred solution of 1.12 g erythromycin A oxime (1.5 mmol) in 50 ml THF was added 1.5 ml 1 N potassium hydroxide solution (1.5 mmol) and 0.44 g 4-bromomethyl-6,7-dimethoxycoumarin (1.5 mmol). The reaction mixture was stirred at room temperature for 6 h and then filtered and treated with 44 µl of acetic acid. The solvent was removed under reduced pressure and the residue purified on silica gel, eluting with $CHCl_3/MeOH/NH_4OH$ (6:1:0.1) to afford 0.4 g (28%) of Compound 108 a colorless foam. (MS: [M+H]+= 968).

Compound 109

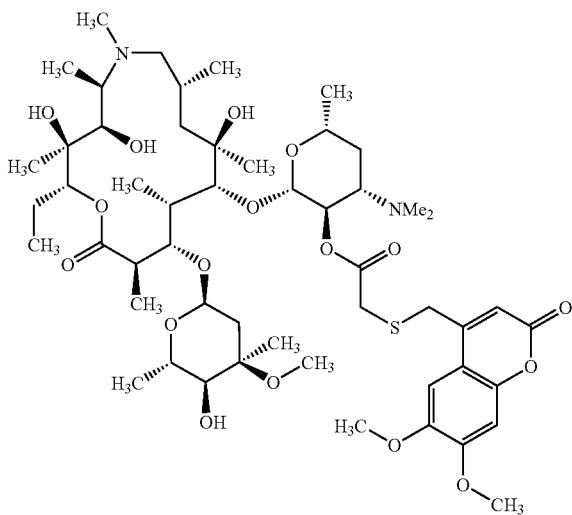

To a stirred suspension of 0.46 g (6,7-dimethoxy-2-oxo-2H-chromen-4-yl methylsulfanyl)acetic acid (1.5 mmol) in 20 ml of dry $CH_2Cl_2$ are added 250 mg N,N'-carbonyldiimidazole (1.55 mmol). The reaction mixture is stirred for 2 h, then a solution of 1.0 g Compound 43 (1.3 mmol) in 10 ml of dry $CH_2Cl_2$ is added and stirring continued for 48 h. A saturated aqueous solution of sodium bicarbonate (30 ml) is added. The organic layer is dried over $Na_2SO_4$, filtered and then concentrated under reduced pressure to furnish the crude product. Chromatography affords the Compound 109 as a white foam (0.7 g, 52%). (MS: [M+H]+=1042).

Example 31

Compound 110

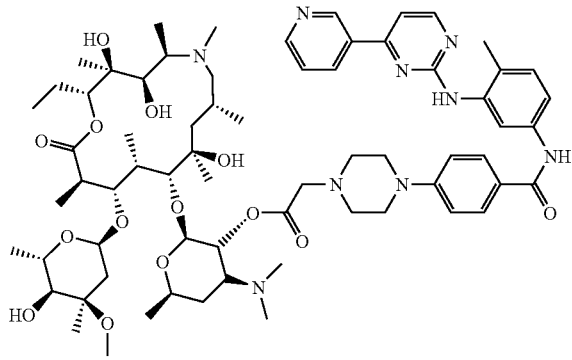

Imatinab may be selectively altered without compromising the interaction with the kinase and thus its biological activity (Schindler et al., Effects of a selective inhibitor of the Abl tyrosine kinase on the growth of Bcr-Abl positive cells. Science 289, 1938-1942, 2000).

2.2 g of 4-(4-Chlorocarbonyl-phenyl)-piperazine-1-carboxylic acid 9H-fluoren-9-ylmethyl ester and 1.15 g 4-Methyl-N3-(4-pyridin-3-yl-pyrimidin-2-yl)-benzene-1,3-diamine (U.S. Pat. No. 5,521,184) are reacted in 50 ml of dimethylformamide in the presence of 600 mg dimethylaniline for 24 h. The mixture is poured into 250 ml of ice-cold water. After filtration, the crude product is dried in vacuo and treated with a mixture of methanol and triethylamine (10:1). After evaporation of the solvent, the residue is subjected to chromatography to yield Compound 111.

40 mg of Compound 111 are dissolved in 2 ml dry ethanol at 60° C. and reacted with 31 mg of Compound 111 for 10 h. The mixture is cooled to −21° C. and filtered. The product, Compound 110, was obtained after recrystallisation. (MS: $[M+2H]^{2+}$=628).

Biological Methods

Example 32

Proliferation Assay

Assay to determine the in vitro rate of, for example, lymphocyte proliferation. Lymphocytes are purified out of ant coagulated (CPDA, citrate or heparin) mammalian blood using the Lymphoprep™ system (supplier). Purified cells are counted using a hemocytometer following Trypan Blue staining, and a cell concentration of $1 \times 10^6$ cells/ml established in RPMi 1640 medium with 10% FCS and antibiotics as required (all from Biochrome). Following the addition of a cell proliferation stimulant, for example phytohemagglutanin (Sigma) at, for example an end concentration of 5 µg/ml, the cells are incubated with different concentrations of the to be investigated compound in 100 µl end volume in a 96-well microtiter plate in an incubator (37° C., 5% $CO_2$, 95% humidity) for 72 h. Cell proliferation is quantified following BrdU incorporation for 16 h by ELISA and subsequent colorimetric development (Cell Proliferation ELISA BrdU (calorimetric) kit from Roche Diagnostics). The $IC_{50}$ (µM) values are then calculated, and used to compare compound efficacy.

To determine the influence of the T—L—C modification on in vitro cellular drug uptake and pharmacology, the above assay is additionally modified and an additional "wash" step included. In addition to running the assay for 72 h with the compounds to be tested, the assay is also run for just 2 h, then compound is washed away in three serial washing steps using 200 µl of medium at each step, and the cells subsequently incubated for a further 70 h. The determined $IC_{50}$ (µM) values following 2 h and 72 h incubation are compared and a ratio calculated (2 h:72 h). The lower the number, the better the uptake and drug release from the T—L—C in the cells (see results in Table 4 for examples), and improvement over mycophenolic acid.

TABLE 4

Proliferation assay results of T-L-C conjugates of mycophenolic acid

| Conjugate | IC$_{50}$ (μM) at 2 h | IC$_{50}$ (μM) at 72 h | Ratio (2 h:72 h) |
|---|---|---|---|
| Mycophenolic acid | 2.5 | 0.54 | 4.63 |
| Mycophenolate mofetil | 1.5 | 0.33 | 4.5 |
| Compound 67 | 1.74 | 1.36 | 1.3 |
| Compound 79 | 3.16 | 1.2 | 2.63 |
| Compound 74 | 3.2 | 2.2 | 1.45 |
| Compound 80 | 1.41 | 0.4 | 3.53 |
| Compound 81 | 1.78 | 1.12 | 1.6 |
| Compound 69 | 2.66 | 1.4 | 1.9 |

Example 33

Cell-Based IMDPH Assay with Guanosine Rescue

Cytotoxicity Assay

HeLa cells (DSMZ, ACC 57) and Jurkat cells (DSMZ, ACC 282) in exponential growth phase are exposed for 3 days to test compounds. The number of surviving cells is then determined by the Alamar Blue assay (Serotec Inc.). This assay incorporates a fluorometric growth indicator based on detection of metabolic activity. Specifically, the system incorporates an oxidation-reduction indicator that fluoresces in response to chemical reduction of the growth medium resulting from cell growth. As cells grow in culture, innate metabolic activity results in a chemical reduction of the immediate surrounding environment. Continued growth maintains a reduced environment while inhibition of growth maintains an oxidized environment. Reduction from growth causes the Redox indicator to change from an oxidized to a reduced form. Fluorescence is monitored at 560 nm (Exc.) and 590 nm Em.

General Procedure:

HeLa cells (1×10$^3$) or JURKAT cells (1×10$^3$) are plated in 100 μl MEM medium (with Earle's salt; Biochrom KG) containing 10% FBS, 2 mM L-glutamine, and non-essential animo acids in 96-well plates and incubated at 37° C. and 5% CO$_2$ atmosphere. After 24 hours, the test compounds are added over a concentration range and the cells incubated for a further 48 hours. Alamar Blue reagent (20 μl) is added to each well, and the cultures incubated for a further 4 to 6 hours. The fluorescence is then measured as described above and the LD$_{50}$ is determined based on a sigmoidal dose response regression. In order to determine the toxicity of T—L—C conjugates of mycophenolic acid not due to the inhibition of IMPDH, excess guanosine is added into the culture medium to a final concentration of 50 μM. Any toxicity still detected can then be ascribed either to other biological effects of the of T—L—C conjugate of mycophenolic acid, or is due to the very high intracellular concentration of mycophenolic acid, following concentrative uptake into the cell.

Cytotoxicity Assay with Fresh PBMNCs

The cytotoxicity of T—L—C conjugates of mycophenolic acid can be demonstrated directly on freshly isolated mammalian PBMNCs. The cells are prepared as described in Example 29, and the level of cytotoxicity determined by the Alamar Blue assay, as described above. As described for both HeLa and JURKAT cells, guanosine can also be used here to ameliorate the effect of mycophenolic acid on the activity of IMPDH.

Results:

The toxicity of mycophenolic acid conjugates may be assessed most conveniently in a cell based system, preferably with a rapidly growing cell line such as HeLa or JURKAT. In normal culture conditions, mycophenolic acid has an IC$_{50}$ of less than 2 uM, and its effect can be completely removed in the presence of 50 μM guanosine. For many of the T—L—C conjugates of mycophenolic acid, alleviation with guanosine is possible, but this is not always complete, which could for example be due to either to other biological effects of the of T—L—C conjugate of mycophenolic acid, or is due to the very high intracellular concentration of mycophenolic acid, following concentrative uptake into the cell.

Example 35

Efficacy Testing of Immunosuppressive Drugs Using a Mouse Skin Transplant Model

Skin transplant rejection is a strong immune response and serves as a very sensitive test of the immunosuppressive potential of drugs in organ transplantation and graft rejection. The mouse trunk skin transplant model was established using published methods (Billingham etal., 1954). Donor (B1 10) trunk skin (approximately 8×8 mm) is removed and kept cold in saline before grafting on recipient Balb C mice. Male mice (n=10) are dosed orally once a day from the day of transplant surgery (day 0) until the day of rejection. For each study, appropriate vehicle-treated control groups are run concurrently. Graft rejection is quantified as the number of days to reach R4 rejection (>75% of graft scabbed).

Figure 9:
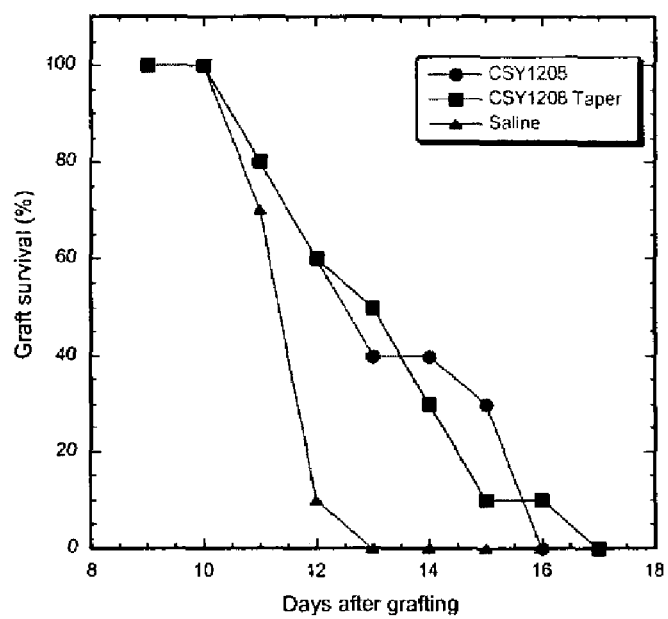
FIG. 9 shows survival of skin transplant following treatment with an example T—L—C conjugate.
Figure 10:
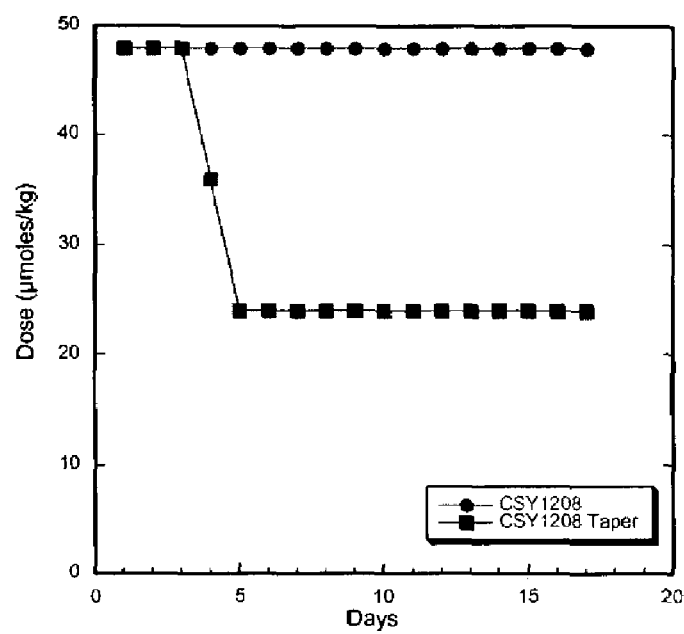
FIG. 10 shows dose tapering used in skin transplant model to study a T—L—C conjugate.

Results:

An example of results obtained with T—L—C conjugates of mycophenolic acid in the mouse skin transplant model are shown in FIG. 9. The mean rejection time for the vehicle, in this experiment saline, was 11.8 days, while the rejection time of the T—L—C conjugate Compound 67 was 13.5 days. Treatment with Compound 67 using dosage tapering (FIG. 10), resulted in a mean rejection time of 13.4 days.

Example 36

Testing of Antibiotic Activity of Drugs

Assay Summary

The TC$_{50}$ or MIC procedure for antibiotic sensitivity testing involves an antibiotic dilution assay, which can be performed in microtitre plates. A series of twofold dilutions of each antibiotic are made in the wells, and then all wells are inoculated with a standard amount of the same test organism. After incubation, growth in the presence of the various antibiotics is observed by measuring turbidity. Antibiotic sensitivity is expressed as the concentration of the antibiotic that inhibits 50% of the growth (TC$_{50}$). Alternatively it could be expressed as the highest dilution of antibiotic that completly inhibits growth (MIC).

Bacteria: *B. pumilus* and *E. coli* (DH5α)

Bacterial cultures are initiated from the plates for 2 to 3 weeks. After this time period bacteria are streaked out on new plates from the backups stored at −80° C. Due to the lack of resistance of the bacteria, new cultures are not to be initiated from an old plate or any liquid cultures derived from old plates.

Growth medium (GM)(per liter): 10 g Bacto-tryptone, 5 g Bacto-yeast extract, 6 g HEPES (25 mM), 5.4 g NaCl, pH 7.3

Compound stocks 10 or 100 mM in DMSO stored at −20° C.

Procedure

1. Grow B.pumilus from an LB agar plate in a flask (max. 10% volume) up to about 50 ml in growth medium (GM)
2. Dilute overnight suspension 1:10 in GM
3. Determine $OD_{600}$ of diluted bacterial suspension
4. Dilute bacterial suspension in GM to an $OD_{600}$ of 0.03-0.04. (6 ml/plate)
5. Add 200 μl GM to the outer wells (Row A, Row H, Column 1, Column 12)
6. Add 100 μl GM to each well starting from C2, row 3.
7. Controls: Wells B2-B4 growth control. Wells B6-B8 blank. Row C growth inhibition control.
   7.1. To wells B2-B4 add: 96 μl GM, 4 μl DMSO, and 100 μl bacterial suspension adjusted to an $OD_{600}$ of 0.03-0.04.
   7.2. To wells B6-B8 add: 196 μl GM and 4 μl DMSO
   7.3. Dilute a 10 mM COMPOUND 43 (positive control) stock to 800 μM (120 μl/plate) in GM. Add 100 μl of 800 μM COMPOUND 43 solution to well C2.
8. Samples
   8.1. Dilute the 10 or 100 mM stock solutions to 800 μM (250 μl/plate) in GM.
   8.2. Add 100 μl of 800 μM sample in duplicates to wells D2/E2 resp. F2/G2.
   8.3. 2-fold serial dilution of all samples and Azithromycin
      8.3.1. Rows C-G, Columns 2: Mix and transfer 100 μl from each row to Column 3, and continue until column 11. The remaining 100 μl out of column 11 are disposed.
9. Add 100 μl of bacterial suspension ($OD_{600}$ 0.03-0.04) to each well from C2-G11.
10. Incubate plates on shaker, 750 rpm, 37° C., until the growth controls have reached an $OD_{600}$ of 0.6-0.8 (approximately 6-8 h).
11. Determine $OD_{600}$ on plate reader.

TABLE 5

$TC_{50}$ values for representative compounds.

| Compound | $TC_{50}$ in E. coli (μM) |
|---|---|
| COMPOUND 43 | 2.3 |
| COMPOUND 40 | >50 |
| COMPOUND 96 | 28 |
| COMPOUND 53 | >50 |
| COMPOUND 45 | >50 |

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

CITATIONS

Alberola A., Antolin L. F., Gonzalez A. M., Laguna M. A., and Pulido F. J.; J. Heterocyclic Chem; 23; 1035; (1986).

Alberola A., Antolin L. F., Gonzalez A. M., Pulido F. J.; Base-induced Ring Cleavage of 4-Functionalized 3-Unsubstituted Isoxazoles. Synthesis of 2-Aminopyrimidines and Pyrimidine-2(3H)-thiones; Heterocycles; (1987).

Antoniou E A, Xu M, Howie A, Chondros K, McMaster P, D'Silva M, 1997 Combination treatment effectively intercepts advanced acute cardiac rejection, Transplant Proc Nov; 29(7):2888-91.

Arion D, Meijer L, Brizuela L, Beach D, 1988, Cell 55, 371-378.

Axton et al., 1992, J. Chem. Soc. Perkin Trans. I 2203 ff.

Bartlett et al., 1991, Agents and Actions, 32 10-21.

Beeson J M 1999, The neurobiology of pain, Lancet;353: 1610-1615.

Bennett J E, 1977, Flucytosine. Ann. Intern. Med. 86,319-322.

Benslay D N and Bendele A M, 1991, Agents Actions 34: 254.

Billingham et al., 1954. Proc. R. Soc. 143: 43-55.

Brater D C, 1999, Effects of nonsteroidal anti-inflammatory therapeutic agents on renal function: focus on cyclooxygenase-2-selective inhibition, Am J Med Dec 13;107(6A): 65S-70S; discussion 70S-71S.

Breedveld F C, Dayer J M, 2000, Leflunomide: mode of action in the treatment of rheumatoid arthritis, Ann Rheum Dis Nov;59(11):841-9.

Buchdunger E, Mett H, Trinks U, Regenass U, Muller M, Meyer T, Beilstein P, Wirz B, Schneider P, Traxler P, 1994, 4,5-Dianilinophthalimide: A protein-tyrosine kinase inhibitor with selectivity to the epidermal growth factor receptor signal transduction pathway and potent in vivo antitumor activity. Proc. Nat. Acad. Sci. USA 91, 2334-2338.

Buchdunger E, Zimmermann J, Mett H, Meyer T, Muller M, Regenass U, Lydon N B, 1995, Selective inhibition of the platelet-derived growth factor signal transduction pathway by a protein-tyrosine kinase inhibitor of the 2-phenylaminopyrimidine class. Proc. Nat. Acad. Sci. USA 92, 2558-2562.

Carlson R P, Datko Li, O Neil-Davis L, Blazek E M, Delustro F, Beideman R, and Lewis A J, 1985, Comparison of inflammatory changes in established type II collagen and adjuvant induced arthritis using outbred Wistar rats, J. Immunopharmacol. 7: 811-826.

Churchill L, Graham A G, Shih C-K, Pauletti D, Farina P R, Grob P M, 1996, Selective inhibition of human cyclo-oxygenase-2 by meloxicam. Inflammopharmacology; 4: 125-135.

Colville-Nash P R and Gilroy D W, 2001, Potential adverse effects of cyclooxygenase-2 inhibition: evidence from animal models of inflammation BioTherapeutic agents;15(1):1-9.

Conner E M, Grisham M B, 1996, Inflammation, free radicals and antioxidants, Nutrition 12(4), 274-277.

Cronstein B N, 1995, The antirheumatic agents sulphasalazine and methotrexate share an anti-inflammatory mechanism, Br J Rheumatol Nov;34 Suppl 2:30-2.

Curkovic B et al., 2000 Nonsteroidal antirheumatic agents—present status and perspectives, Reumatizam;47(2): 7-10.

Daley, G Q. & Baltimore, O, 1988 Transformation of an interleukin 3-dependent hematopoietic cell line by the chronic myelogenous leukemia-specific p21Obcr-abl protein. Proc. Nat. Acad. Sci. USA 85, 9312-9316.

De Clercq, E, 1993: Antiviral agents: characteristic activity spectrum depending on the molecular target with which they interact. Academic Press, Inc., New York, N.Y. 1-55

Debruyne D and Ryckelynck J P, 1993, Clinical pharmacokinetics of fluconazole. Clin. Pharmacokinet. 24,10-27.

Debs R J, Fuchs H J, Philip R, Brunette E N, Duzgunes N, Shellito J E, Liggitt D, Patton J R, 1990, Immunomodulatory and toxic effects of free and liposome-encapsulated tumor necrosis factor alpha in rats. Cancer Res. January 15; 50(2): 375-80.

Escola J M, Deleuil F, Stang E, Boretto J, Chavrier P, Gorvel J P. Characterization of a lysozyme-major histocompatibility complex class II molecule-loading compartment as a specialized recycling endosome in murine B lymphocytes. J Biol Chem. Nov. 1, 1996;271(44):27360-5.

Ford C W, Hamel J C, Wilson D M, Moerman J K, Stapert D, Yancey R, Hutchinson D K, Barbachyn M R, Brickner S J, 1996, In vivo Activities of U-100592 and U-100766, Novel Oxazlidinone Antimicrobial Agents, against Experimental Bacterial Infections. Animicrobial Agents and Chemotherapy 1508-1513.

Fox R I J, 1998, Mechanism of action of leflunomide in rheumatoid arthritis, Rheumatol Suppl Jul; 53:20-6.

Fung H B, Kirschenbaum H L, 1999, 57Selective cyclooxygenase-2 inhibitors for the treatment of arthritis, Clin Ther Jul;21(7): 1131-1135.

Furst D E, 1999, Leflunomide, mycophenolic acid and matrix metalloproteinase inhibitors, Rheumatology (Oxford) Nov; 38 Suppl 2:14-8.

Gilbert, B. E. and Knight V., 1986: Biochemistry and clinical applications of ribavirin. Antimicrob. Agents and Chemother. 30:201-205

Gull K and Trinci A P J, 1973, Griseofulvin inhibits fungal mitosis. Nature. 244, 292-294.

Harada M, Sakakibara H, Yano T, Suzuki T, Okuno S, 2000, Determinants for the therapeutic agent release from T-0128, camptothecin analogue-carboxymethyl dextran conjugate. J Control Release. December 3;69(3):399-412.

Hata K, Kimura J, Miki H, Toyosawa T, Moriyama M and Katsu K, 1996, Efficacy of ER-30346, a novel oral triazole antifungal agent, in experimental models of Aspergillosis, Candidiasis and Cryptococcosis. Antimicrobial Agents and Chemotherapy, 40,2243-2247.

Hawkey C J, 1999, COX-2 inhibitors. Lancet; 353:307-314.

Hepatology 7: 724-731

Hial V, De Mello M C, Horakova Z, Beaven M A, 1977, Antiproliferative activity of anti-inflammatory therapeutic agents in two mammalian cell culture lines J Pharmacol Exp Ther. Aug;202(2):446-54.

Honda S, Migita K, Hirai Y, Origuchi T, Yamasaki S, Kamachi M, Shibatomi K, Fukuda T, Kita M, Hida A, Ida H, Aoyagi T, Kawakami A, Kawabe Y, Oizumi K, Eguchi K, 2001, Expression of membrane-type 1 matrix metalloproteinase in rheumatoid synovial cells, Clin Exp Immunol 2001 October;126(1):131-6.

Hultgren, C., Millich, D. R., Weiland, O., Sälberg, M., 1998: The antiviral compound ribavirin modulates the T-helper (Th)1/Th2 subset balance in hepatitis B and C virus-specific immune response. J. Gen. Virol. 79: 2381-2391

Hutchins R O, Hoke D, Keogh J, Koharstki D, 1969, Sodium Borohydride in Dimethyl Sulfoxide or Sulfolane. Convenient Systems for Selective Redutions of Primary, Secondary, and Certain Tertiary Halides and Tosylates. Tetrahedron Letters, 3495-3498.

Iñiguez M A, Punzòn C, Fresno M, 1999, Induction of Cyclooxygenase-2 on Activated T Lymphocytes: Regulation of T Cell Activation by Cyclooxygenase-2 Inhibitors, The Journal of Immunology, 163: 111-119.

Jaafari M R, Foldvari M, 2002, Targeting of Liposomes to Human Keratinocytes Through Adhesive Peptides from Immunoglobulin Domains in the Presence of IFN Therapeutic agent Deliv. 9(1):1-9.

Kalgutkar A S, Crews B C, Rowlinson S W, Marnett A B, Kozak K R, Remmel R P, Marnett L J, 2000, Biochemically based design of cyclooxygenase-2 (COX-2) inhibitors: facile conversion of nonsteroidal antiinflammatory therapeutic agents to potent and highly selective COX-2 inhibitors, Proc Natl Acad Sci USA Jan 18;97(2):925-30.

Kanakura Y, Druker B, Cannistra S A, Furukawa Y, Torimoto Y, Griffin J D, 1990, Signal transduction of the human granulocyte-macrophage colony-stimulating factor and interleukin-3 receptors involves a common set of cytoplasmic proteins. Blood 76, 706-715.

Kharbanda S, Ren R, Pandey P, Shafman T D, Feller S M, Weichselbaum R R, Kufe D W, 1995, Activation of the c-abl tyrosine kinase in stress response to DNA-damaging agents. Nature 376, 785-788.

Klegeris A, McGeer P L, 1994, Rat brain microglia and peritoneal macrophages show similar responses to respiratory burst stimulants, Journal of Neuroimmunology 53(1), 83-90.

Klegeris A, Walker D G, McGeer P L, 1994, Activation of macrophages by Alzheimer b amyloid peptide, Biochemical and Biophysical Research Communications 199(2), 984-991.

Korba, B. E. and Boy, M. R., 1996: penciclovir is a selective inhibitor of hepatitis B replication in cultured human hepatoblastoma cells. Antimicrob. Agents and Chemother. 40:1282-1284

Kurtz M B, Heath I B, Marrinan J, Dreikorn S, Onishi J and Douglas C, 1994, Morphological effects of lipopeptides against *Aspergillus fumigatus* correlate with activities against (1,3)-b-D-glucan synthase. Antimicrob. Agents Chemother. 38,1480-1489.

Labro M T and Abdelghaffar H, 2001, Immunomodulation by macrolide antibiotics. J. Chemother. Feb; 13(1):3-8. Review.

Lipinski C A, Lombardo F, Dominy B W, Feeney P J., Experimental and computational approaches to estimate solubility and permeability in therapeutic agent discovery and development settings., Adv Therapeutic agent Deliv Rev. Mar. 1, 2001;46(1-3):3-26. Review.

Malmstrom K, Daniels S, Kotey P, Seidenberg B C, Desjardins P J, 1999, Comparison of rofecoxib and celecoxib, two cyclooxygenase-2 inhibitors, in postoperative dental pain: a randomized, placebo- and active-comparator-controlled clinical trial, Clin Ther Oct;21(10): 1653-63.

Marion, P. L., Cullen, J. M., Azcarraga, R. R., Van Davelaar, M. J., Robinson, W. S., 1987: Experimental transmission of duck hepatitis B virus to pekin ducks and to domstic geese.

Marks D, Belov L, Davey M W, Davey R A, Kidman A, 1992, The MTT cell viability assay for cytotoxicity testing in multitherapeutic agent-resistant human leukemic cells, Leukemia Research 16, 1165.

Marriott M S and Richardson K, 1987, The discovery and mode of action of fluconazole, p. 81-92. In R. A. Fromtling (ed.), Recent trends in the discovery, development, and evaluation of antifungal agents. J. R. Prous Science Publishers, Barcelona.

Martin, M. J., Navas, S., Quiroga, J. A., Pardo, M., Carreno, V., 1998: Effects of the ribavirin-interferon alpha combination on cultured peripheral blood mononuclear cells from chronic hepatitis C patients. Cytokine Aug;10(8):635-44.

Martin, M. J., Navas, S., Quiroga, J. A., Pardo, M., Carreno, V., 1998: Effects of the ribavirin-interferon alpha combination on cultured peripheral blood mononuclear cells from chronic hepatitis C patients. Cytokine Aug;10(8):635-44.

Martin, Pipasha Biswas, Mann, 2000, The incidence of adverse events and risk factors for upper gastrointestinal disorders associated with meloxicam use amongst 19 087 patients in general practice in England: cohort study, British Journal of Clinical Pharmacology 50 Issue 1 35.

Matsuguchi T, Salgia R, Hallek M, Eder M, Druker B, Ernst T J, Griffin J D, SHC phosphorylation in myeloid cells is regulated by GM-CSF, IL-3, and steel factor and is constitutively increased by p2IOBCR-ABL. J. Biol. Chem. 269, 5016-5021.

Matulonis U, Salgia R, Okuda K, Druker B, Griffin J D, 1993, IL-3 and p21OBCR/ABL activate both unique and overlapping pathways of signal transduction in a factor-dependent myeloid cell line. Exp. Hematol. 21, 1460-1466.

McGeer E G, McGeer P L, 1997, Inflammatory cytokines in the CNS, CNS Therapeutic agents 7, 214-228.

McGeer P L, McGeer E G, 1995, The inflammatory system of brain: implications for therapy of Alzheimer and other neurodegenerative disorders, Brain Research Review 21(2), 195-218.

McGeer P L, Rogers J., 1992, Anti-inflammatory agents as a therapeutic approach to Alzheimer's disease, Neurology 42(2), 447-449.

McGeer P L, Schulzer M, McGeer E G, 1996, Arthritis and antiinflammatory agents as negative risk factors for Alzheimer disease: A review of seventeen epidemiological studies, Neurology 47(2), 425-432.

Mochitate K, Katagiri K, and Miura T, 2001, Impairment of microbial killing and superoxide-producing activities of alveolar macrophages by a low level of ozone, J. Health Science, 47,302-309.

Mortellaro A, Songia S, Gnocchi P, Ferrari M, Fornasiero C, D'Alessio R, Isetta A, Colotta F, Golay J, 1999, New immunosuppressive therapeutic agent PNU156804 blocks IL-2-dependent proliferation and NF-kB and AP-1 activation. The Journal of Immunology, 7102-7109.

Nielsen O H, Bukhave K, Elmgreen J, Ahnfelt-Ronne I., 1987, Inhibition of 5-lipoxygenase pathway of arachidonic acid metabolism in human neutrophils by sulfasalazine and 5-aminosalicylic acid, Dig Dis Sci Jun;32(6):577-82.

Pendergast A M, Muller A J, Havlik M H, Clark R, McCormick F, Witte O N, 1991, Evidence for regulation of the human ABL tyrosine kinase by a cellular inhibitor. Proc. Nat. Acad. Sci. USA 88, 5927-5931.

Penglis P S, James M J, Cleland L G, 200, 1Cyclooxygenase inhibitors: any reservations?, Intem Med J Jan-Feb;31 (1):37-41.

Quallich L G, Greenson J, Haftel H M, Fontana R J, 2001, Is it Crohn's disease? A severe systemic granulomatous reaction to sulfasalazine in patient with rheumatoid arthritis, BMC Gastroenterol;1(1):8.

Rainsford K D, 2001, The ever-emerging anti-inflammatories. Have there been any real advances? J Physiol Paris Jan-Dec;95(1-6):11-9.

Ramasamy, K. S., Tam, R. C., Bard J, Averett, D. R., 2000: Monocyclic L-nucleosides with type 1 cytokine-inducing activity. J Med Chem. Mar. 9, 2000;43(5):1019-28.

Rankin, J. T., Eppes, S. B., Antczak, J. B., Joklik, W. K, 1989: Studies on the mechanism of the antiviral activity of ribavirin against reovirus. Virology 168: 147-158

Roher A E, Chaney M O, Kuo Y M, et al., 1996, Morophology and toxicity of A-beta (1-42) derived from neuritic and vascular amyloid deposits of Alzheimer's disease, Journal of Biological Chemistry 271(34), 20631-20635.

Rossi L, Brandi G, Fraternale A, Schiavano G F, Chiarantini L, Magnani M., Inhibition of murine retrovirus-induced immunodeficiency disease by dideoxycytidine and dideoxycytidine 5'-triphosphate., J Acquir Immune Defic Syndr. 1993 November; 6(11):1179-86.

Schindler T, Bornmann W, Pellicena P, Miller W T, Clarkson B, Kuriyan J, 2000, Structural Mechanism for STI-571 Inhibition of Abelson Tyrosine Kinase, Science 289, 1938-1942.

Schluesener H J, Seid K, Deininger M, Schwab J, 2001, Transient in vivo activation of rat brain macrophages/microglial cells and astrocytes by immunostimulatory multiple CpG, oligonucleotides., J Neuroimmunol. February 1;113 (1):89-94.

Schrier D J, Moniot S, Gluckman M I, Gilbertsen R B, 1987, The topical anti-inflammatory effects of a topical preparation of meclofenamic acid on carrageenan-induced footpad swelling in mice. J Pharm Pharmacol Jan; 39(1):57-9

Schroit A J, Madsen J, Nayar R, 1986, Liposome-cell interactions: in vitro discrimination of uptake mechanism and in vivo targeting strategies to mononuclear phagocytes., Chem Phys Lipids. Jun-Jul; 40(2-4):373-93.

Schwab J M, Brechtel K, Nguyen T D, Schluesener H J., Persistent accumulation of cyclooxygenase-1 (COX-1) expressing microglia/macrophages and upregulation by endothelium following, spinal cord injury., J Neuroimmunol. Nov. 1, 2000;111 (1-2):122-30.

Schwab J M, Frei E, Klusman I, Schnell L, Schwab M E, Schluesener H J, 2001, AIF-1 expression defines a proliferating and alert microglial/macrophage phenotype following spinal cord injury in rats., J Neuroimmunol. October 1;119 (2):214-22.

Schwab J M, Seid K, Schluesener H J, 2001, Traumatic brain injury induces prolonged accumulation of cyclooxygenase-1 expressing microglia/brain macrophages in rats, J Neurotrauma. 2001 September;18(9):881-90.

Sheehan D J, Hitchcock C A and Sibley C M, 1999, Current and emerging azole antifungal agents. Clin. Microbiol. Rev. 12,40-79.

Shen Y, Li R, McGeer E G, McGeer P L, 1997, Neuronal expression of mRNAs for complement proteins of the classical pathway in Alzheimer brain, Brain Research 769(2), 391-395.

Smedegard G, Bjork J, 1995, Sulfasalazine: mechanism of action in rheumatoid arthritis, Br J Rheumatol Nov;34 Suppl 2:7-15.

Stepkowski S M, Erwin-Cohen R A, Behbod F, Wang M E, Qu X, Tejpal N, Nagy Z S, Kahan B D, Kirken R A, 2002, Selective inhibitor of Janus tyrosine kinase 3, PNU156804, prolongs allograft survival and acts synergistically with cyclosporine but additively with rapamycin. Blood, 99, 680-689.

Strohmeyer R, Rogers J, 2001, Molecular and cellular mediators of Alzheimer's disease inflammation, Journal of Alzheimer's Disease 3, 131-157.

Tam R. C., Pai, B., Bard, J., Lim, C., Averett, D. R., Phan, U. T., Milovanoviv, T., 1999: Ribavirin polarizes human T cell responses towards a Type 1 cytokine profile. J. Hepatol. 30: 376-382

Tam, R. C., Ramasamy, K., bard, J., Pai, B., Lim, C., Averett, D. R., 2000: The Ribavirin Analog ICN 17261 Demonstrates Reduced Toxicity and Antiviral Effects with Retention of both Immunomodulatory Activity and Reduction of Hepatitis-Induced Serum Albumin Alanine Aminotransferase Levels. Antimicrob. Agents and Chemother. 44:1276-1283

Taupenot L, Ciesielski-Traska J, et al., 1996, Chromogranin A triggers a phenotypic transformation and the generation of nitric oxide in brain microglial cells, Neuroscience 72(2), 377-389.

Terai K, McGeer E G, McGeer P L, 1997, Neurons express proteins of the classical complement pathway in Alzheimer disease, Brain Research 769(2), 385-390.

Terrell C L and Hughes C E, 1992, Antifungal agents used for deep-seated mycotic infections. Mayo Clin Proc. 67,69-91.

Vere Hodge R. A., Sutton, D., Boyd, M. R., Harnden, M. R., Jarvest, R. L., 1989: Selection of an oral protherapeutic agent (BRL 42810; famciclovir) for the antiherpesvirus agent BRL 39123[9-(4-hydroxy-3-hydroxymethylbut-1-yl)guanine; penciclovir]. Antimicrob Agents Chemother 33(10): 1765-73

Wahl B. C, Liptay S, Adler G, Schmid R M, 1998, Sulfasalazine: a potent and specific inhibitor of nuclear factor kappa, J Clin Invest March 1;101(5):1163-74.

Wallace J L, 1999, Distribution and expression of cyclooxygenase (COX) isoenzymes, their physiological roles, and the categorization of nonsteroidal anti-inflammatory therapeutic agents (NSAIDs), Am J Med December 13;107(6A):11S-16S; discussion 16S-17S.

Weinblatt M E, Dixon J A, Falchuk K R, 2001, Serious liver disease in a patient receiving methotrexate and leflunomide, Prescrire Int Oct; 10(55):149; Arthritis Rheum Nov;43(11): 2609-11.

Wilson C L, Ouellette A J, Satchell D P, Ayabe T, Lopez-Boado Y S, Stratman J L, Hultgren S J, Matrisian L M, Parks W C, 1999, Regulation of intestinal alpha-defensin activation by the metalloproteinase matrilysin in innate host defense. Science October 1;286(5437): 113-7.

Xu X, Shen J, Mall J W, Myers J A, Huang W, Blinder L, Saclarides T J, Williams J W, Chong A S, 1999, In vitro and in vivo antitumor activity of a novel immunomodulatory therapeutic agent, leflunomide: mechanisms of action, Biochem Pharmacol November 1;58(9):1405-13.

| Patents: | | | |
|---|---|---|---|
| U.S. Pat. No. 3,926,955 | September 1972 | Burton et al. | 260/239 |
| U.S. Pat. No. 5,521,184 | April 1994 | Zimmermann | 514/252 |
| U.S. Pat. No. 5,721,277 | April 1995 | Tang | 514/646 |
| U.S. Pat. No. 6,271,383 | July 1999 | Gravestock | 546/209 |
| U.S. Pat. No. 6,136,796 | October 2000 | Kozak | 514/75 |
| U.S. Pat. No. 2001/0053782A1 | December 2000 | Blumenkopf et al. | 514/258 |
| U.S. Pat. No. 6,316,425 | November 2001 | Myhren et al. | 514/49 |
| WO9820876 | November 1996 | McCullough and Koch | C07D 521/00 |
| WO9821213 | November 1996 | McCullough et al. | A61K 31/495 |
| WO98/29437 | December 1997 | Young | 14/00 |
| WO9832762 | January 1997 | Myhren et at. | C07H 19/073 |
| WO9945008 | March 1998 | Hayase et at. | C07D 417/06 |
| WO0034281 | December 1998 | Whittaker et al | C07D 475/08 |
| WO0142246A2 | October 1999 | Blumenkopf et al. | C07D 487/04 |
| WO09/963937 | July 1999 | Griffin | |
| WO0114397A1 | August 1999 | Or et al. | C07H 17/08 |
| WO01/20331 | September 2000 | Dower et al | 33/566 |
| WO01/13957 | August 2000 | Rothbard | 47/48 |
| EP0013376B1 | May 1982 | Kämmerer and Schleyerbach | C07D 261/18 |
| EP009944 | | Firestone | 31/13 |
| EP0627406A1 | October 1992 | Fujita et al. | C07C 215/10 |
| EP0632038B1 | January 1992 | Matsuoka et al. | C07C 475/08 |
| EP0676399A1 | December 1992 | Ohi and Suzuki | C07C 475/08 |
| JP05163293 | | | 514/252 |

What is claimed is:

1. A compound, wherein the compound is

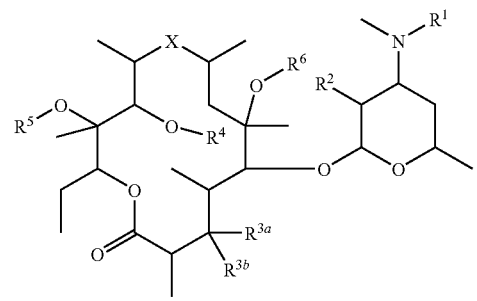

wherein:
X=N($R^7$)—$CH_2$,
$CH_2$—N($R^7$),
C(=O),
C(=N$OR^8$),
CH(O$R^9$),
CH(N$R^{10}R^{11}$),
C(=N$R^{12)}$,
OC(=O), or
C(=O)O,
Y=independently, linker,
Z=C(=O)-, or
CH($R^{16}$)-,
$R^1$=H,
$CH_3$,
($C_2$-$C_{10}$)alkyl,
($C_2$-$C_{10}$)alkenyl,
($C_2$-$C_{10}$)alkynyl,
($C_1$-$C_8$)[($C_1$-$C_4$)alkoxy]alkyl,
($C_2$-$C_8$)[($C_1$-$C_4$)alkoxy]alkenyl,
($C_6$-$C_{10}$)aryl-($C_1$-$C_5$)alkyl,
($C_2$-$C_9$)heteroaryl-($C_1$-$C_5$)alkyl,
($C_1$-$C_4$)alkyliden-N$R^{18}R^{19}$,
Y—$R^{13}$,
C(=O)—Y—$R^{15}$,
C(=O)—$R^{15}$,
S(=O)$_k$($C_1$-$C_{10}$)alkyl,
S(=O)$_k$($C_2$-$C_{10}$)alkenyl,
S(=O)$_k$($C_2$-$C_{10}$)alkynyl,
S(=O)$_k$(C6-$C_{10}$)aryl,
S(=O)$_k$($C_2$-$C_9$)heteroaryl,
S(=O)$_k$—Y—$R^{15}$, or
S(=O)$_k$—$R^{15}$, wherein k is 0, 1 or 2 and alkyl, alkenyl, alkynyl, cycloalkyl, heterocycloalkyl, aryl and heteroaryl can optionally be substituted by one to three halogen, cyano, hydroxy, $(C_1-C_4)$alkyloxy, nitro, $(C_1-C_6)$alkyl, $(C_2-C_6)$alkenyl, $(C_2-C_6)$alkynyl, $(C_3-C_7)$cycloalkyl, $(C_1-C_6)$heterocycloalkyl, $(C_6-C_{10})$aryl, $(C_1-C_9)$heteroaryl, $NR^{18}R^{19}$, $R^{18}C(=O)—$, $R^{18}C(=O)O—$, $R^{18}OC(=O)—$, $R^{18}C(=O)NH—$, $R^{16}NHC(=O)—$, $R^{18}R^{19}NC(=O)—$ or $R^{18}OC(=O)—O—$, $R^2=$H,
(1',2'-cis)-OH,
(1',2'-trans)-OH,
(1',2'-cis)-$OR^{15}$,
(1',2'-trans)-$OR^{15}$,
(1',2'-cis)-SH,
(1',2'-cis)-S—Y—$R^{13}$,
or the $R^1$ and $R^2$ bearing atoms are connected via a -OC(=O)$CHR^{16}$-element, $R^{3a}$, $R^{3b}$=independently H,
$R^1$,
OH,
$OR^{11}$,
$NR^{10}R^{11}$,
or $R^{3a}=R^{3b}=(=O)$,
$(=NR^1)$,
$O(CH_2)_kO—$ wherein k is 2 or 3, $R^4=$H,
$C(=O)—Y—R^{15}$, or
$C(=O)—R^{15}$, $R^5=$H,
or $R^4$, $R^5$ are connected by -Z-, $R^6=$H, or
$CH_3$, $R^7=$H,
$CH_3$,
Y—$R^{13}$,
$C(=O)—Y—R^{15}$, or
$C(=O)—R^{15}$, $R^8=$H,
Y—$R^{13}$, or
$C(=O)—R^{17}$, $R^9=$H,
$(C_1-C_{10})$alkyl,
$(C_2-C_{10})$alkenyl,
$(C_2-C_{10})$alkynyl,
$(C_1-C_8)[(C_1-C_4)$alkoxy]alkyl,
$(C_2-C_8)[(C_1-C_4)$alkoxy]alkenyl,
$(C_6-C_{10})$aryl-$(C_1-C_5)$alkyl, or
$(C_2-C_9)$heteroaryl-$(C_1-C_5)$alkyl, $R^{10}$,$R^{11}$=independently H,
$(C_1-C_{10})$alkyl,
$(C_2-C_{10})$alkenyl,
$(C_2-C_{10})$alkynyl,
$(C_3-C_{10})$cycloalkyl,
$(C_6-C_{10})$aryl, or
$(C_2-C_9)$heteroaryl, wherein alkyl, alkenyl, alkynyl, cycloalkyl, aryl, heteroaryl are optionally substituted by one to three halogen, cyano, hydroxy, $(C_1-C_4)$alkyloxy, nitro, $(C_1-C_6)$alkyl, $(C_2-C_6)$alkenyl, $(C_2-C_6)$alkynyl, $(C_3-C_7)$cycloalkyl), $(C_1-C_6)$heterocycloalkyl, $(C_6-C_{10})$aryl, $(C_1-C_9)$heteroaryl, $NR^{18}R^{19}$, $R^{18}C(=O)—$, $R^{18}C(=O)O—$, $R^{18}OC(=O)—$, $R^{18}C(=O)NH—$, $R^{18}NHC(=O)—$, $R^{18}R^{19}NC(=O)—$ or $R^{18}OC(=O)—O—$,
or $R^{10}$=H and
$R^{11}$=Y—$R^{13}$, $C(=O)—Y—R^{15}$,
$C(=O)—R^{15}$,
$S(=O)_k(C_1-C_{10})$alkyl,
$S(=O)_k(C_2-C_{10})$alkenyl,
$S(=O)_k(C_2-C_{10})$alkynyl,
$S(=O)_k(C_6-C_{10})$aryl,
$S(=O)_k(C_2-C_9)$heteroaryl,
$S(=O)_k—Y—R^{15}$, or
$S(=O)_k—R^{15}$, wherein k is 0, 1 or 2 and alky, alkenyl, alkynyl, cycloalkyl, heterocycloalkyl, aryl and heteroaryl can be substituted as defined above, $R^{12}=$H,
$(C_1-C_{10})$alkyl,
$(C_2-C_{10})$alkenyl,
$(C_2-C_{10})$alkynyl,
$(C_1-C_8)[(C_1-C_4)$alkoxy]alkyl,
$(C_2-C_8)[(C_1-C_4)$alkoxy]alkenyl,
$(C_6-C_{10})$aryl-$(C_1-C_5)$alkyl,
$(C_2-C_9)$heteroaryl-$(C_1-C_5)$alkyl,
$(C_1-C_4)$alkyliden-$NR^{18}R^{19}$, or
Y—$R^{13}$, $R^{13}$=independently, non-steroidal anti-inflammatory therapeutic agent, $R^{15}$=independently, non-steroidal anti-inflammatory therapeutic agent, $R^{16}$=independently, H,
$CH_3$,
$(C_2-C_{10})$alkyl,
$(C_2-C_{10})$alkenyl,
$(C_2-C_{10})$alkynyl,
$(C_1-C_8)[(C_1-C_4)$alkoxy]alkyl,
$(C_2-C_8)[(C_1-C_4)$alkoxy]alkenyl,
$(C_6-C_{10})$aryl-$(C_1-C_5)$alkyl,
$(C_2-C_9)$heteroaryl-$(C_1-C_5)$alkyl,
$(C_1-C_4)$alkyliden-$NR^{18}R^{19}$, or
Y—$R^{13}$, $R^{17}$=O—$R^{20}$-aryl
optionally substituted by —X'—Y-non-steroidal anti-inflammatory therapeutic agent, or
X'-non-steroidal anti-inflammatory therapeutic agent
wherein X' is
S, O, or NH, $R^{18}$, $R^{19}$=independently H,
$(C_1-C_{10})$alkyl,
$(C_2-C_{10})$alkenyl,
$(C_2-C_{10})$alkynyl,
$(C_1-C_8)[(C_1-C_4)$alkoxy]alkyl,
$(C_2-C_8)[(C_1-C_4)$alkoxy]alkenyl,
$(C_6-C_{10})$aryl-$(C_1-C_5)$alkyl, or
$(C_2-C_9)$heteroaryl-$(C_1-C_5)$alkyl, $R^{20}$=independently,
Halogen,
$(C_1-C_3)$alkyl,
$NO_2$,
CN,
$OCH_3$,
$N(CH_3)_2$,
$N_3$,
SH, or
$S(C_1-C_4)$alkyl;

wherein the compound has at least one of $R^{13}$, $R^{15}$ or $R^{17}$ comprising a non-steroidal anti-inflammatory therapeutic agent.

2. A pharmaceutical composition comprising a compound of claim 1 and a pharmaceutically acceptable carrier.

3. A method of treating an inflammatory disorder, comprising administering to a subject in need thereof an effective amount of a compound of claim 1.

* * * * *